US009029377B2

(12) United States Patent
Ogawa et al.

(10) Patent No.: US 9,029,377 B2
(45) Date of Patent: May 12, 2015

(54) PLATELET-ACTIVATING FACTOR RECEPTOR ANTAGONISTS

(75) Inventors: Anthony Ogawa, Mountainside, NJ (US); Feroze Ujjainwalla, Scotch Plains, NJ (US); Lin Chu, Scotch Plains, NJ (US); Bing Li, Towaco, NJ (US); Lan Wei, Edison, NJ (US); Jinyou Xu, Scotch Palins, NJ (US); Hyun Ok, Colonia, NJ (US); Aaron Lackner, Berkley, CA (US); Ihor Kopka, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 191 days.

(21) Appl. No.: 13/382,469

(22) PCT Filed: Jun. 28, 2010

(86) PCT No.: PCT/US2010/040123
§ 371 (c)(1),
(2), (4) Date: Jan. 5, 2012

(87) PCT Pub. No.: WO2011/005608
PCT Pub. Date: Jan. 13, 2011

(65) Prior Publication Data
US 2012/0108595 A1    May 3, 2012

Related U.S. Application Data

(60) Provisional application No. 61/223,460, filed on Jul. 7, 2009.

(51) Int. Cl.
| | | |
|---|---|---|
| A61K 31/50 | (2006.01) |
| A61K 31/4965 | (2006.01) |
| A61K 31/505 | (2006.01) |
| A61K 31/44 | (2006.01) |
| A61K 31/4245 | (2006.01) |
| A61K 31/4196 | (2006.01) |
| A61K 31/42 | (2006.01) |
| C07D 487/00 | (2006.01) |
| C07D 401/00 | (2006.01) |
| C07D 403/00 | (2006.01) |
| C07D 231/02 | (2006.01) |
| C07D 271/00 | (2006.01) |
| C07D 261/02 | (2006.01) |
| C07D 249/08 | (2006.01) |
| G01C 23/00 | (2006.01) |
| G08G 5/00 | (2006.01) |

(52) U.S. Cl.
CPC .............. *G01C 23/00* (2013.01); *G08G 5/0056* (2013.01)

(58) Field of Classification Search
USPC ............... 514/248, 255.05, 259.31, 275, 300, 514/340, 364, 378, 383; 544/236, 281, 331; 546/121, 272.4; 548/110, 131, 249, 548/262.2, 266.2
See application file for complete search history.

(56) References Cited

FOREIGN PATENT DOCUMENTS

| WO | WO 93/14069 | 7/1993 | |
|---|---|---|---|
| WO | WO 93/14069 A1 * | 7/1993 | .......... C07D 233/54 |
| WO | WO 94/12500 | 6/1994 | |

OTHER PUBLICATIONS

Ito, Nobuyuki. Cancer Science 94(1), (2003) 3-8.*
Database Registry Chemical Abstracts Service, Columbus, Ohio, Accession No. RN 157670-18-3, Entered STN: Sep. 15, 1994.*
Sestanj, Kazimir. Synthesis of Epibatidine. Tetrahedron Letters. 35(30), 5417-5420, 1994.*
Samanta et al., Crystal Structure of Human Plasma Platelet-activating Factor Acetylhydrolase, Journal of Biological Chemistry vol. 283(46), pp. 31617-31624, Nov. 14, 2008, p. 31618-31621.
International Search Report for International application No. PCT/US 10/40123; Date of the actual completion of the international search Aug. 12, 2010; Completed by Authorized officer: Lee W. Young.

* cited by examiner

*Primary Examiner* — Samantha Shterengarts
(74) *Attorney, Agent, or Firm* — Dianne Pecoraro; Catherin D. Fitch

(57) ABSTRACT

Cyclohexyl sulfonamide compounds which are platelet-activating factor (PAF) receptor antagonists. Said compounds may be useful, for example, for the treatment of atherosclerosis or other PAF-mediated disorders, including inflammatory, cardiovascular, and immune disorders.

9 Claims, No Drawings

PLATELET-ACTIVATING FACTOR RECEPTOR ANTAGONISTS

TECHNICAL FIELD

This invention relates to cyclohexyl sulfonamide compounds which have platelet-activating factor (PAF) receptor antagonist activity, pharmaceutical compositions containing these compounds, and methods of treating PAF-mediated disorders, including inflammatory, cardiovascular and immune disorders.

BACKGROUND OF THE INVENTION

Platelet-activating factor (PAF, 1-Alkyl-2-acetyl-sn-glycerophospho-choline) is a potent inflammatory phospholipid mediator that binds to and activates the platelet-activating factor receptors (PAFR). PAF is produced and released by monocytes, macrophages, polymorphonuclear leukocytes, eosinophils, neutrophils, natural killer lymphocytes, platelets and endothelial cells, as well as by renal and cardiac tissues. PAF is similar to other lipid mediators such as thromboxane A, prostaglandins, and leukotrienes with respect to the level of potency, i.e., activity at concentrations of $10^{-12}$-$10^{-9}$ M, tissue amount (picomoles) and short plasma half life (2-4 minutes). PAF is physiologically active and causes contraction of the airway smooth muscle, increased vascular permeability, platelet aggregation, and hypotension. See, e.g., Stafforini et al. *Crit. Rev. Clin. Lab Sci.* 2003, 40, 643-672.

PAF has been reported to participate in several aspects of the inflammatory response associated with the pathogenesis of atherosclerosis, however, the precise role of PAF and the PAFR has not been defined. PAF activates the adhesive interaction of leukocytes with the vascular endothelium and the transmigration of leukocytes, promotes the release of reactive oxygen species and tissue-damaging enzymes from leukocytes and endothelial cells, induces the synthesis of inflammatory cytokines from monocytes, and causes the aggregation and degranulation of platelets. In addition, the PAFR has been shown to recognize both PAF and PAF-like oxidized phospholipids on LDL and may promote an inflammatory response to them (see, e.g., Leitinger, N. *Curr. Opin. Lipidol.* 2003, 14, 421-430). A PAFR antagonist was reported to reduce atherosclerotic lesion area by 62% in LDLR−/− mice fed an atherogenic diet (Subbanagounder, G. et al., *Circ. Res.* 1999, 85, 311-318). PAF may also promote smooth muscle cell proliferation, angiogenesis and elastase release. These activities have the potential to contribute to lesion formation or to the generation of occlusive thrombi at the site of plaque rupture (see, e.g., Demopoulos, C. A. et al., *Eur. J. Lipid Sci. Technol.* 2003, 105, 705-716).

PAF has also been implicated in both peripheral and neuropathic pain responses. It is well known that PAF can induce hyperalgesia when injected subcutaneously into a rat paw and PAFR antagonists were reported to decrease the inflammatory nociceptive response in rats (Teather, L. A. *Psychopharmacology* 2002, 163, 430-433). PAF may also mediate neuropathic pain responses. Intrathecal administration of PAF in mice caused the development of tactile allodynia and thermal hyperalgesia (Morita, K. et al., *Pain* 2004, 111, 351-359). PAF is expressed in the spinal cord and dorsal root ganglia (DRG) neurons. A PAFR agonist evoked an intracellular $Ca^{2+}$ flux in capsaicin-sensitive DRG but not in Pafr$^{-/-}$ mice, and it has been proposed that PAF may function in both persistent pain and the sensitization of primary sensory neurons after tissue injury (Tsuda, M. et al., *J. Neurochem.* 2007, 102, 1658-1668).

PAF also appears to play a role in pathological allergic, hypersecretory and additional inflammatory responses. Many published studies suggest the involvement of PAF in autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, inflammatory bowel diseases, edema, rhinitis, thrombosis, bronchitis, urticaria, psoriasis, retinal and corneal diseases, chemically induced liver cirrhosis, and ovimplantation in pregnancy, and acute respiratory distress syndrome. (See, e.g., Piper, P. J. et al., *Ann. NY Acad. Sci.* 1991, 629, 112-119; Holtzman, M. J. *Am. Rev. Respir. Dis.* 1991, 143, 188-203; Snyder, F. *Am. J. Physiol. Cell Physiol.* 1990, 259, C697-C708; Prescott, S. M. et al., *J. Biol. Chem.* 1990, 265, 17381-17384; (cardiac diseases) Feuerstein, G. et al., *J Lipid Mediat. Cell Signal.* 1997, 15, 255-284; (liver injury) Karidis, N. P. et al., *World J. Gastroenterol.* 2006, 12, 3695-3706; (pancreatitis) Liu, L. R.; Xia, S. H. *World J. Gastroenterol.* 2006, 12, 539-545; (lung) Uhlig, S, et al., *Pharmacol. Rep.* 2005, 57, 206-221; (thrombosis) Prescott, S. M. et al., *Arterioscler. Thromb. Vasc. Biol.* 2002, 22, 727-733; Ishii, S.; Shimizu, T. *Prog. Lipid Res.* 2000, 39, 41-82). Compounds and/or pharmaceutical compositions which act as PAF receptor antagonists should be of significant utility in the treatment of any of the above conditions.

Despite significant therapeutic advances in the treatment and prevention of atherosclerosis and ensuing atherosclerotic disease events, such as the improvements that have been achieved with HMG-CoA reductase inhibitors, further treatment options are clearly needed. Moreover, there is a need for additional treatment options, in addition to the therapeutics that exist, for the treatment of both inflammatory and neuropathic pain. The instant invention addresses those needs by providing compounds, pharmaceutical compositions and methods for the treatment or prevention of atherosclerosis and pain as well as other conditions. As PAF has been implicated in such diverse pathologic processes as allergy, asthma, septic shock, arterial thrombosis, adult respiratory distress syndrome, glomerulonephritis, gastric ulceration, cerebral, pancreatitis, preeclampsia, myocardial and renal ischemia, inflammatory processes, immune regulation, transplant rejection, and psoriasis (see e.g., Prescott et al., J. Biol. Chem. 265:17381-17384 (1990)), such novel compounds are of clear utility.

SUMMARY OF THE INVENTION

The present invention provides compounds of formula I and pharmaceutically acceptable salts thereof:

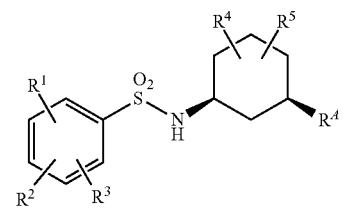

wherein $R_1$, and $R_2$ are each independently selected from the group consisting of H, halogen, small alkyl, small alkoxy, small cycloalkyl, small haloalkyl, small haloalkoxy, or —$OC_1$-$C_4$alkyl, optionally substituted with fluoro;

$R_3$ is selected from the group consisting of substituted or unsubstituted mono- or polycyclic aryl or heteroaryl, H, halogen, amide, $OCF_3$, small alkyl, small cycloalkyl, or small alkoxy;

$R_4$ and $R_5$ are H, OH, or F, with the proviso that when $R_4$ is OH, then $R_5$ is H; and $R^A$ is a substituted or unsubstituted 5-membered or 6-membered heteroaryl.

This invention also involves the use of compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of Formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

The compounds of Formula I are also useful as to treat or ameliorate inflammatory pain and nociceptive pain. They are also useful to treat or ameliorate autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, inflammatory bowel diseases, edema, rhinitis, thrombosis, bronchitis, urticaria, psoriasis, retinal and corneal diseases, chemically induced liver cirrhosis, and ovimplantation in pregnancy, and acute respiratory distress syndrome. The instant invention provides methods of treatment comprising administering a therapeutically effective amount of a compound of Formula I to a patient in need of the above-described treatments.

A further object is to provide the use of PAFR inhibitors of Formula I in combination with other therapeutically effective agents, including other drugs useful for the treatment of atherosclerosis and pain. These and other objects will be evident from the description contained herein.

DETAILED DESCRIPTION OF THE INVENTION

The present invention provides compounds of formula I and pharmaceutically acceptable salts thereof:

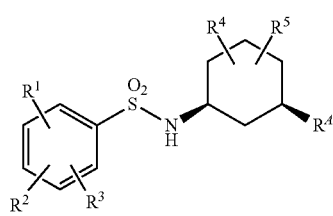

I wherein $R_1$, and $R_2$ are each independently selected from the group consisting of H, halogen, small alkyl, small alkoxy, small cycloalkyl, small haloalkyl, small haloalkoxy, or —$OC_1$-$C_4$alkyl, optionally substituted with fluoro;

$R_3$ is selected from the group consisting of substituted or unsubstituted mono- or polycyclic aryl or heteroaryl, H, halogen, amide, $OCF_3$, small alkyl, small cycloalkyl, or small alkoxy;

$R_4$ and $R_5$ are H, OH, or F, with the proviso that when $R_4$ is OH, then $R_5$ is H; and $R^A$ is a substituted or unsubstituted 5-membered or 6-membered heteroaryl.

In a preferred embodiment, $R^A$ is 3-pyridyl.

In another preferred embodiment, $R^A$ is

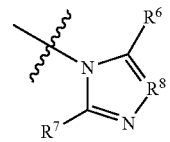

wherein $R^6$ and $R^7$ are each independently selected from the group consisting of H, small alkyl, cycloalkyl, hydroxymethyl, and carboxymethyl. $R^8$ is independently selected from N or CH.

In another embodiment, $R^A$ is

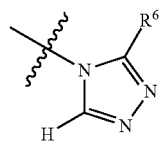

wherein $R^6$ is H or $C_{1-6}$ alkyl, most preferably methyl.

In yet another embodiment, $R^A$ is

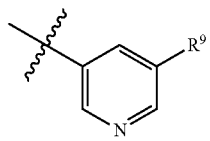

wherein $R^9$ is H, F, small alkyl, OH or $NH_2$, most preferably H.

The present invention further provides compounds of formula II and pharmaceutically acceptable salts thereof:

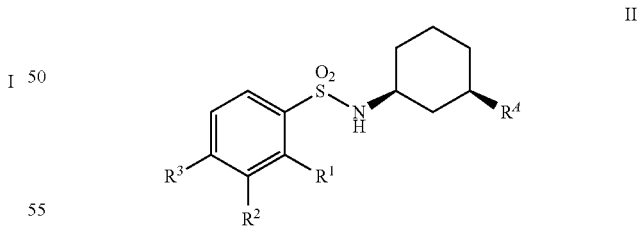

II wherein, $R^1$ is H, F, small alkyl, small cycloalkyl, small alkoxy, or $OCF_3$ $R^2$ is H, F, small alkyl or small alkoxy;

$R^3$ is 5 or 6-membered aryl or heteroaryl, H, amide, or small alkoxy; and $R^A$ is a substituted or unsubstituted 5-membered or 6-membered heteroaryl.

The present invention provides compounds of Formula III and pharmaceutically acceptable salts thereof:

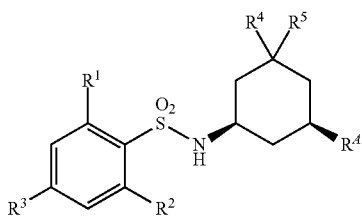

wherein, $R^1$ is H, F, small alkyl, small cycloalkyl, small alkoxy, $OCF_3$;

$R^2$ is H, small alkyl, small alkoxy; and $R^3$ is small alkyl, small alkoxy, or 5- or 6-membered aryl or heteroaryl;

$R_4$ and $R_5$ are H, OH, or F, with the proviso that when $R_4$ is OH, then $R_5$ is H; and $R^4$ is a substituted or unsubstituted 5-membered or 6-membered heteroaryl.

The present invention further provides compounds of Formula IV:

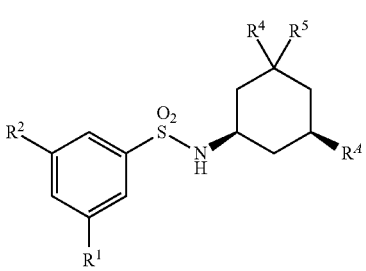

wherein $R^1$ is small alkyl, haloalkyl, alkoxy and haloalkoxy;

$R^2$ is F, $OCF_3$, small alkyl, 5 or 6-membered aryl or heteroaryl or 9 or 10-membered heteroaryl;

$R_4$ and $R_5$ are H, OH, or F, with the proviso that when $R_4$ is OH, then $R_5$ is H; and $R^4$ is a substituted or unsubstituted 5-membered or 6-membered heteroaryl.

The present invention further provides compounds of Formula V:

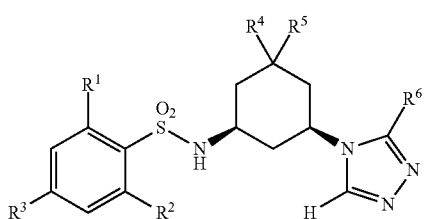

wherein $R^1$, $R^2$ and $R^3$ are small alkyl, small cycloalkyl; in a preferred embodiment, isopropyl;

$R_4$ and $R_5$ are H, OH, or F, with the proviso that when $R_4$ is OH, then $R_5$ is H; and $R^6$ is small alkyl or small cycloalkyl.

The present invention further provides a method for the treatment of a condition in which the PAFR is implicated, e.g. atherosclerosis, comprising the step of administering a therapeutically effective amount of a compound of Formula I to a patient in need of such treatment.

As used herein, the term "alkyl" means carbon chains which may be linear or branched, or combinations thereof, containing the indicated number of carbon atoms. Examples of alkyl groups include methyl (Me), ethyl (Et), propyl, isopropyl (i-propyl, iPr), butyl, sec- and tert-butyl (s-butyl, t-butyl, sBu, tBu), pentyl, hexyl, and the like.

"Small alkyl" is $C_1$-$C_6$ alkyl, i.e., an alkyl group having from 1 to 6 carbon atoms. The small alkyl may be unsubstituted or substituted, e.g., with fluorine. "Cycloalkyl" is intended to be a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule.

"Halogen" (Halo) includes fluoro, chloro, bromo and iodo, most preferably fluoro.

"Aryl" as used herein, refers to an optionally substituted, mono- or polycyclic aromatic ring system. In a preferred embodiment, the aryl is 5 or 6-membered. "Heteroaryl" refers to an optionally substituted, mono- or polycyclic aromatic ring system that includes at least one oxygen, or nitrogen heteroatom ring members. In preferred embodiments, the heteroaryl is 5 or 6-membered. In another preferred embodiment, the heteroaryl is 9- or 10-membered.

As used herein, "heterocyclic ring" and "heterocycle" mean an aromatic or partially unsaturated heterocyclic ring containing one or more carbon atoms and one or more heteroatoms selected from nitrogen (N), oxygen (O) and sulfur (S), in total containing 5 to 6 atoms in the ring. A bicyclic heterocyclic ring system similarly means an aromatic or partially unsaturated bicyclic ring system containing one or more carbon atoms and one or more heteroatoms selected from nitrogen (N), oxygen (O) and sulfur (S), in total containing 9 to 10 atoms in the ring. For mono- and bicyclic heterocyclic rings containing one or more of N, it is understood that the nitrogen may be present in the ring as =N— or —NH— in accordance with the degree of unsaturation in the ring. A heterocyclic ring or bicyclic ring system may be more specifically defined where appropriate in the specification, for example with respect to the number of members (i.e., atoms) in the ring and/or the type and quantity of heteroatoms in the ring, or the point of attachment between two rings in a bicyclic ring system. Examples of aromatic or partially unsaturated heterocyclic rings include but are not limited to pyridyl, pyrimidyl, imidazolyl, tetrazolyl, triazolyl, pyrazolyl, thiazolyl, isoxazolyl, and the like. For 5-membered aromatic or partially unsaturated heterocyclic rings, the point of attachment in a compound structure may be via any available carbon or nitrogen in the ring which results in the creation of a stable structure, unless specified otherwise. For 6-membered aromatic or partially unsaturated heterocyclic rings, the point of attachment in a compound structure may be via any available carbon in the ring which results in the creation of a stable structure, unless specified otherwise. The heterocyclic ring or ring system may be substituted on any available carbon or nitrogen in the ring which results in the creation of a stable structure.

The phrases "optionally substituted" and "optionally substituted with one or more substituents" are both intended to mean that the total number of substituents on the optionally substituted moiety overall may be zero, one or more than one, and that each carbon and heteroatom (when present) available for substitution in the given moiety may independently be unsubstituted or mono- or poly-substituted, with one or more substituents that are the same or different at each occurrence and which result in the creation of a stable structure as is understood to be reasonable by one skilled in the art.

Reference to the compounds of this invention as those of a specific formula or embodiment (e.g., Formula I, Formula II, etc.) or any other generic structural formula or specific compounds described or claimed herein is intended to encompass the specific compound or compounds falling within the scope of the generic structural formula or embodiments including salts thereof, particularly pharmaceutically acceptable salts, as well as the esters and/or solvates of such compounds and salts thereof, where such forms are possible unless specified otherwise. The term "pharmaceutically acceptable salts" refers to salts prepared from pharmaceutically acceptable non-toxic bases or acids including inorganic or organic bases and inorganic or organic acids.

Any pharmaceutically acceptable pro-drug modification which results in conversion in vivo to an active form of a compound within the scope of this invention is also within the scope of this invention. For example, esters can optionally be made by esterification of an available carboxylic acid group or by formation of an ester on an available hydroxy group in a compound. Pharmaceutically acceptable esters of the compounds of this invention may serve as pro-drugs which can be hydrolyzed back to their acid or hydroxy form particularly in vivo and as such are encompassed within the scope of this invention.

The compounds of Formula I may contain one or more asymmetric centers, and can thus occur as racemates, racemic mixtures, single enantiomers, diastereoisomeric mixtures and individual diastereoisomers. The present invention includes all such isomers, as well as salts, esters and/or solvates of such racemates, mixtures, enantiomers and diastereoisomers. Compounds of structural Formula I may be separated into their individual diastereoisomers by, e.g., fractional crystallization from suitable solvents, e.g., DCM/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, synthesis can be performed using one or more chiral intermediates which results in a chiral final product.

Furthermore, compounds of the present invention may exist in amorphous or crystalline physical forms, and a single compound may exist in more than one polymorphic crystalline form. All such physical forms are intended to be included in the scope of the present invention. In addition, some of the compounds of the instant invention may form solvates with water (hydrates) or with common organic solvents. Such solvates and hydrates are likewise encompassed within the scope of this invention.

Accordingly, the compounds within the generic structural formulas and specific compounds described and claimed herein encompass salts thereof, esters thereof, and salts of esters thereof where such forms are possible unless specified otherwise. The instant invention further encompasses all possible stereoisomers, physical forms (e.g., amorphous and crystalline forms), solvate forms, tautomers and combinations of these forms of the compounds falling within the generic structural formulas as well as the specific compounds described and claimed herein, the salts thereof, esters thereof, and salts of esters thereof, where such forms are possible unless specified otherwise.

This invention involves the use of the PAF receptor antagonist compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of Formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A compound of Formula I of the instant invention may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. Accordingly, the instant invention also provides a method for preventing or reducing the risk of a first or subsequent occurrence of an atherosclerotic disease event comprising the administration of a prophylactically effective amount of a compound of Formula I to a patient at risk for such an event. The patient may already have atherosclerotic disease at the time of administration, or may be at risk for developing it.

This invention also involves the use of compounds of Formula I described herein to treat or ameliorate inflammatory pain and nociceptive pain. Therefore, one object of the instant invention is to provide a method for treating pain, comprising administering a therapeutically effective amount of a compound of Formula I to a patient in need of such treatment. Another object is to provide methods for preventing or reducing the risk of developing inflammatory and nociceptive pain, comprising administering a prophylactically effective amount of a compound of Formula I to a patient who is at risk of developing inflammatory or nociceptive pain.

Compounds and/or pharmaceutical compositions which act as PAF receptor antagonists appear to play a role in pathological allergic, hypersecretory and inflammatory responses. Many published studies suggest the involvement of PAF in autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, myocardial infarction, inflammatory bowel diseases, pain, edema, rhinitis, thrombosis, bronchitis, urticaria, psoriasis, retinal and corneal diseases, chemically induced liver cirrhosis, and ovimplantation in pregnancy, and acute respiratory distress syndrome. Accordingly, another object of the instant invention is to provide a method for treating a PAF receptor mediated medical condition, particularly a pathological allergic, hypersecretory and/or inflammatory condition including those conditions described above, comprising administering a therapeutically effective amount of a compound of Formula I to a patient in need of such treatment.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment atherosclerosis or pain, and a prophylactically effective amount, e.g., for prevention of an atherosclerotic disease event or inflammatory or neuropathic pain.

In general, PAFR antagonists can be identified as those compounds which have an $IC_{50}$ in the "PAF Binding Assay" that is less than or equal to about 1 μM, and preferably 200 nM or less, and most preferably 40 nM or less.

An effective amount of a PAFR antagonist in the method of this invention is in the range of about 0.1 mg/kg to about 100 mg/kg of body weight per day, preferably 0.1 mg to about 30 mg per kg, in single or divided doses. A single daily dose is preferred but not necessary. For an average body weight of 70 kg, the dosage level is therefore from about 7 mg to about 2000 mg of drug dosed one to four times per day, e.g. 10 mg, 25 mg, 50 mg, 75 mg, 100 mg, 125 mg, 150 mg, 175 mg, 200 mg, 250 mg, 500 mg, 1000 mg, 1500 mg, or 2000 mg per dose, preferably given as a single daily dose or in divided doses two to four times a day, or in sustained release form. It will be understood, however, that the specific dose level for any particular patient will depend upon a variety of factors including the age, body weight, general health, sex, diet, time of administration, route of administration, rate of excretion, drug combination and the severity of the patient's condition. A consideration of these factors is well within the purview of the ordinarily skilled clinician for the purpose of determining the therapeutically effective or prophylactically effective dosage amount needed to prevent, counter, or arrest the progress of the condition. It is expected that the PAFR antagonist will administered chronically on a daily basis for a length of time appropriate to treat or prevent the medical condition relevant to the patient, including a course of therapy lasting months, years or the life of the patient.

A therapeutically effective amount of a compound of this invention can be used for the preparation of a medicament useful for treating or preventing any of the medical conditions described herein, in dosage amounts described herein. For example, a compound of this invention can be used for the preparation of a medicament useful for preventing or reducing the risk of developing atherosclerotic disease, halting or slowing the progression of atherosclerotic disease once it has become clinically manifest, and/or preventing or reducing the risk of a first or subsequent occurrence of an atherosclerotic disease event. A compound of this invention can also be used for the preparation of a medicament useful for treating pain. Additionally, a compound of this invention can be used for the preparation of a medicament useful for the treatment of a pathological allergic, hypersecretory and/or inflammatory condition including such conditions described herein. The medicament comprised of a compound of this invention may also be prepared with one or more additional active agents, such as those described below.

One or more additional active agents may be administered with a compound of Formula I. The term "additional active agent (or agents)" is intended to mean a pharmaceutically active agent (or agents) different from the compound of Formula I. In a broad embodiment, any suitable additional active agent or agents, including but not limited to anti-atherosclerotic agents such as a lipid modifying compound, anti-diabetic agents and/or anti-obesity agents, and additional pain-reducing agents may be used in any combination with the compound of Formula I in a single dosage formulation, or may be administered to the patient in one or more separate dosage formulations, which allows for concurrent or sequential administration of the active agents. The additional active agent or agents may have more than one pharmaceutical activity, for example it may have both lipid-modifying effects and anti-diabetic activity. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin, simvastatin, pravastatin, particularly the sodium salt thereof, fluvastatin particularly the sodium salt thereof, atorvastatin, particularly the calcium salt thereof, pitavastatin, and rosuvastatin; cholesterol absorption inhibitors (CAI), for example ezetimibe or a combination of a CAI with a statin, e.g., ezetimibe with simvastatin or atorvastatin; 5-lipoxygenase inhibitors; cholesterol ester transfer protein (CETP) inhibitors, for example anacetrapib; HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; niacin in immediate-release or controlled release forms, and particularly in niacin in combination with a DP antagonist such as laropiprant and/or with an HMG-CoA reductase inhibitor; niacin receptor agonists such as acipimox and acifran, as well as niacin receptor partial agonists; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril;

calcium channel blockers such as nifedipine and diltiazem; endothelian antagonists; agents that enhance ABCA1 gene expression; FXR and LXR ligands including both inhibitors and agonists; and bisphosphonate compounds such as alendronate sodium. Anti-obesity agents can be employed in combination with a compound of this invention including, but not limited to, sibutramine, orlistat, topiramate, naltrexone, bupriopion, phentermine, and phentermine/topiramate combination; NPY5 antagonists; Acetyl-CoA Carboxylase-1 and -2 (ACC) inhibitors; MCH1R antagonists; and CB1 antagonists/ inverse agonists. Additional anti-diabetes agents which may be employed in combination with a compound of this invention include but are not limited to DPP-4 (dipeptidylpeptidase-4) inhibitors such as sitagliptin and vildagliptin; sulfonylureas e.g., chlorpropamide, tolazamide, glyburide, glipizide, and glimepiride; biguanides, e.g., metformin; alpha-glucosidase inhibitors e.g., acarbose and miglitol; meglitinides e.g., repaglinide; glucagon-receptor antagonists; and glucokinase activators. Other advantageous pharmaceutical combinations comprise the compounds of this invention in combination with anti-cholinergics such as ipratropium bromide and tiotropium, bronchodilators such as the beta agonist salbutamol, metaproterenol, terbutaline, fenoterol, salmeterol, formoterol and the like, and the anti-asthmatic drugs theophylline, choline theophyllinate and enprofylline, and the calcium antagonists nifedipine, diltiazem, nitrendipine, verapamil, nimodipine, felodipine, etc. Compounds of this invention can be used in combination with orally inhaled corticosteroids, such as beclomethasone, budesonide, flunisolide, fluticasone, mometasone, and triamcinolone, and also with inhaled corticosteroid/LABA products such as fluticasone propionate/salmeterol; corticosteroids such as hydrocortisone, methylprednisolone, betamethasone, dexamethasone, beclomethasone, and the like; with leukotriene receptor antagonists such as montelukast; phosphodiesterase 4 (PDE4) inhibitors such as roflumilast, N-Cyclopropyl-1-[3-(1-oxido-3-pyridinylethynyl)phenyl]-1,4-dihydro[1,8]naphthyridin-4-one-3-carboxamide and the compounds disclosed in PCT Publication WO2003/018579; and Very Late Antigen 4 (VLA4) inhibitors such as the compounds disclosed in U.S. Pat. No. 6,229,011, particularly R411 (N-(2-Chloro-6-methylbenzoyl)-4-[(2,6-dichlorobenzoyl)amino]-L-phenylalanine-2-(diethylamino)ethyl ester which is an ester pro-drug of the active moiety, N-(2-chloro-6-methylbenzoyl)-4-[(2,6-dichlorobenzoyl)amino]-L-phenylalanine), and the compounds disclosed in PCT publication WO2006/023396.

Still other types of agent that can be used in combination with the compounds of this invention for the treatment of pain are non-steroidal anti-inflammatory drugs (NSAIDs), for example aspirin, ibuprofen, ketoprofen, and naproxen; non-opioid analgesics such as acetaminophen; and cyclooxygenase-2 (COX-2) inhibitors such as etoricoxib and celecoxib.

In the method of treatment of this invention, the PAFR antagonists may be administered via any suitable route of administration such as orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred.

For oral use, the pharmaceutical compositions of this invention containing the active ingredient may be in forms such as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients.

The compounds of structural formula I of the present invention can be prepared according to the procedures of the following Schemes and Examples, using appropriate materials and are further exemplified by the specific examples which follow. The compounds illustrated in the examples are not, however, to be construed as forming the only genus that is considered as the invention. The examples further illustrate details for the preparation of the compounds of the present invention. All temperatures are degrees Celsius unless otherwise noted. Mass spectra (MS) were measured by electronspray ion-mass spectroscopy.

Some abbreviations used herein are as follows:
Ac is acetyl; AcOH is acetic acid; aq. is aqueous; Ar is Aryl; atm is normal atmospheric pressure; BOC (Boc) is tert-butyloxycarbonyl; Bn is benzyl; Bu is butyl; $^c$Bu is cyclobutyl; $^n$Bu is n-butyl; $^t$Bu is tert-butyl; celite is Celite® diatomaceous earth; CBZ (CBz) is benzyloxycarbonyl; conc. is concentrated (for HCl, conc. is a 12 M aq. solution); cpm is counts per minute; δ is chemical shift; DAST is (diethylamino)sulfur trifluoride; DCM is dichloromethane; d is doublet; DEAD is diethylazodicarboxylate; DIAD is diisopropylazodicarboxylate; DIBAL-H is diisobutylaluminum hydride; DIPEA is N,N-diisopropylethylamine; DMA is N,N-dimethylacetamide; DMAP is 4-dimethylaminopyridine; DMF is N,N-dimethylformamide; DMF-DMA is N,N-dimethylformamide dimethyl acetal; DMSO is dimethyl sulfoxide; DPPA is diphenylphorphorylazide; dppf is 1,1'-bis(diphenylphosphino)ferrocene; EDC is 1-(3-dimethylaminopropyl)-3-ethylcarbodiimde. HCl; equiv. is equivalent(s); ES-MS is electrospray ion-mass spectroscopy; Et is ethyl; EtOAc is ethyl acetate; EtOH is ethanol; g is gram; h is hours; HATU is O-(7-azabenzotriazol-1-yl)-1,1-3,3-tetramethyluronium hexafluorophosphate; HCl is hydrogen chloride; HetAr or HAR is heteroaryl; $^1$HNMR is proton nuclear magnetic resonance; HOBt is 1-hydroxybenzotriazole; HPLC is high performance liquid chromatography; Hz is hertz; i is Iso; $IC_{50}$ is concentration at which 50% inhibition exists; J is internuclear coupling constant; kg is kilogram; LDA is lithium diisopropylamide; m is meta; m is multiplet; M is molar; mCPBA is 3-chloroperbenzoic acid; Me is methyl; MeOH is methanol; mg is milligram; μg is microgram; MHz is megahertz; min is minute; mL is milliliter; mm is millimeter; μL is microliter; mM is millimolar; μM is micromolar; mmol is millimoles; μmol is micromoles; m.p. is melting point; MS is mass spectrum, and a mass spectrum obtained by ES-MS may be denoted herein by "ES"; Ms is methanesulfonyl; m/z is mass to charge ratio; n is normal; N is normal; nm is nanometer; nM is nanomolar; NMP is N-methylpyrrolidine; nOe is nuclear Overhauser effect; o is ortho; OAc is acetoxy; p is pentet; p is para; PAFR is platelet activating factor receptor; PCC is pyridinium chlorochromate; Ph is phenyl; $^cPr$ is cyclopropyl; $^iPr$ is isopropyl; $^nPr$ is n-propyl; pr is propyl; psi is pounds per square inch of pressure; p-TSA is para-toluenesulfonic acid; q is quartet; rt is room temperature; s is singlet; satd is saturated; sec is secondary; t is triplet; t is tert; Tf is trifluoromethanesulfonyl; TFA is trifluoroacetic acid; TFAA is trifluoroacetic anhydride; THF is tetrahydrofuran; TLC is thin layer chromatography; TMS is trimethylsilyl; Ts is tosyl; UV is ultraviolet; W is watts; wt. % is percentage by weight; × g is times gravity; ° C. is degrees Celsius; % v/v is percentage of the volume of the former agent relative to the volume of the latter agent; % w/v is percentage in weight of the former agent relative to the volume of the latter agent.

Reaction schemes A-M illustrate the methods employed in the synthesis of the compounds of the present invention. All abbreviations are as defined above unless indicated otherwise.

Reaction scheme A illustrates the preferred method for synthesis of compounds of structural formula 5. In this method, a sulfonyl chloride of type 1 is treated with an amine of type 2 in the presence of a tertiary amine, such as DIPEA, in a suitable solvent, such as DCM typically at rt. The sulfonyl chloride reagents are often purchased commercially, but can be readily prepared according to known methods in organic synthesis. Some typical methods for the preparation of sulfonyl chloride will be illustrated in schemes I and J. A compound of type 3 can then be converted to a compound of structural formula 5 using the Suzuki reaction. In this method, 3 is treated with an aryl- or heteroaryl-boronic acid of type 4 or 4a, respectively, in the presence of a suitable catalyst such as [1,1'-bis(diphenylphosphino)ferrocene]-dichloropalladium (II) and aqueous sodium carbonate. The reaction is typically carried out in a suitable combination of inert organic solvents such as toluene-EtOH, at 80° C., for a period of 2-24 h and the product is a biaryl of structural formula 5.

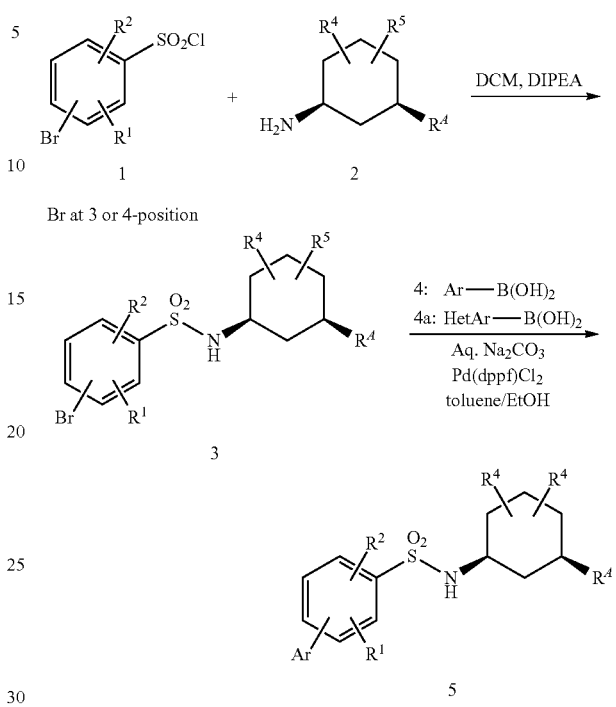

Scheme A

Br at 3 or 4-position

Reaction scheme B illustrates an alternative method for the synthesis of biaryl of type 5. In this method, 3 is first converted to boronate of type 6 via a Pd(0)-catalyzed cross-coupling reaction of 3 with bis(pinacolato)diboron. This reaction is usually performed in DMSO, at about 90° C., for a period of 4-24 h. Treatment of 6 with an aryl- or heteroaryl-bromide or iodide of type 7 or 7a, respectively, in the presence of a suitable catalyst such as [1,1'-bis(diphenylphosphino)ferrocene]-dichloropalladium (II) should provide biaryl of type 5. The reaction is typically carried out in a suitable combination of inert organic solvents such as toluene-EtOH, at 80° C., for a period of 2-24 h.

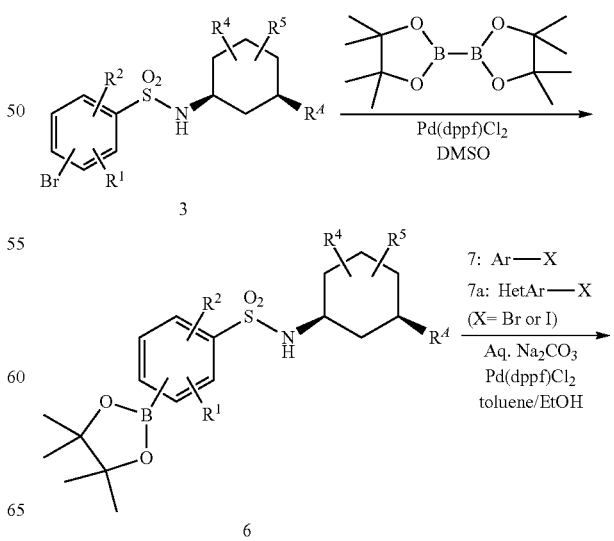

Scheme B

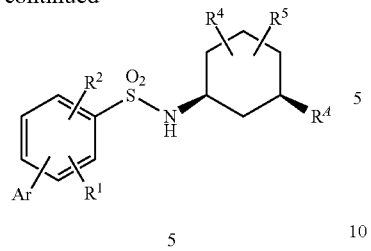

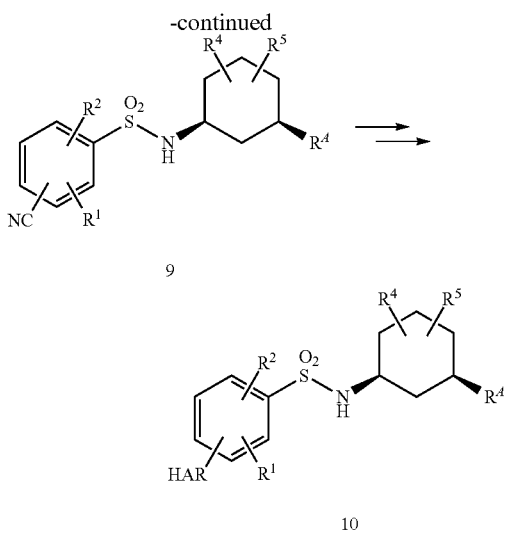

Reaction scheme C illustrated a preferred method of synthesis of compounds of structural formula 10. In this method, a sulfonyl chloride of type 8 is treated with an amine of type 2 in the presence of a tertiary amine, such as diisopropylethylamine, in a suitable solvent, such as dichloromethane at rt. Compounds of structural 9 can then be elaborated to a variety of heterocyclic (HAR) derivatives of structural formula 10 using known methods in organic synthesis. Specific examples of such transformations are shown in the Examples section. Leading references for performing such transformations include:

1) Joule, L A.; Mills, K. and Smith, G. F. *Heterocyclic Chemistry*, Chapman & Hall, 1995, 3rd Edn., and references cited therein;
2) Katrittzky, A. R.; Rees, C. W. (Eds), *Comprehensive heterocyclic Chemistry: The Structure, Reactions, Synthesis, and Uses of heterocyclic Compounds*, Pergamon Press, Oxford, 1984, 8v, and references cited therein and
3) *Comprehensive heterocyclic Chemistry II: Review of the Literature 1982-1995: The Structure, Reactions, Synthesis and Uses of Heterocyclic Compounds*. Pergamon Press, New York, 2nd Edn., 1996, 11v and references cited therein.

Reaction scheme D illustrates an alternative method for the syntheses of compounds of structural formula 9 and 11. In this method, 3 is treated with $Zn(CN)_2$ in the presence of a suitable catalyst such as $Pd(PPh_3)_4$ in an inert organic solvent like DMSO. The reaction is usually conducted at 90° C., for a period of 12-24 h. In specific instances, it may be preferable to carry out the reaction under the influence of microwave irradiation. The product of the reaction is a nitrile (9) that can be elaborated to a variety of heterocyclic (HAR) derivatives of structural formula 10 using known methods in organic synthesis as referenced in Scheme C.

Alternatively, bromide 3 is treated with MeOH in the presence of a suitable catalyst such as [1,1'-bis(diphenylphosphino)ferrocene]-dichloropalladium (II), in an inert organic solvent like DMF. The reaction is usually conducted at elevated temperature, typically between 50-100° C., for periods of 6-24 h, under an atmosphere of carbon monoxide. The product of the reaction is an ester of structural formula 11, which can similarly be elaborated to a variety of heterocyclic (HAR) derivatives of structural formula 10 using known methods in organic synthesis as referenced in Scheme C.

Scheme C

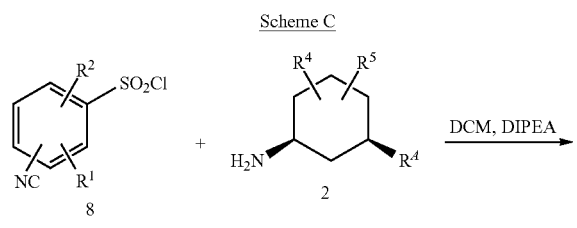

Scheme D

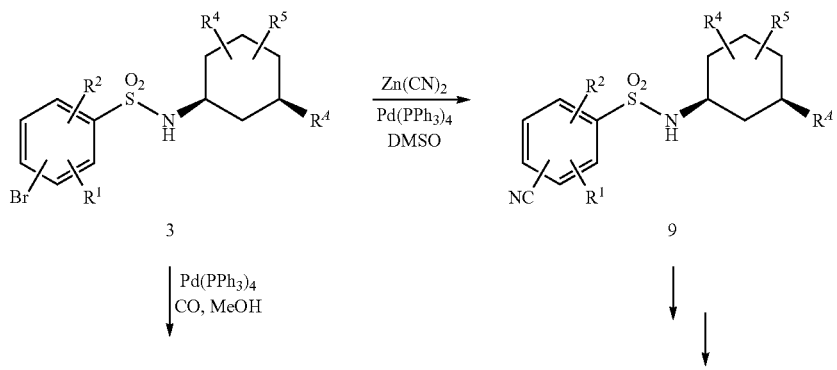

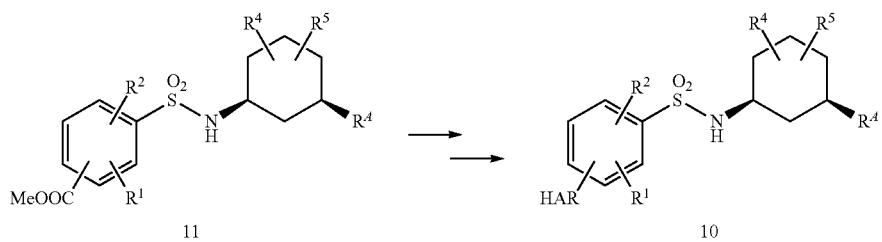

Reaction scheme E illustrates a preferred method for the synthesis of amine of structural formula 2. In this method, 12 is subjected to the Curtius reaction to afford the N-CBz protected amine of structural formula 13. The reaction is carried out by reaction 12 with diphenylphosphoryl azide in the presence of a tertiary amine such as triethylamine or DIPEA in an inert solvent such as toluene. The initial intermediate product of the reaction is generally accepted to be the acyl azide, which rearranges to an isocyanate containing intermediate when the above reaction mixture is heated, typically to temperatures between 90° C. and the boiling point of the reaction for periods of from 1-24 h. The intermediate isocyanate which forms is general not isolated, but is in turn subjected to in situ reaction with a suitable alcohol such as benzyl alcohol or tert-butyl alcohol to afford a carbamate, which specifically in the case of compound 13 is a CBz-protected amine. The N-Boc group from compound 13 can be selectively removed by a suitable deprotection method such as treatment with HCl in MeOH or TFA in DCM. The deprotection is conducted typically at rt and is usually complete in 1-3 h. The product of the reaction is an amine of type 14, which can be reacted with suitable reagents like the aminoacylhydrazone 15 following literature methods (Stocks, M. J.; Cheshire, D. R. and Reynolds, R. *Organic Letters*, 2004, 2969-2971 and references cited therein) that result in 1,2,4-triazoles of type 16. Subsequent removal of the nitrogen protecting group (CBz) in 16 can be achieved under conditions of catalytic hydrogenation, using a variety of palladium-on-carbon catalysts, under an atmosphere of hydrogen in an inert solvent, such as MeOH to afford amines of type 2.

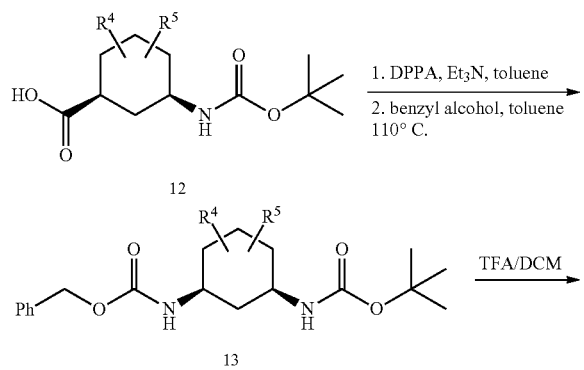

Scheme E

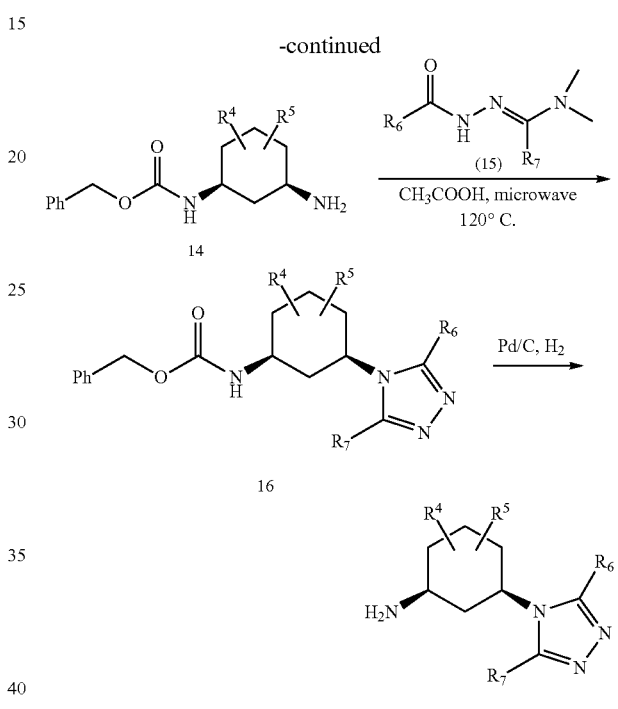

Reaction scheme F illustrates the preferred method for the synthesis of a compound of type 22. In this method, the commercial cis, cis-1,3,5-cyclohexanetriol can be converted to 18 according to literature procedures (S. J. Monger et al. *J. Chem. Soc., Chem. Commun.*, 1989, 381). Compound 18 can be directly alkylated using an alkylating agent of type 19, wherein "X" is a suitable leaving group such as a halide, mesylate, tosylate or triflate. Selective mono-reduction of the azide group in 20 can be achieved by a modification of the Staudinger reaction using trimethylphosphine at low temperatures (P. T. Nyffeler et al. *J. Am. Chem. Soc.*, 2002, 124, 5173). The direct conversion of azide 20 to carbonate 21 can be achieved according to the literature procedures (Ariza et al. *Tetrahedron Lett.* 1998, 39, 9109; Ariza et al. *Tetrahedron Lett.* 1999, 40, 7515). Reduction of the second azide group in 21 requires elevated temperatures, commonly between 50-80° C., in an inert solvent, such as THF, for periods of 2-6 h. The compound 22 can be elaborated to an amine of type 23 using the steps discussed in the scheme E.

Scheme F

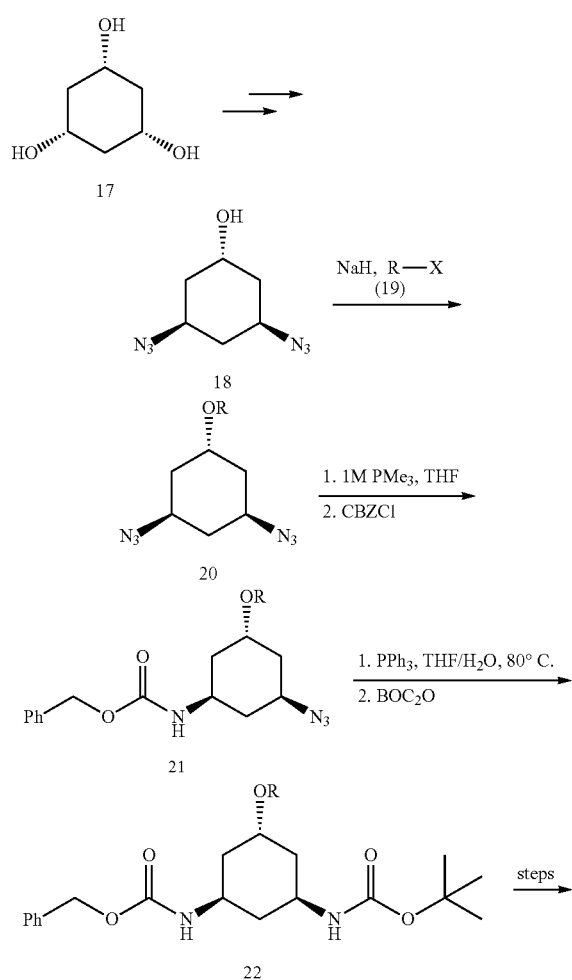

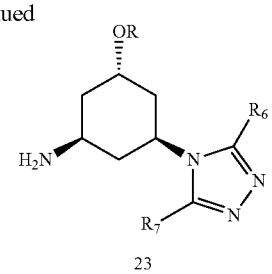

Reaction scheme illustrates the preferred method for the synthesis of amine of structural formula 24, 27 and 29. In this method, 18 is treated with a fluorinating reagent such as DAST or [bis(2-methoxyethyl)amino] sulfur trifluoride to provide 24. This reaction usually proceeds at −78° C., however, in some cases it is necessary to warm the reaction mixture to rt for complete conversion. Highly varied stereochemical outcomes have been obtained in the reactions of DAST with secondary alcohols. Compound 23 can be elaborated to an amine of type 24 using the steps discussed in the scheme E, Treatment of alcohol 18 with TsCl in the presence of pyridine yields compounds of type 25, which can be further reacted in cross-coupling reactions with Grignard reagents in the presence of catalytic quantities of other metals, such as copper species should provide 26, which in turn can be converted to an amine of type 27 using the steps discussed in the scheme E. The configuration of the hydroxy group in 18 can be inverted to give 28 using Mitsunobu reaction (O. S. Mitsunobu, *Org. Synth.* 1981, 1; D. L. Hughes, *Org. React.* 1992, 42, 335). 28 can then be converted to an amine of type 29 following procedures similar to those described above and in Scheme E.

Scheme G

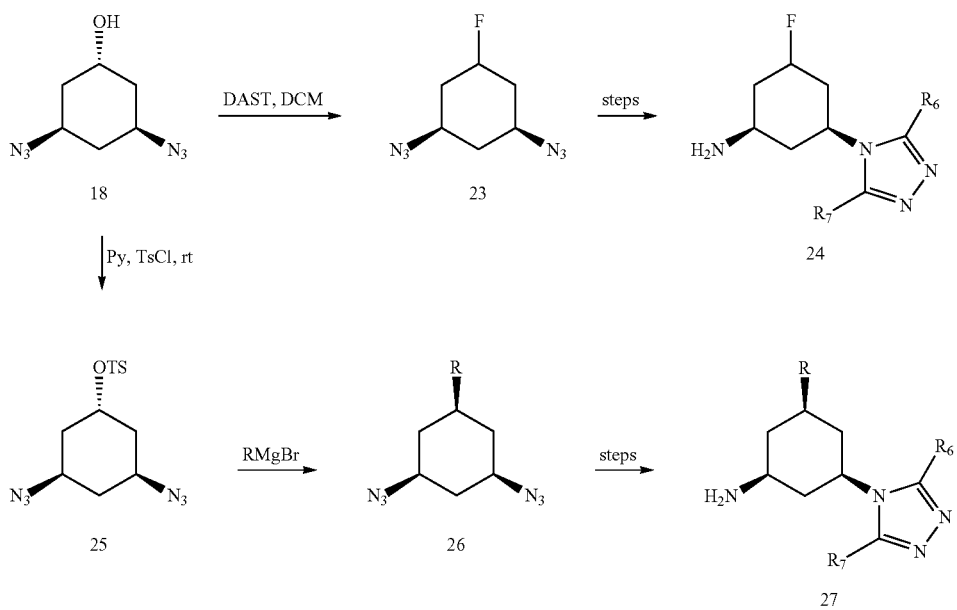

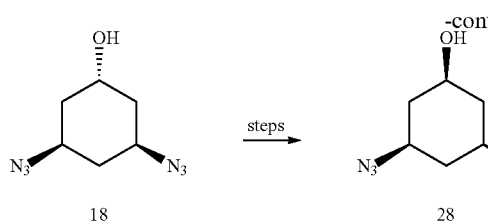
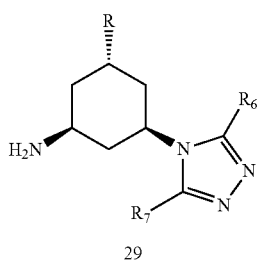

Reaction scheme H illustrates the preferred method for the synthesis of carbamate of type 36. 18 can be oxidized to the corresponding ketone 30 by a variety of methods known to those skilled in the art of organic synthesis. Treatment of 30 with a suitable base, such as LDA, in the presence of TMS-Cl affords a trimethylsilyl enol ether of type 31. The formation of 31 is typically performed in a suitable ethereal solvent, such as THF or diethyl ether, at −78° C. Oxidation of 31 with mCPBA in the presence of sodium bicarbonate at 0° C. for 1 h followed by treatment with 1N HCl yields hydroxy ketone 32 (E. J. Corey et al, *Tetrahedron Lett.* 1998, 29, 995). The ketone function group in 32 can be reduced using the Huang-Minion modification of the Wolff-Kischner reaction, thereby generating an alcohol of type 33. 33 can then be elaborated to an amine of type 36 following the steps outlined in scheme F.

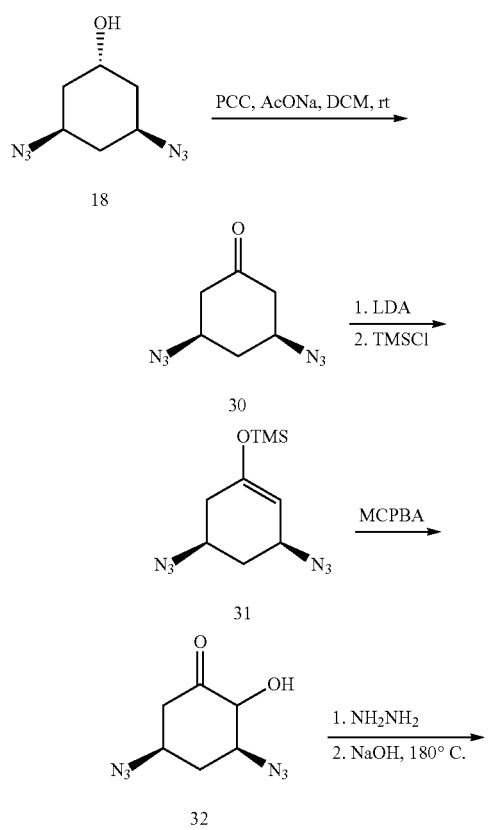

Reaction scheme I illustrates the preferred methods for the synthesis of sulfonyl chloride of type 1a. Compounds of formula 37 are commercially available, known in the literature or may be conveniently prepared by a variety of methods familiar to those skilled in the art (R. C. Larock. *Comprehensive Organic Transformations.* 1999). Conversion of an aniline of type 37 to a sulfonyl chloride of type 1a via its diazonium salt is a well documented reaction (H. Meerwein et al. *Chem. Ber.* 1957, 841; R. V. Hoffman et al. *Org. Synth.* 1990, VII, 508). In this reaction, treatment of aniline 37 with sodium nitrite in a mixture of glacial acetic acid and aqueous hydrochloric acid affords the corresponding diazonium salt. Treatment of the resulting slurry with sulfur dioxide and copper salts should provide a sulfonyl chloride of type 1a.

An alternate strategy for converting aryl amines of type 37 to sulfonyl chlorides of type 1a employs a one pot procedure to afford thioanisoles of type 39. Treatment of amine 37 with isoamyl nitrite under similar conditions as those described above affords a diazonium intermediate (not shown) that is subsequently reacted with a thiol donor, such as dimethyldisulfide, in the presence of a suitable metal catalyst, such as copper metal. The second step is conducted at elevated temperatures, typically between 70-100° C. The products of the reaction, thioanisoles of type 39 are oxidized with a suitable agent, such as mCPBA, to the sulfoxide. The sulfoxide is treated with an acylating agent, such as trifluoracetic anhydride or the like, at reflux in a suitable inert solvent, such as DCM, to yield an acyl sulfoxy intermediate that undergoes a process known to those skilled in the art of organic synthesis as the Pummerer rearrangement. The intermediate of this reaction is further oxidized with chlorine gas in a suitable solvent, such as AcOH, typically at 0° C., to afford sulfonyl chlorides of type 1a.

Scheme I

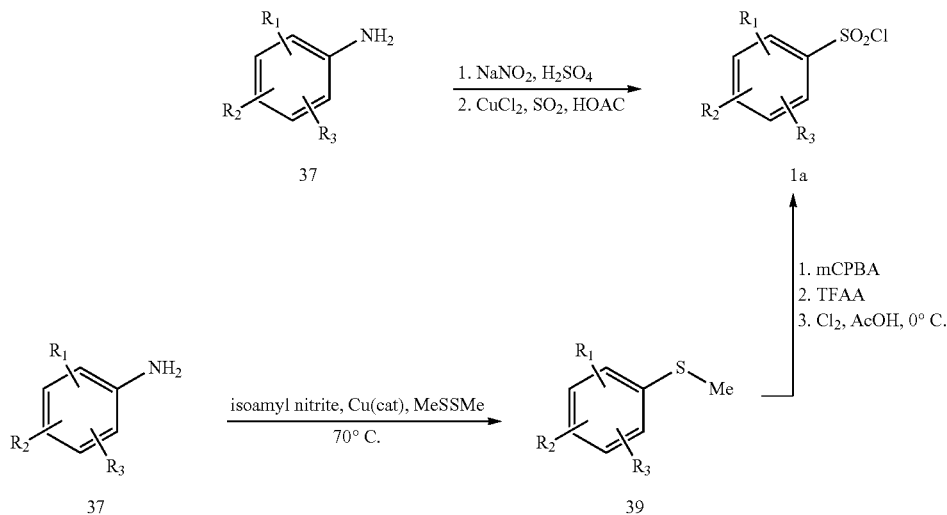

Reaction scheme J illustrates a preferred method for the synthesis of cis-1,3-diaminocyclohexanes of type 46. Starting from commercially available materials, such as dimethyl 5-hydroxyisophthalate (40), hydrogenation at elevated pressure, greater than 50 psi, in the presence of a suitable metal catalyst, such as rhodium adsorbed on alumina, typically for periods of 48-72 h, to afford a syn-5-hydroxy-cis-1,3-dicarboxycyclohexane of type 41. The hydroxyl group from compound 41 can be oxidized to the corresponding ketone following procedures known to those skilled in the art of organic synthesis, such as the Swern oxidation (Mancuso, A. J.; Swern, D. *Synthesis*, 1981, 161). Ketone 42 is subsequently reacted with a fluorinating agent, such as DAST, in an inert solvent, such as 1,2-dichloroethane, typically at 40-60° C., yielding a difluorocyclohexyl intermediate (not shown) that can be further reacted under conditions well known to those skilled in the art of organic synthesis to afford cyclohexane-cis-1,3-dicarboxylic acids of type 43. It should be noted that the former fluorination reaction should be conducted in a sealable inert vessel, such as a polyethylene screw cap bottle. The conversion of diacids of type 43 to the corresponding cis-1,3-amino acids of type 45, involves an initial formation of a maleic anhydride intermediate of type 44, which can be formed from reaction of the diacid (43) with a suitable carboxylic acid activating agent, such as DCC, typically for 8-24 h. Anhydride 44 is reacted with an azide source, such as sodium azide, to form an acyl azide intermediate (not shown), which can undergo a Curtius rearrangement, as described in scheme E to afford the N-Boc cis-1,3-amino acid of type 45. The existing carboxylic acid moiety from compound 45 can be reacted under similar Curtius rearrangement conditions, as described in scheme E, to afford the N-CBz-protected amine (46). It should be noted that the stepwise route from cis-1,3-dicarboxylic acid, 43, facilitates a protecting group strategy that differentiates the amino groups in compound 46. Compound 46 can be subsequently elaborated to compounds of the present invention (I) as described in the subsequent schemes.

Scheme J

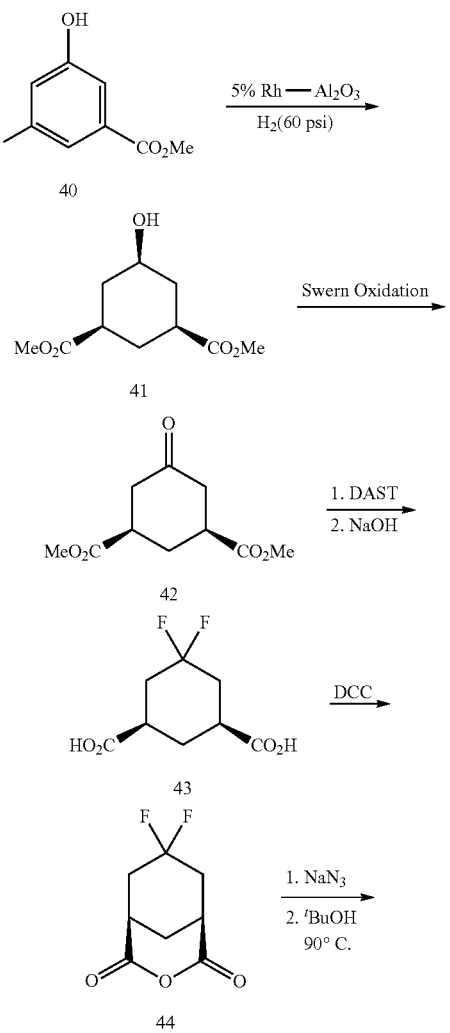

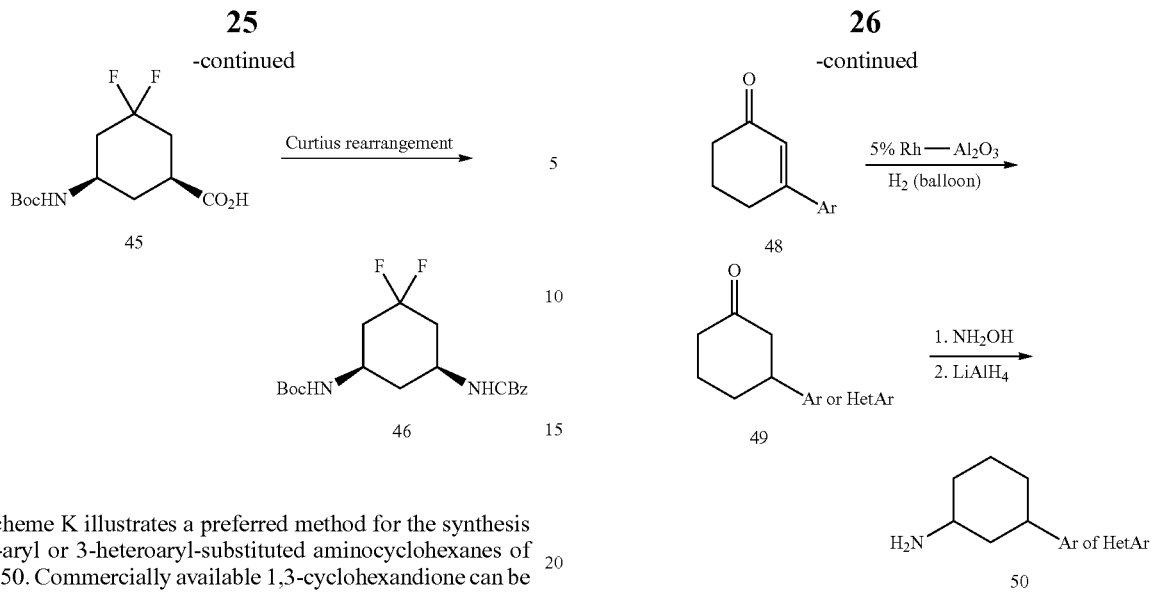

Scheme K illustrates a preferred method for the synthesis of 3-aryl or 3-heteroaryl-substituted aminocyclohexanes of type 50. Commercially available 1,3-cyclohexandione can be treated with a suitable electrophilic activating agent, such as oxalyl chloride or phosphorous oxychloride or the like, in an inert solvent, typically a halogenated solvent, such as DCM, at 0° C., over a period of from 1-24 h, yielding a vinyl chloride of type 47. It should be noted that additives, such as DMF, serve to accelerate the reaction by further activating the aforementioned electrophilic reagent. Vinyl chloride 47 can then be cross-coupled with boronic acids of type 4 or 4a, following procedures described previously for the Suzuki coupling reaction in scheme A to afford vinylogous ketones of type 48. Reduction of 48 to the corresponding cyclohexanone species, 49, involves hydrogenation, typically at atmospheric or balloon pressure, in the presence of a suitable catalyst, such as rhodium metal adsorbed onto alumina. The reaction is conducted in an inert solvent, such as EtOH, for 1-24 h. Ketone 49 is converted to the corresponding amine by reductive amination, following procedures known to those skilled in the art of organic synthesis. One preferred method for effecting the reductive amination involves a two-step process whereby the ketone (49) is first reacted with hydroxylamine in the presence of a suitable mild base, such as potassium carbonate or the like, in an aqueous methanolic solution to afford an oxime (not shown), that is subsequently reduced to amine 50 via treatment with a strong reducing agent, such as lithium aluminum hydride. The reduction is commonly performed in an ethereal solvent, such as THF or ether, typically at 0° C. for 1-24 h. The product of the reaction (50) can be elaborated to compounds of the present invention (I) as described in the subsequent schemes.

Scheme L illustrates preferred methods for the synthesis of compounds of type 52 and 54 via copper-catalyzed N-arylation by nucleophilic heterocycles, specifically pyrazoles of type 51, and imidazoles of type 53, respectively. Regarding the former product, 52, a preferred method follows from literature procedures (Cristaue, H-J, et al. *Eur. J. Org. Chem.* 2004, 695) wherein aryl halides of type 3a are reacted with unsubstituted or substituted pyrazoles of type 51 in the presence of a copper catalyst, such as copper (I) oxide. The reaction is accelerated via inclusion of a copper-coordinating ligand, such as salicylaldoxime, and is conducted in the presence of a suitable inorganic base, such as cesium carbonate, or potassium phosphate tribasic, or the like, in a variety of solvents, such as acetonitrile, toluene or DMF, at reaction temperatures ranging from 50° C. to the boiling point of the solvent, typically for 24-96 h. An alternative catalyst-ligand pair involves the application of a different copper (I) source, copper iodide, in the presence of a 1,2-diaminoalkane as demonstrated by Buchwald and co-workers (*J. Org. Chem.* 2004, 69, 5578). Performing the above reaction in a microwave reactor can further accelerate the reaction process. The product of the reaction, N-aryl pyrazoles of type 52 can be further elaborated to compounds of the present invention (I) as described in the subsequent schemes.

A preferred method for the N-arylation by imidazoles of type 53 follows procedures outlined in the aforementioned Buchwald publication. Therein, a preferred catalyst-ligand system involves copper iodide as the catalyst source, and 1,10-phenanthroline as the preferred ligand. The reactions are performed in the presence of a suitable inorganic base, such as those bases mentioned above, and is preferably conducted in dioxane or DMF, at temperatures greater than 100° C. for 24 h. A recent publication applies benzotriazole as a ligand paired with copper iodide to effect N-arylation by imidazoles (Verma, A. K. et al. *Tetrahedron Lett.* 2007, 48, 4207) under similar conditions to those described previously, with potassium tert-butoxide and DMSO reported to be the preferred inorganic base and solvent, respectively. The product of the reaction (54) can be further elaborated to compounds of the present invention (I) as described in the subsequent schemes.

Scheme K

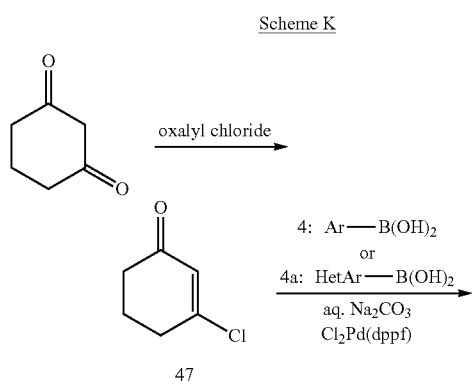

Scheme L

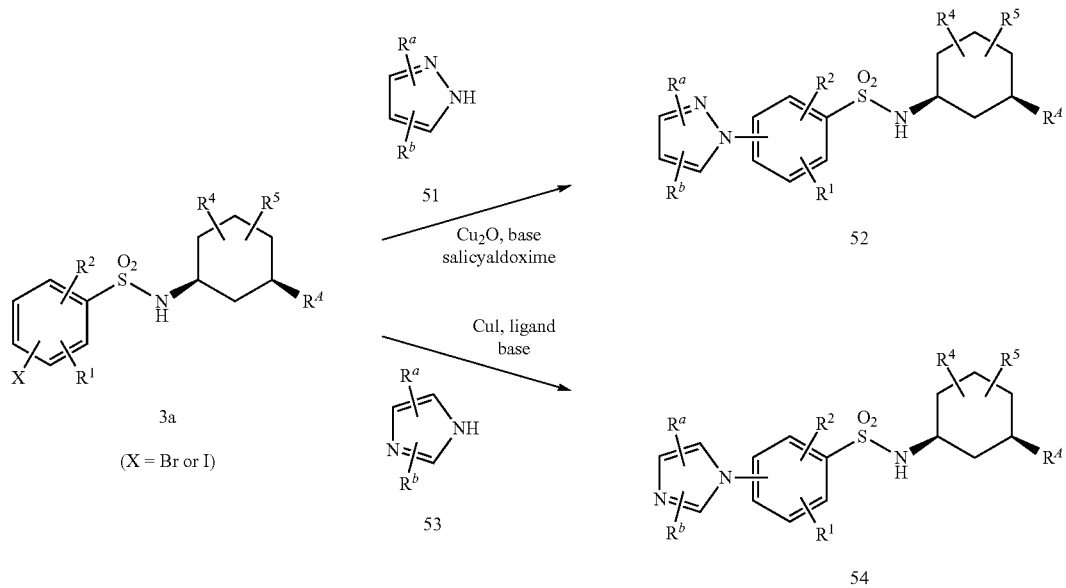

Scheme M illustrates the preferred method for the resolution of a racemic compound of structural formula 55 in which the asterisked carbon is a center of chirality. Generally, the latter, or intermediates en route to their preparation, may be resolved to afford enantiomerically pure compounds such as 56 and 57 by chiral stationary phase liquid chromatography techniques or other suitable methods known in organic synthesis.

The following examples are provided to illustrate the invention and are not to be construed as limiting the scope of the invention in any manner.

Preparation of Intermediates

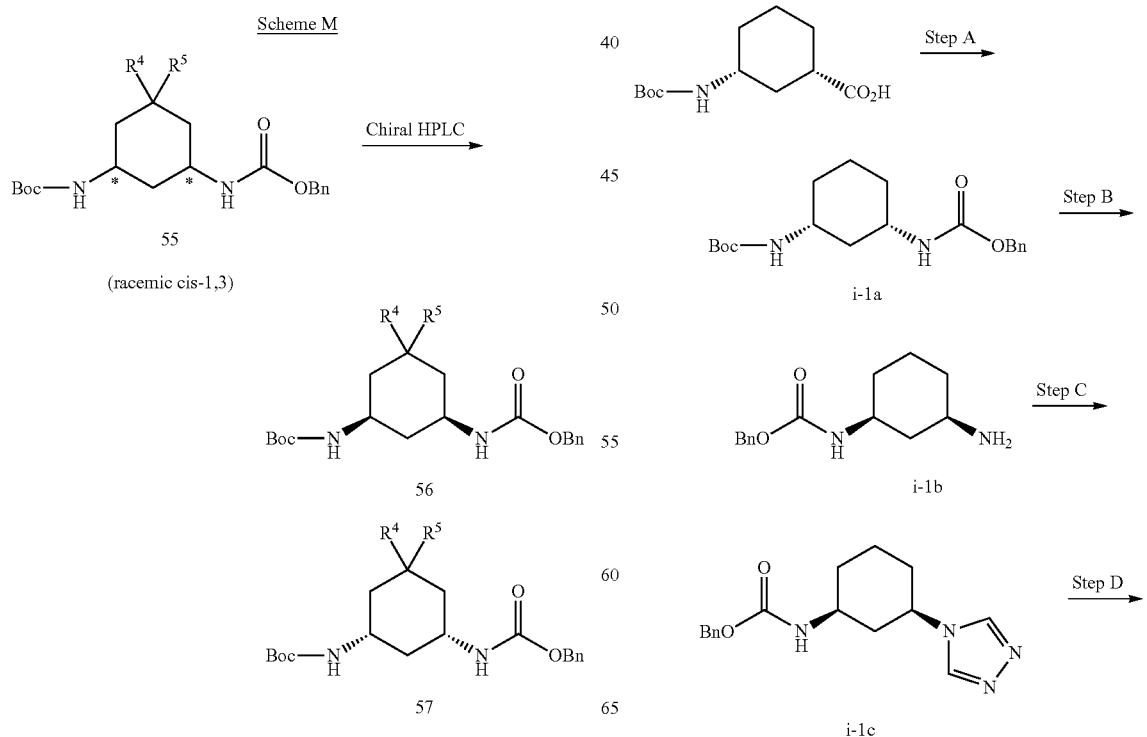

-continued

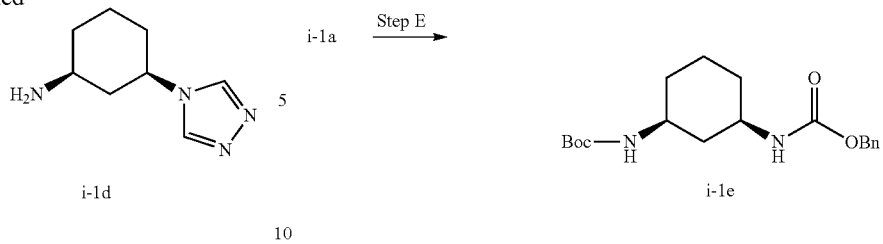

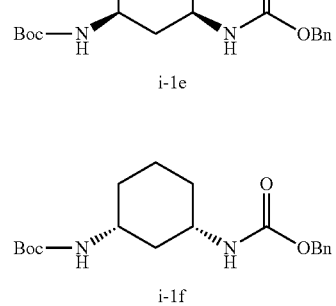

Step A: Preparation of benzyl tert-butyl cis-cyclohexane-1,3-diylbiscarbamate (i-1a)

Triethylamine (1.8 mL, 12.9 mmol) and diphenylphosphoryl azide (2.0 mL, 9.27 mmol) were added to a stirred solution of cis-3-[(tert-butoxycarbonyl)amino]cyclohexanecarboxylic acid (2.0 g, 8.22 mmol) in toluene (50 mL), and the resulting mixture was stirred at rt for 3 h. Benzyl alcohol (1.70 mL, 16.4 mmol) was added, and the mixture was heated to 100° C. After 12 h, the reaction mixture was cooled to rt, diluted with EtOAc, and the resulting mixture was washed with brine, dried (Na$_2$SO$_4$) and concentrated in vacuo. The crude residue was purified by flash chromatography on silica gel (gradient elution; 0-30% EtOAc/hexanes as eluent) to afford the title compound i-1a. m/z (ES) 371 (M+Na)$^+$

Step B: Preparation of benzyl cis-3-(aminocyclohexyl)carbamate (i-1b)

Compound i-1a (1.56 g, 4.48 mmol) was added to a stirred solution of acetyl chloride (5.0 mL, 70.3 mmol) in MeOH (50 mL), and the resulting mixture was stirred at rt for 12 h. The reaction mixture was concentrated in vacuo, redissolved in DCM, and ammonia (2.5 mL, 5.00 mmol, 2 M in MeOH) was added. The resulting mixture was stirred at rt for 20 min. and concentrated in vacuo to afford the title compound i-1b. m/z (ES) 249 (MH)$^+$

Step C: Preparation of benzyl[cis-3-(4H-1,2,4-triazol-4-yl)cyclohexyl]carbamate (i-1c)

N,N-Dimethyl formamide azine (777 mg, 5.46 mmol) and p-TSA monohydrate (0.170 g, 0.894 mmol) were added to a stirred solution of i-1b (1.11 g, 4.47 mmol) in toluene (30 mL), and the resulting mixture was heated to 100° C. After 48 h, the reaction mixture was cooled to rt, concentrated in vacuo, and the resulting crude residue was purified by flash chromatography on silica gel (gradient elution; 2-10% MeOH/DCM as eluent) to afford the title compound i-1c. m/z (ES) 301 (MH)$^+$

Step D: Preparation of cis-3-(4H-1,2,4-triazol-4-yl)cyclohexanamine (i-1d)

Palladium hydroxide (124 mg, 0.177 mmol, 20 wt. % on activated carbon) was added to a stirred solution of i-1c (1.34 g, 4.47 mmol) in MeOH (10 mL), and the resulting mixture was hydrogenated at atmospheric pressure. After 3 h, the reaction mixture was filtered through a short column of Celite®, eluting copiously with EtOAc. The filtrate was concentrated in vacuo to afford the title compound i-1d. m/z (ES) 167 (MH)$^+$

Step E: Preparation of i-1e and i-1f

Enantiomers i-1e and i-1f were separated using preparative supercritical fluid chromatography. A solution of i-1a in methanol was injected onto a Chiralcel® OD (available from Chiral Technologies, Inc., Exton, Pa.) semi-preparative (250× 20 mm) HPLC column (eluting with 20% isopropanol/heptane at 5 mL/min, with UV detection at 220 nm). The enantiomers were separated to yield a faster eluting enantiomer i-1e (Chiralcel® OD, 20% isopropanol/heptane at 1 mL/min, rt, detection at 220 nm, retention time=7.02 min) and a slower eluting enantiomer i-1f (Chiralcel® OD, 20% isopropanol/heptane at 1 mL/min, rt, detection at 220 nm, retention time=9.70 min). The respective fractions were concentrated to provide the enantiomers i-1e and i-1f.

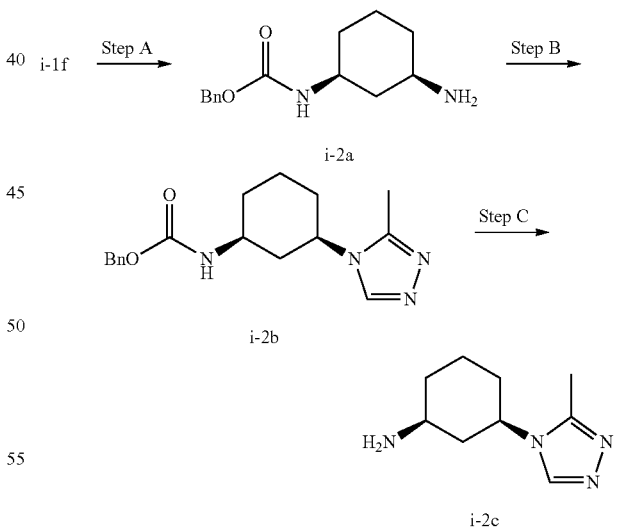

Step A: Preparation of benzyl[(1S,3R)-3-aminocyclohexyl]carbamate (i-2a)

Compound i-2a was prepared from i-1f following procedures similar to those as described in Scheme i-1, step B, substituting i-1f for i-1a. m/z (ES) 289 (MH)$^+$

Step B: Preparation of benzyl[(1S,3R)-3-(3-methyl-4H-1,2,4-triazol-4-yl)cyclohexyl]carbamate (i-2b)

DMF-DMA (357 mg, 3.00 mmol) was added to a stirred mixture of acetyl hydrazide (222 mg, 3.00 mmol) in DCM (2.00 mL), and the resulting mixture was heated to 40° C. After 1 h, the reaction mixture was concentrated in vacuo to afford a light yellow solid, which was combined with i-2a (693 mg, 2.79 mmol) and AcOH (2.00 mL) in a sealed tube and heated in a microwave reactor at 150° C. for 5 min. After cooling to rt, the reaction mixture was concentrated in vacuo, and the resulting crude residue was purified by column chromatography on silica gel (gradient elution, 0-10% MeOH/DCM as eluent) to afford the title compound, i-2b. m/z (ES) 315 (MH)$^+$

Step C: Preparation of (1S,3R)-3-(3-methyl-4H-1,2,4-triazol-4-yl)cyclohexanamine (i-2c)

Compound i-2c was prepared following procedures as described for the preparation of compound i-1d, substituting i-2b for i-1c. $^1$HNMR (500 MHz, CD$_3$OD) δ 8.56 (s, 1H), 4.17 (tt, 1H-1, J=4.0, 12.0 Hz), 3.08 (tt, 1H, J=4.0, 11.5 Hz), 2.67 (d, 1H, J=13.5 Hz), 1.97-2.07 (m, 3H), 1.90 (s, 3H), 1.54-1.73 (m, 3H), 1.30 (m, 1H).

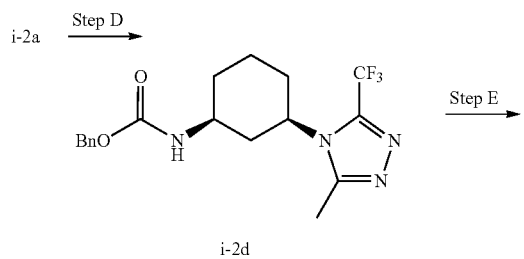

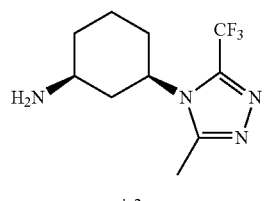

Step D: Preparation of benzyl {(1S,3R)-3-[3-methyl-5-(trifluoromethyl)-4H-1,2,4-triazol-4-yl]cyclohexyl}carbamate (i-2d)

Compound i-2a (128 mg, 0.515 mmol) was added to a stirred solution of trimethylorthoacetate (2.47 g, 20.6 mmol) and pyridinium p-toluenesulfonate (1.9 mg, 7.7 µmol) in EtOH (5.0 mL), and the resulting mixture was heated to 80° C. After 2 h, the reaction mixture was cooled to rt and concentrated in vacuo. Trifluoroacetic hydrazide (66.0 mg, 0.515 mmol) and acetic acid (2.0 mL) were added to the crude residue, and the resulting mixture was heated to 80° C. After 3 h, the reaction mixture was concentrated in vacuo, and the resulting crude residue was partitioned between EtOAc and satd, aq. NaHCO$_3$. The layers were separated, and the organics were washed with brine, dried (Na$_2$SO$_4$), filtered and concentrated in vacuo. The crude residue was purified by column chromatography on silica gel (gradient elution, 0-10% MeOH/DCM as eluent) to afford the title compound, i-2d. m/z (ES) 383 (MH)$^+$

Step E: Preparation of (1S,3R)-3-[3-methyl-5-(trifluoromethyl)-4H-1,2,4-triazol-4-yl]cyclohexanamine (i-2e)

Compound i-2e was prepared following procedures as described for the preparation of compound i-1d, substituting i-2d for i-1c. m/z (ES) 249 (MH)$^+$

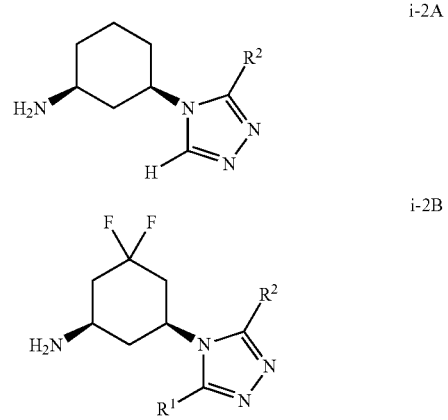

Following procedures similar to those described above in Scheme i-2, steps B and C, the intermediates in Table i-2 were prepared:

| i-2A | i-2B | R$^1$ | R$^2$ |
|---|---|---|---|
| a | a | H | H |
| — | b | H | Me |
| c | c | H | $^c$Pr |
| d | d | H | CF$_3$ |
| — | e | Me | CF$_3$ | i-2Aa: (1S,3R)-3-(4H-1,2,4-triazol-4-yl)cyclohexanamine; m/z (ES) 167 (MH)$^+$ i-2Ac: (1S,3R)-3-(3-cyclopropyl-4H-1,2,4-triazol-4-yl)cyclohexanamine; m/z (ES) 207 (MH)$^+$ i-2Ad: (1S,3R)-3-[3-(trifluoromethyl)-4H-1,2,4-triazol-4-yl]cyclohexanamine; m/z (ES) 235 (MH)$^+$ i-2Ba: (1R,5S)-3,3-difluoro-5-(4H-1,2,4-triazol-4-yl)cyclohexanamine; m/z (ES) 203 (MH)$^+$ i-2Bb: (1R,5S)-3,3-difluoro-5-(3-methyl-4H-1,2,4-triazol-4-yl)cyclohexanamine; m/z (ES) 217 (MH)$^+$

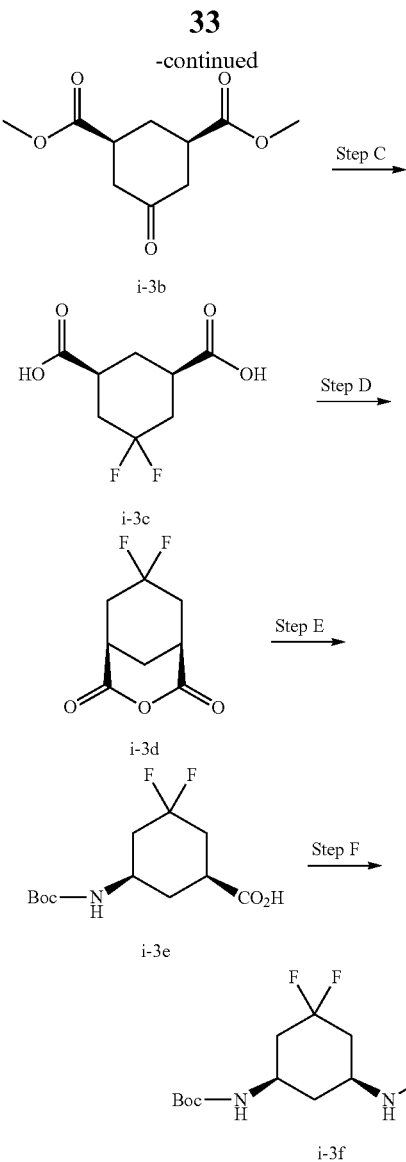

Step A: Preparation of dimethyl syn-5-hydroxycyclohexane-cis-1,3-dicarboxylate (i-3a)

A mixture of dimethyl-5-hydroxyisophthalate (25.5 g, 121 mmol) and rhodium (4.48 g, 43.5 mmol, 5 wt. % on alumina) in MeOH was pressurized to 60 psi in a Parr reactor and shaken for 72 h. The reaction mixture was filtered through a short column of Celite®, eluting copiously with MeOH and concentrated in vacuo to afford the title compound i-3a. m/z (ES) 217 (MH)$^+$

Step B: Preparation of dimethyl 5-oxo-cyclohexane-cis-1,3-dicarboxylate (i-3b)

A solution of DMSO (91.0 mL, 1.20 mol) in DCM (320 mL) was added dropwise to a stirred solution of oxalyl chloride (80.0 g, 0.64 mmol) in DCM (330 mL) at −60° C., such that the internal temperature did not rise above −50° C. After 45 min., a solution of i-3a (46.0 g, 0.213 mol) in DCM (220 mL) was added carefully such that the internal temperature was maintained. After 1 h, triethylamine (296 mL, 2.13 mol) was added slowly. After an additional 2 h, ice and water are added with vigorous stirring and the resulting layers were separated. The combined organics were washed with 2M HCl and brine, dried (MgSO$_4$), filtered and concentrated in vacuo. The crude residue was triturated with ether and filtered to afford title compound i-3b. m/z (ES) 215 (MH)$^+$

Step C: Preparation of 5,5-difluorocyclohexane-cis-1,3-dicarboxylic acid (i-3c)

DAST (21.0 mL, 160 mmol) was added slowly to a stirred solution of i-3b (13.7 g, 64.0 mmol) in 1,2-dichloroethane (250 mL) in a polyethylene screw capped vessel at 0° C., and the resulting mixture was heated to 60° C. After 2 h, the reaction mixture was cooled to 0° C., poured into satd. aq. NaHCO$_3$, and extracted with DCM. The combined organics were washed with brine, dried (MgSO$_4$) and concentrated in vacuo. The crude residue was purified by flash chromatography (gradient elution; 5-25% EtOAc/Hexanes as eluent) to afford an intermediate product that was reacted with NaOH (256 mmol) in MeOH/H$_2$O (500 mL of a 1:3 mixture, respectively) at rt for 2 h. The mixture was acidified to pH=3, partially concentrated in vacuo and filtered. The filter cake was washed with ice water and dried to afford the title compound i-3c. m/z (ES) 209 (MH)$^+$

Step D: Preparation of 7,7-difluoro-3-oxabicyclo[3.3.1]nonane-2,4-dione) (i-3d)

DCC (8.50 g, 41.2 mmol) in DCM (20 mL) was added slowly to a stirred solution of i-3c (8.50 g, 43 mmol) in DCM (60 mL) at 0° C., and the resulting mixture was allowed to warm to rt and stirred overnight. The reaction mixture was filtered, and the filter cake was washed with cold DCM. The combined organic filtrate was concentrated in vacuo, and the resulting crude residue crystallized to afford the title compound i-3d. m/z (ES) 191 (MH)$^+$. $^1$HNMR (500 MHz, CDCl$_3$) δ 3.30 (dd, 2H, J=2.0, 5.0 Hz), 2.63 (t, 2H, J=14.0 Hz), 2.37 (m, 1H), 2.28. (m, 1H), 2.25 (m, 1H), 1.89 (d, 1H, J=14.0 Hz).

Step E: Preparation of Cis-(1,5)-5-[(tert-butoxycarbonyl)amino]-3,3-difluorocyclohexanecarboxylic acid (i-3e)

A solution of sodium azide (4.99 g, 77.0 mmol) in water (40 mL) was added dropwise to a stirred mixture of i-3d (7.30 g, 38.4 mmol) in acetone (150 mL) at 0° C. The resulting mixture was stirred at 0° C. for 2 h, then warmed to rt. The reaction mixture was partially concentrated in vacuo, and the resulting aq. layer was cooled to 0° C., diluted with DCM and acidified to pH~3. The layers were separated and the aq. layer was extracted with DCM. The combined organics were dried (MgSO$_4$) and concentrated in vacuo to afford a pale yellow oil, to which was added tert-butyl alcohol (12.5 mL, 130 mmol) and toluene (150 mL), and the resulting mixture was heated to 90° C. overnight. After cooling to rt, the reaction mixture was concentrated in vacuo, diluted with ether/DCM, and filtered through a short column of Celite®, eluting copiously with ether/DCM. The filtrate was concentrated in vacuo to afford the title compound i-3e. m/z (ES) 280 (MH)$^+$

Step F: Preparation of benzyl tort-butyl (5,5-difluorocyclohexane-cis-1,3-diyl)biscarbamate (i-3f)

Ethyl chloroformate (2.75 mL, 28.6 mmol) and methylmorpholine (3.15 mL, 28.6 mmol) were added to a stirred solution of i-3e (8.00 g, 28.6 mmol) in THF (100 mL) at −20° C. After stirring at −20° C. for 30 min, the reaction mixture was warmed to −5° C., at which point, a solution of sodium azide (7.45 g, 115 mmol) in water (10 mL) was added. The resulting mixture was stirred at −5° C. for an additional 10 min, diluted with EtOAc, washed with brine, dried (MgSO$_4$) and concentrated in vacuo. The crude residue was added to a stirred solution of benzyl alcohol (5.96 mL, 57.3 mmol) in toluene (100 mL), and the resulting mixture was heated to 90° C. overnight. After cooling to rt, the crude residue was purified by column chromatography on silica gel (gradient elution, 0-20% EtOAc/hexanes as eluent) to afford the title compound i-3f. m/z (ES) 285 [(M+H)-BOC]. $^1$HNMR (500 MHz, CD$_3$OD) δ 7.29-7.34 (m, 5H), 5.07 (s, 2H), 3.55 (m, 2H), 2.29 (m, 2H), 2.14 (d, 1H, J=11.0 Hz), 1.56-1.71 (m, 2H), 1.24 (bq, J=12 Hz, 1H).

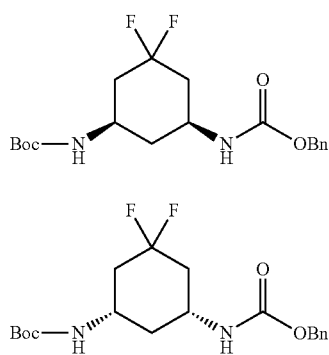

i-3g i-3h

Enantiomers i-3g and i-3h were separated using preparative supercritical fluid chromatography. A solution of i-3f in methanol was injected onto a Chiralpak® OD (available from Chiral Technologies, Inc., Exton, Pa.) semi-preparative (250× 20 mm) HPLC column (eluting with 20% isopropanol/CO$_2$ at 50 mL/min, 100 bar outlet pressure with UV detection at 220 nm). The enantiomers were separated to yield a faster eluting enantiomer i-3g (Chiralpak® OD, 250×4.6 mm, 20% isopropanol/CO$_2$ at 2.1 mL/min, 40° C., detection at 220 nm, retention time=5.08 min) and a slower eluting enantiomer i-3h (Chiralpak® OD, 250×4.6 mm, 20% isopropanol/CO$_2$ at 2.1 mL/min, 40° C., detection at 220 nm, retention time=6.80 min). The respective fractions were concentrated to provide the enantiomers i-3g and i-3h.

Scheme i-4

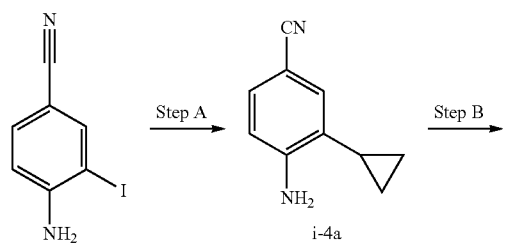

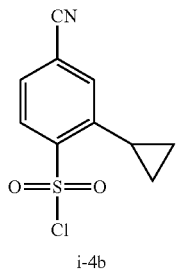

i-4b

Step A: Preparation of 4-amino-3-cyclopropylbenzonitrile (i-4a)

Palladium (II) acetate (798 mg, 3.55 mmol) was added to a stirred mixture of 4-amino-3-iodobenzonitrile (5.08 g, 20.8 mmol), cyclopropyl boronic acid (2.69 g, 31.3 mmol), potassium phosphate (22.9 g, 108 mmol) and tricyclohexylphosphine (1.17 g, 4.17 mmol) in toluene (40 mL)/water (2 mL). The reaction mixture was degassed and heated to 100° C. for 3 h. After cooling to rt, the reaction mixture was poured into water and extracted with EtOAc. The combined organics were washed with brine, dried (Na$_2$SO$_4$) and concentrated in vacuo. The crude residue was purified by column chromatography on silica gel (gradient elution; 0-20% EtOAc/hexanes as eluent) to afford the title compound i-4-a. m/z (ES) 159 (MH)$^+$ Step B: Preparation of 4-cyano-2-cyclopropylbenzenesulfonyl chloride (i-4-b)

An aqueous sodium nitrite solution (5.0 mL of a 4.0 M solution) was added to a stirred solution of i-4-a (1.64 g, 10.37 mmol) in AcOH (5 mL) and conc. hydrochloric acid (20 mL) at −10° C. After 45 min, the reaction was poured into an SO$_2$-saturated solution of copper (II) chloride (1.67 g, 12.4 mmol) in AcOH (30 mL) at 0° C. After 10 min, the reaction mixture was warmed to rt and allowed to stir for 3 h, at which time, the reaction was poured into an ice-water mixture and extracted w/EtOAc. The combined organics were washed with brine, dried (Na$_2$SO$_4$) and concentrated in vacuo. The crude residue was purified by column chromatography on silica gel (gradient elution, 0-15% EtOAc/hexanes as eluent) to afford the title compound i-4b. $^1$HNMR (500 MHz, CDCl$_3$): δ 8.17 (d, 1H, J=3.5 Hz), 7.66 (dd, 1H, J=1.5, 3.5 Hz), 7.39 (d, 1H, J=1.5 Hz), 2.82 (m, 1H), 1.34 (m, 2H), 1.00 (m, 2H).

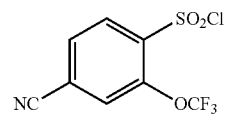

i-4c

Preparation of 4-cyano-2-(trifluoromethoxy)benzenesulfonyl chloride (i-4-c)

Compound i-4-c was prepared following procedures similar to those described above, substituting 4-amino-3-(trifluoromethoxy)benzonitrile for 4-amino-3-iodobenzonitrile.

Scheme i-5

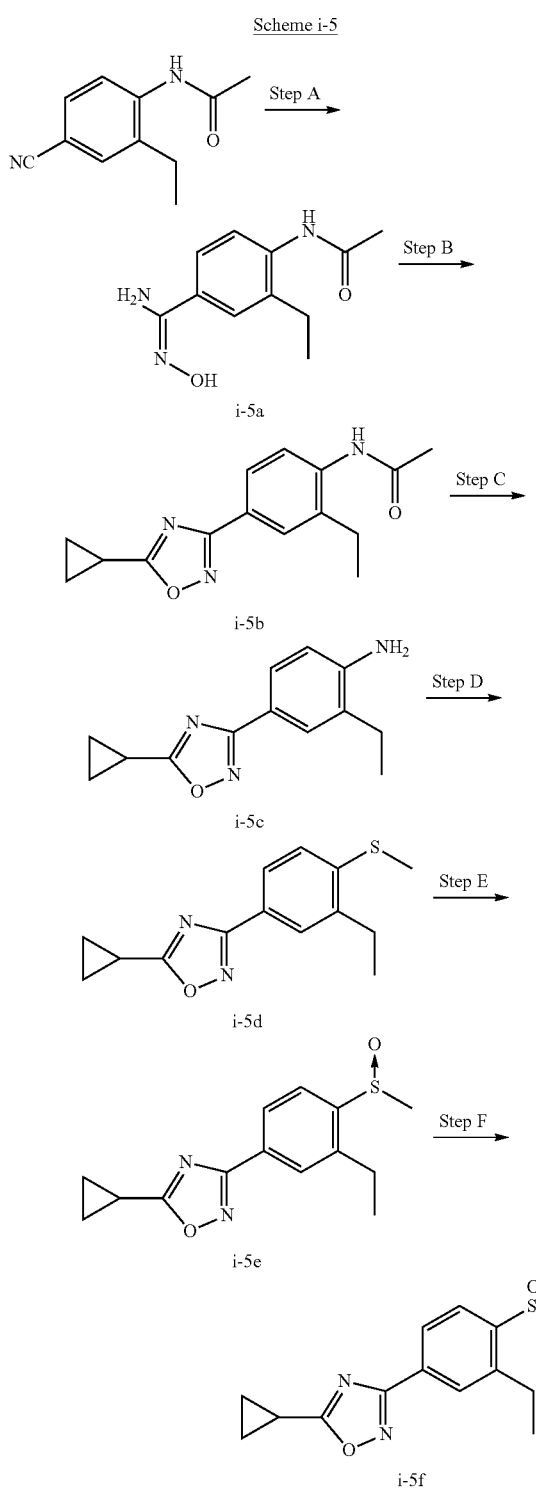

Step A: Preparation of N-{4-[(E)-amino(hydroxyimino)methyl]-2-ethylphenyl}acetamide (i-5a)

Hydroxylamine (5.95 g, 90.0 mmol, 50 wt. % aq. solution) was added to a stirred solution of N-(4-cyano-2-ethylphenyl)acetamide (5.65 g, 30.0 mmol) in EtOH (70 mL), and the resulting mixture was heated to 90° C. After 2 h, the reaction mixture was cooled to rt and concentrated in vacuo to afford the title compound i-5a. m/z (ES) 222 (MH)+

Step B: Preparation of 4-(5-cyclopropyl-1,2,4-oxadiazol-3-yl)-2-ethylanilide (i-5b).

Cyclopropanecarbonyl chloride (3.76 g, 36.0 mmol) was added to a stirred suspension of i-5a (6.64 g, 30.0 mmol) and triethylamine (5.0 mL, 36.0 mmol) in DCM (200 mL) at 0° C., and the resulting mixture was warmed slowly to rt. After 2 h, the reaction mixture was concentrated in vacuo, and the crude residue was dissolved in toluene (200 mL). Molecular sieves were added, and the resulting mixture was heated to reflux overnight. After cooling to rt, the mixture was filtered, and the resulting filtrate was concentrated in vacuo and purified by column chromatography on silica gel (gradient elution, 0-60% EtOAc/hexanes as eluent) to afford the title compound i-5b. m/z (ES) 272 (MH)+

Step C: Preparation of 4-(5-cyclopropyl-1,2,4-oxadiazol-3-yl)-2-ethylaniline (i-5c)

6N HCl (40 mL, 240 mmol) was added to a stirred solution of i-5b (3.57 g, 13.2 mmol) in MeOH (40 mL), and the resulting mixture was heated to 80° C. After 2 h, the reaction mixture was cooled to rt and concentrated in vacuo. The crude residue was diluted with EtOAc, washed with said. aq. NaHCO₃, dried (MgSO₄), and concentrated in vacuo to afford the title compound i-5c. m/z (ES) 230 (MH)+

Step D: Preparation of 5-cyclopropyl-3-[3-ethyl-4-(methylthio)phenyl]-1,2,4-oxadiazole (i-5d)

Copper powder (26.0 mg, 0.411 mmol) was added to a stirred solution of i-5c (3.14 g, 13.7 mmol) and methyl disulfide (25.8 g, 274 mmol), and the resulting mixture was stirred at rt. After 45 min, isoamyl nitrite (1.94 mL, 14.4 mmol) was added dropwise, and the reaction mixture was heated to 60° C. After 1 h, the reaction mixture was cooled to 0° C. and acidified with conc. HCl. The mixture was diluted with water and extracted with EtOAc. The combined organics were washed with brine, dried (MgSO₄), and concentrated in vacuo. The crude residue was purified by column chromatography on silica gel (gradient elution, 0-20% EtOAc/hexanes as eluent) to afford the title compound i-5d. m/z (ES) 261 (MH)+

Step E: Preparation of 5-cyclopropyl-3-[3-ethyl-4-(methylsulfinyl)phenyl]-1,2,4-oxadiazole (i-5e)

mCPBA (3.00 g, 13.1 mmol) was added to a stirred solution of i-5d (3.40 g, 13.1 mmol) in CHCl₃ (60 mL) at 0° C., and the resulting mixture was warmed to rt. After 30 min, the reaction mixture was cooled to 0° C., and calcium hydroxide (1.36 g, 18.3 mmol) was added. After an additional 30 min, the reaction mixture was filtered, and the filtrate was concentrated in vacuo to afford the title compound i-5e. m/z (ES) 277 (MH)+

Step F: Preparation of 4-(5-cyclopropyl-1,2,4-oxadiazol-3-yl)-2-ethylbenzenesulfonyl chloride (i-5f)

Trifluoroacetic anhydride (8.8 mL, 62.2 mmol) was added to a stirred solution of i-5e (4.3 g, 15.6 mmol) in DCM (60 mL), and the resulting mixture was heated to 40° C. After 1 h, the reaction mixture was cooled to rt, and concentrated in vacuo. The crude residue was partitioned into DCM/water (90 mL of a 5:1 mixture, respectively), and cooled to 0° C. The solution was purged with a stream of nitrogen for 30 min, at which time, AcOH (15 mL) was added, and chlorine gas was bubbled through for 20 min, followed by a nitrogen purge, as previously described. The reaction mixture was quenched with ice and extracted with ether. The combined organics were washed with satd. aq. NaHCO$_3$ and brine, dried (MgSO$_4$), and concentrated in vacuo. The crude residue was purified by column chromatography on silica gel (gradient elution, 0-5% EtOAc/hexanes as eluent) to afford the title compound i-5f. m/z (ES) 314 (MH)$^+$. $^1$HNMR (500 MHz, CDCl$_3$): δ 8.18 (m, 2H), 8.09 (dd, 1H, J=1.1, 7.0 Hz), 3.28 (q, 2H, J=7.7 Hz), 2.32 (m, 1H), 1.45 (t, 3H, J=7.7 Hz), 1.33-1.39 (m, 4H).

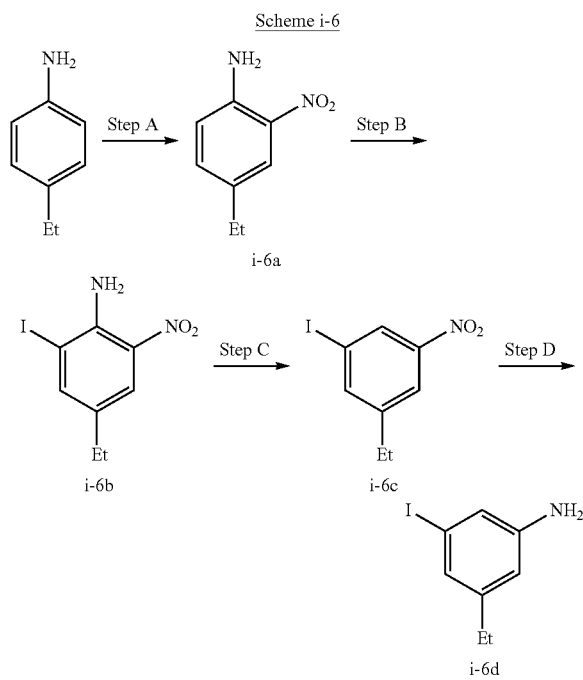

Step A: Preparation of 4-ethyl-2-nitroaniline (i-6a)

4-Ethylaniline (15.0 g, 124 mmol) was carefully added to acetic anhydride (100 mL, 1.06 mol) that was pre-cooled to 0° C., and the mixture was warmed to rt over 30 min, then recooled to 0° C., and nitric acid (7.90 mL of a 70% v/v aq. solution, 124 mL) was added dropwise. After 30 min, the reaction mixture was quenched into an ice-water bath, the resulting slurry was filtered, and the filter cake was dried in vacuo. The crude solid product was dissolved in 6M HCl (100 mL) and dioxane (60 mL), and the resulting mixture was heated at 0° C. After 3 h, the reaction mixture was cooled to rt and concentrated in vacuo. The crude residue was suspended in EtOAc and neutralized via addition of 6N NaOH. The layers were separated, and the aq. layer was extracted with EtOAc. The combined organics were washed with brine, dried (Na$_2$SO$_4$), filtered and concentrated in vacuo to afford the title compound, i-6a, m/z (ES) 167 (MH)$^+$.

Step B: Preparation of 4-ethyl-2-iodo-6-nitroaniline (i-6b)

Compound i-6a (7.00 g, 42.1 mmol) was added to a stirred solution of iodine (10.7 g, 42.1 mmol) and silver sulfate (13.1 g, 42.1 mmol) in EtOH (150 mL), and the resulting mixture was allowed to stir at rt. After 90 min, the reaction mixture was filtered through a short column of Celite®, eluting copiously with EtOH. The organics were concentrated in vacuo, and the crude residue was partitioned between EtOAc and 1N NaOH. The layers were separated, and the organics were washed with brine, dried (MgSO$_4$), filtered and concentrated in vacuo. The resulting crude residue was purified by column chromatography on silica gel (gradient elution, 0-25% EtOAc/hexanes as eluent) to afford the title compound i-6b. m/z (ES) 293 (MH)$^+$.

Step C: Preparation of 1-ethyl-3-iodo-5-nitrobenzene (i-6c)

A mixture of compound i-6b (3.00 g, 10.3 mmol) in DMF (20.0 mL) was added dropwise to a stirred solution of tert-butyl nitrite (1.34 mL, 11.3 mmol) in DMF (40.0 mL), and the resulting mixture was heated to 50° C. After 3 h, the reaction mixture was cooled to rt, quenched into pre-cooled 6M HCl and extracted with ether. The combined organics were washed with brine, dried (MgSO$_4$), filtered and concentrated in vacuo. The crude residue was purified by column chromatography on silica gel (gradient elution, 0-30% DCM/hexanes as eluent) to afford the title compound i-6c. $^1$H NMR (500 MHz, CDCl$_3$) δ 8.40 (s, 1H), 8.05 (s, 1H), 7.89 (s, 1H), 2.75 (q, 2H, J=7.5 Hz), 1.31 (t, 3H, J=7.5 Hz).

Step D: Preparation of 3-ethyl-5-iodoaniline (i-6d)

Iron metal (18.5 g, 332 mmol) was added in several portions to a stirred solution of i-6c (4.60 g, 16.6 mmol) and conc. HCl (4.09 mL of a 37% w/v aq. solution, 49.8 mmol) in MeOH (100 mL), and the resulting mixture was heated to 70° C. After the reaction was deemed to be complete, the reaction mixture was cooled to rt, filtered through a short column of Celite®, eluting copiously with MeOH. The combined organics were concentrated in vacuo, and the crude residue was partitioned between DCM and satd. aq. NaHCO$_3$. The layers were separated, and the organics were washed with brine, dried (MgSO$_4$), filtered and concentrated in vacuo. The crude residue was purified by column chromatography on silica gel (gradient elution, 0-40% DCM/hexanes as eluent) to afford the title compound, i-6d. ln/z (ES) 248 (MH)$^+$.

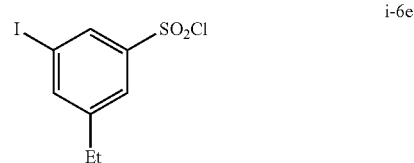 [SMILES: CCc1cc(I)cc(S(=O)(=O)Cl)c1]

Preparation of 3-ethyl-5-iodobenzenesulfonyl chloride (i-6e)

Compound i-6e was prepared following procedures similar to those described in Scheme i-5, steps D through F, initially substituting i-6d for i-5c. $^1$HNMR (500 MHz, CDCl$_3$) δ 8.10 (s, 1H), 7.93 (s, 1H), 7.85 (s, 1H), 2.75 (m, 2H), 1.33 (m, 3H).

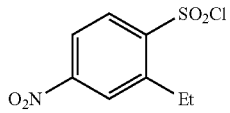

Preparation of 2-ethyl-4-nitrobenzenesulfonyl chloride (i-6f)

Compound i-6f was prepared following procedures similar to those described for the preparation of compound i-6a, substituting 2-ethylaniline for 4-ethylaniline. The product of that reaction was converted to i-6f following procedures similar to those previously described in Scheme i-6, step D, with the product of that reaction subjected to conditions previously described in Scheme i-5, steps D through F, to afford the title compound, i-6f. $^1$HNMR (500 MHz, CDCl$_3$) δ 8.36 (d, 1H, J=2.1 Hz), 8.30 (d, 1H, J=9.0 Hz), 8.25 (dd, 1H, J=2.3, 8.7 Hz), 3.34 (q, 2H, J=7.5 Hz), 1.47 (t, 3H, J=7.5 Hz).

Scheme i-7

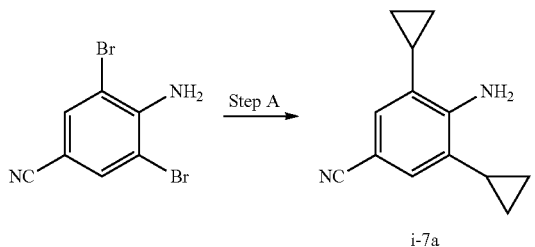

Step A: Preparation of 4-amino-3,5-dicyclopropylbenzonitrile (i-7a)

Palladium (II) acetate (814 mg, 3.62 mmol) was added to a stirred mixture of 4-amino-3,5-dibromobenzonitrile (5.00 g, 18.1 mmol), cyclopropanboronic acid (3.89 g, 45.3 mmol), potassium phosphate tribasic (23.1 g, 109 mmol) and tricyclohexylphosphine (1.02 g, 3.62 mmol) in toluene (20.0 mL) and water (1.0 mL). The resulting mixture was degassed and heated to 100° C. After 3 h, the reaction mixture was cooled to rt, diluted with water and extracted with EtOAc. The organics were washed with brine, dried (Na$_2$SO$_4$), filtered and concentrated in vacuo. The crude residue was purified by column chromatography on silica gel (gradient elution, 0-15% EtOAc/hexanes as eluent) to afford the title compound i-7a. m/z (ES) 199 (MH)$^+$.

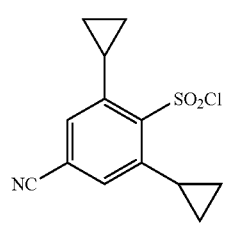

Preparation of 4-cyano-2,6-dicyclopropylbenzenesulfonyl chloride (i-7b)

Compound i-7b was prepared following procedures similar to those described in Scheme i-5, steps D through F, substituting i-7a for i-5c.

Preparation of Examples

Example 1

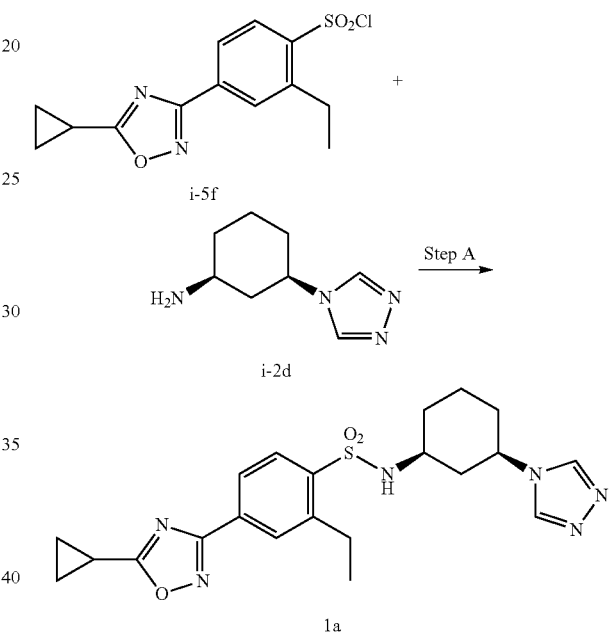

Preparation of 4-(5-cyclopropyl-1,2,4-oxadiazol-3-yl)-2-ethyl-N-[(1S,3R)-3-(4H-1,2,4-triazol-4-yl)cyclohexyl]benzenesulfnamide (1a)

Compound i-5f (580 mg, 1.85 mmol) was added to a stirred solution of i-2d (308 mg, 1.85 mmol) and triethylamine (362 μL, 2.60 mmol) in DCM (15 mL), and the resulting mixture was stirred at rt overnight. The reaction was quenched by the addition of said. aq. NH$_4$Cl and extracted with DCM. The combined organics were washed with brine, dried (MgSO$_4$) and concentrated in vacuo. The crude residue was purified by column chromatography on silica gel (gradient elution, 0-10% MeOH/DCM as eluent) to afford the title compound 1a. m/z (ES) 443 (MH)$^+$. $^1$HNMR (500 MHz, CD$_3$OD) δ 8.56 (s, 2H), 8.09 (d, 1H, J=10.0 Hz), 7.98 (d, 1H, J=10.0 Hz), 4.26 (tt, 1H, J=4.0, 10.0 Hz), 3.30 (m, 1H), 3.14 (q, 2H, J=7.5 Hz), 2.36 (m, 1H), 2.27 (m, 1H), 2.05 (m, 1H), 1.83 (m, 2H), 1.70 (q, 1H, J=11.0 Hz), 1.63 (dq, 1H, J=2.0, 11.0 Hz), 1.36 (t, 3H, J=7.5 Hz), 1.26-1.46 (m, 6H).

Example 2

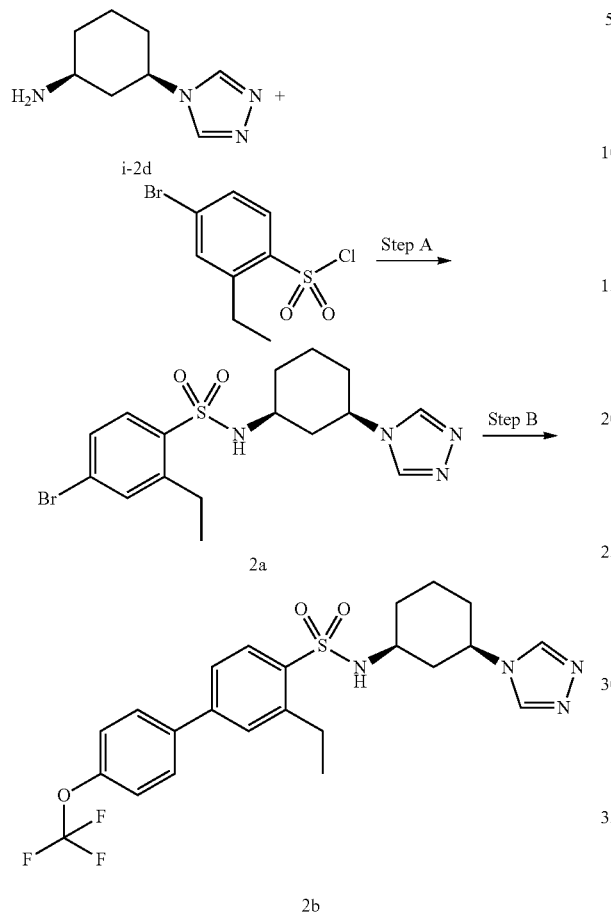

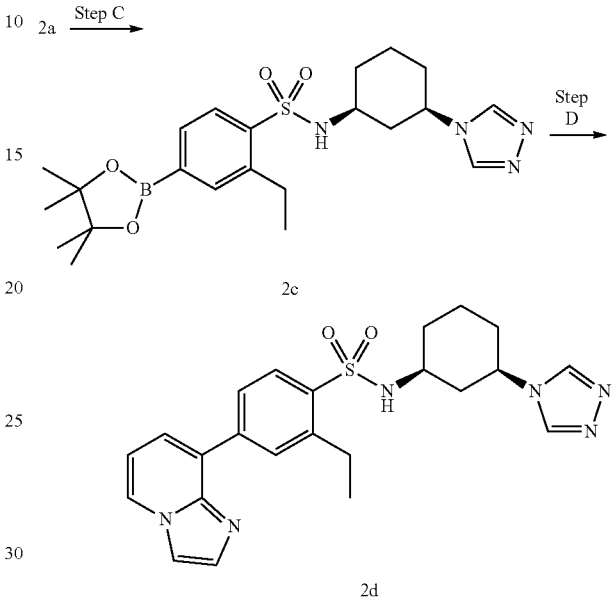

Step A: Preparation of 4-bromo-2-ethyl-N-[(1S,3R)-3-(4H-1,2,4-triazol-4-yl)cyclohexyl]benzenesulfonamide (2a)

Compound 2a was prepared following procedures similar to those as described in Example 1, Step A, substituting 4-bromo-2-ethylbenzene-1-sulfonyl chloride for i-5f. m/z (ES) 413 (MH)$^+$.

Step B: Preparation of 3-ethyl-N-[(1S,3R)-3-(4H-1,2,4-triazol-4-yl)cyclohexyl]-4'-(trifluoromethoxy)biphenyl-4-sulfonamide (2b)

[1,1'-bis(diphenylphosphino)ferrocene]dichloropalladium (336 mg, 0.411 mmol) was added to a stirred solution of 4-(trifluoromethoxy)phenylboronic acid (1.27 g, 6.17 mmol), 2a (1.70 g, 4.11 mmol) and sodium carbonate (5.14 mL of a 2.0 M aqueous solution) in ethanol (32.0 mL) and toluene (8.0 mL). The resulting mixture was degassed and heated to 90° C. After 3 h, the reaction mixture was cooled to rt and filtered through a short column of Celite, eluting copiously with EtOH. The combined organics were concentrated in vacuo, and the crude residue was purified by column chromatography on silica gel (gradient elution, 1-9% MeOH/DCM as eluent), yielding a brown solid that was subsequently purified by reversed phase HPLC on YMC Pack Pro C18 phase (gradient elution; 10%-70% acetonitrile/water as eluent, 0.05% TFA modifier) to afford the title compound 2b. m/z (ES) 495 (MH)$^+$. $^1$HNMR (500 MHz, CD$_3$OD) δ 9.45 (s, 1H), 8.03 (d, 1H, J=1.7 Hz), 7.78 (d, 2H, J=3.3 Hz), 7.70 (d, 1H, J=0.3 Hz), 7.66 (dd, 1H, J=1.5, 3.5 Hz), 7.39 (d, 2H, J=1.7 Hz), 4.15 (m, 1H), 3.13 (m, 2H), 2.55 (d, 1H, J=2.3 Hz), 2.15 (d, 1H, 2.4 Hz), 1.60-1.90 (m, 6H), 1.23 (m, 6H). IC$_{50}$=3.6 nM Step C: Preparation of 2-ethyl-4-(4,4,5,5-tetramethyl-1,3,2-dioxaborolan-2-yl)-N-[(1S,3R)-3-(4H-1,2,4-triazol-4-yl)cyclohexyl]benzenesulfonamide (2c)

[1,1'-bis(diphenylphosphino)ferrocene]dichloropalladium-DCM complex (159 mg, 0.218 mmol) were added to a stirred mixture of 2a (1.80 g, 4.35 mmol), bis(pinacolato)diboron (1.22 g, 4.79 mmol) and potassium acetate (1.28 g, 13.1 mmol) in DMSO (30.0 mL), and the resulting mixture was degassed and heated to 80° C. After 3 h, the reaction mixture was cooled to rt, diluted with EtOAc and filtered through a short column of Celite®, eluting copiously with EtOAc. The combined organics were concentrated in vacuo to afford the title compound, 2c. m/z (ES) 461 (MH)$^+$ Step D: Preparation of 2-ethyl-4-imidazo[1,2-a]pyridin-8-yl-N-[(1S,3R)-3-(4H-1,2,4-triazol-4-yl)cyclohexyl]benzenesulfonamide (2d)

Compound 2c (1.50 mL of a 0.1 M DME solution, 0.150 mmol) was added to a mixture of 8-bromoimidazo[1,2-a]pyridine (29.6 mg, 0.150 mmol), sodium carbonate (150 μL of a 2 M aq. solution, 0.300 mmol) and tetrakistriphenylphosphine palladium(0) (17.3 mg, 0.015 mmol) in DME:water:EtOH (2.00 mL of a 12:4:3 mixture, respectively). The reaction mixture was placed in a sealed tube and heated in a microwave reactor at 120° C. for 15 min. After cooling to rt, the mixture was diluted with EtOAc and filtered through a short column Celite®, eluting copiously with EtOAc. The combined organics were concentrated in vacuo, and the resulting crude residue was purified by preparative thin layer chromatography on silica gel (10% MeOH/DCM as eluent) to afford the title compound, 2d. m/z (ES) 453 (MH)$^+$. IC$_{50}$=3.9 nM Following procedures similar to those described above in Examples 1 and 2, the compounds in the Tables below could be prepared:

TABLE 2A

| Ex. #2A | Ex. #2B | Ex. #2C | Ex. #2D | R¹ | R² |
|---|---|---|---|---|---|
| a | a | a | a | CF₃ | 5-cyclopropyl-1,2,4-oxadiazol-3-yl |
| b | b | b | b | cPr | |
| c | c | c | c | | 5-cyclobutyl-1,2,4-oxadiazol-3-yl |
| d | d | d | d | | 5-(3,3-difluorocyclobutyl)-1,2,4-oxadiazol-3-yl |
| e | e | e | e | H | NO₂ |
| f | f | f | f | | Ph |
| g | g | g | g | | 6-methoxypyridin-3-yl |
| h | h | h | h | | 6-cyanopyridin-3-yl |
| i | i | i | i | | 6-methylpyridin-3-yl |
| j | j | j | j | | 2-aminopyrimidin-5-yl |
| k | k | k | k | | pyridin-4-yl |
| l | l | l | l | | 2-fluorophenyl |
| m | m | m | m | | 3-fluorophenyl |
| n | n | n | n | | 4-fluorophenyl |
| o | o | o | o | | pyridin-3-yl |
| p | p | p | p | | 4-methoxyphenyl |
| q | q | q | q | | 2-methoxypyridin-3-yl |
| r | r | r | r | | 3-methoxyphenyl |
| s | s | s | s | | 2-methoxyphenyl |
| t | t | t | t | | 3-fluoro-4-methoxyphenyl |
| u | u | u | u | | 3,5-dimethoxyphenyl |
| v | v | v | v | | 2,4-difluorophenyl |

TABLE 2A-continued
| Ex. #2A | Ex. #2B | Ex. #2C | Ex. #2D | R¹ | R² |
|---|---|---|---|---|---|
| w | w | w | w | | 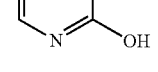 |
| x | x | x | x | |  |
| y | y | y | y | |  |
| z | z | z | z | | 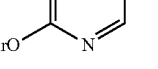 |
| aa | aa | aa | as | | 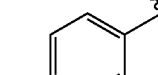 |
| ab | ab | ab | ab | |  |
| ac | ac | ac | ac | | 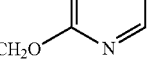 |
| ad | ad | ad | ad | | 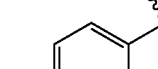 |
| ae | ae | ae | ae | |  |
| — | af | af | af | | 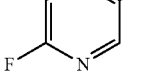 |
| ag | ag | ag | ag | | |
| ah | ah | ah | ah | | |
| ai | ai | ai | ai | | |
| aj | aj | aj | aj | | |
| ak | ak | ak | ak | | |
| — | al | al | al | | |
| am | am | am | am | | |
| an | an | an | an | | |
| ao | ao | ao | ao | | |
| ap | ap | ap | ap | | 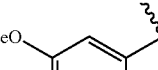 |

TABLE 2A-continued

| Ex. #2A | Ex. #2B | Ex. #2C | Ex. #2D | R¹ | R² |
|---|---|---|---|---|---|
| aq | aq | aq | aq | | cyclobutoxy-pyridinyl |
| ar | ar | ar | ar | | 2,6-bis(trifluoromethyl)pyridin-3-yl |
| — | as | as | as | | imidazo[1,2-a]pyridin-8-yl |
| at | at | at | at | | 6-chloroimidazo[1,2-a]pyridin-8-yl |
| au | au | au | au | | pyrazolo[1,5-a]pyrimidin-6-yl |
| av | av | av | av | | pyrazolo[1,5-a]pyrimidin-5-yl |
| aw | aw | aw | aw | | thiazol-2-yl |
| ax | ax | ax | ax | | thiazol-5-yl |
| ay | ay | ay | ay | | thiazol-4-yl |
| az | az | az | az | | 1,3,4-thiadiazol-2-yl |

TABLE 2A-continued

| Ex. #2A | Ex. #2B | Ex. #2C | Ex. #2D | R¹ | R² |
|---|---|---|---|---|---|
| ba | ba | ba | ba | | 5-(methoxymethyl)-1,3,4-thiadiazol-2-yl |
| bb | bb | bb | bb | Me | 5-cyclopropyl-1,2,4-oxadiazol-3-yl |
| bc | bc | bc | bc | | 6-isopropoxypyridin-3-yl |
| bd | bd | bd | bd | | 4-(trifluoromethoxy)phenyl |
| be | be | be | be | | 6-(2,2,2-trifluoroethoxy)pyridin-3-yl |
| bf | bf | bf | bf | | 3-fluoro-4-(trifluoromethoxy)phenyl |
| bg | bg | bg | bg | | 5-cyclobutyl-1,2,4-oxadiazol-3-yl |
| bh | bh | bh | bh | | 5-cyclopentyl-1,2,4-oxadiazol-3-yl |
| bi | bi | bi | bi | H | —O(CH₂)₃CF₃ |
| bj | bj | bj | bj | Me | —O(CH₂)₃CF₃ |
| bk | bk | bk | bk | H | —O(CH₂)₃CF₃ |
| bl | bl | bl | bl | | 3-methyl-4-(trifluoromethoxy)phenyl |

TABLE 2A-continued

| Ex. #2A | Ex. #2B | Ex. #2C | Ex. #2D | R¹ | R² |
|---|---|---|---|---|---|
| bm | bm | bm | bm | | 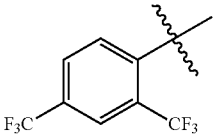 |
| bn | bn | bn | bn | | 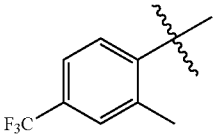 |
| bo | bo | bo | bo | | 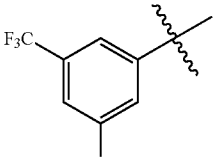 |

2A

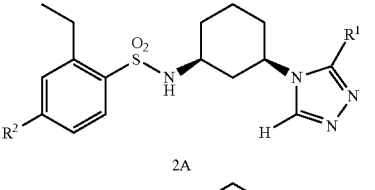

2B

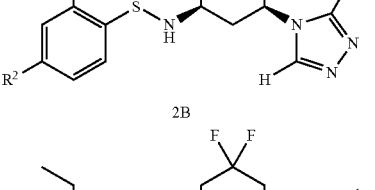

2C

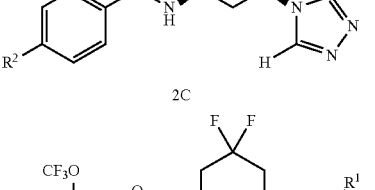

2D

Table 2A. Parent Ion m/z (MH)$^+$ and PAFR binding IC$_{50}$ data for compounds:

2Aa: 4-(5-cyclopropyl-1,2,4-oxadiazol-3-yl)-2-ethyl-N-{(1S,3R)-3-[3-(trifluoromethyl)-4H-1,2,4-triazol-4-yl]cyclohexyl}benzenesulfonamide: m/z (ES) 512 (MH)$^+$; IC$_{50}$=5.5 nM 2Ab: 4-(5-cyclopropyl-1,2,4-oxadiazol-3-yl)-2-ethyl-N-[(1S,3R)-3-(3-cycloropyl-4H-1,2,4-triazol-4-yl)cyclohexyl]benzenesulfonamide: m/z (ES) 483 (MH)$^+$; IC$_{50}$=3.2 nM 2Ae: 2-ethyl-4-nitro-N-[(1S,3R)-3-(4H-1,2,4-triazol-4-yl)cyclohexyl]benzenesulfonamide: m/z (ES) 380 (MH)$^+$; IC$_{50}$=381 nM 2Af: 2-ethyl-N-[(1S,3R)-3-(4H-1,2,4-triazol-4-yl)cyclohexyl]biphenyl-4-sulfonamide: m/z (ES) 411 (MH)$^+$; IC$_{50}$=15 nM 2Ag: 2-ethyl-4-(6-methoxypyridin-3-yl)-N-[(1S,3R)-3-(4H-1,2,4-triazol-4-yl)cyclohexyl]benzenesulfonamide: m/z (ES) 442 (MH)$^+$; IC$_{50}$=9.9 nM 2Ah: 4-(6-cyanopyridin-3-yl)-2-ethyl-N-[(1S,3R)-3-(4H-1,2,4-triazol-4-yl)cyclohexyl]benzenesulfonamide: m/z (ES) 437 (MH)$^+$; IC$_{50}$=570 nM 2Ai: 2-ethyl-4-(6-methylpyridin-3-yl)-N-[(1S,3R)-3-(4H-1,2,4-triazol-4-yl)cyclohexyl]benzenesulfonamide: m/z (ES) 426 (MH)$^+$; IC$_{50}$=119 nM 2Aj: 4-(2-aminopyrimidin-5-yl)-2-ethyl-N-[(1S,3R)-3-(4H-1,2,4-triazol-4-yl)cyclohexyl]benzenesulfonamide: m/z (ES) 428 (MH)$^+$; IC$_{50}$=1060 nM 2Ak: 2-ethyl-4-pyridin-4-yl-N-[(1S,3R)-3-(4H-1,2,4-triazol-4-yl)cyclohexyl]benzenesulfonamide: m/z (ES) 412 (MH)$^+$; IC$_{50}$=95 nM 2Al: 3-ethyl-2'-fluoro-N-[(1S,3R)-3-(4H-1,2,4-triazol-4-yl)cyclohexyl]benzenesulfonamide: m/z (ES) 429 (MH)$^+$; IC$_{50}$=22 nM 2 Am: 3-ethyl-3'-fluoro-N-[(1S,3R)-3-(4H-1,2,4-triazol-4-yl)cyclohexyl]benzenesulfonamide: m/z (ES) 429 (MH)$^+$; IC$_{50}$=33 nM 2An: 3-ethyl-4'-fluoro-N-[(1S,3R)-3-(4H-1,2,4-triazol-4-yl)cyclohexyl]benzenesulfonamide: m/z (ES) 429 (MH)$^+$; IC$_{50}$=17 nM 2Ao: 2-ethyl-4-pyridin-3-yl-N-[(1S,3R)-3-(4H-1,2,4-triazol-4-yl)cyclohexyl]benzenesulfonamide: m/z (ES) 412 (MH)$^+$; IC$_{50}$=159 nM 2Ap: 3-ethyl-4'-methoxy-N-[(1S,3R)-3-(4H-1,2,4-triazol-4-yl)cyclohexyl]biphenyl-4-sulfonamide: m/z (ES) 441 (MH)$^+$; IC$_{50}$=27 nM 2Aq: 2-ethyl-4-(2-methoxypyridin-3-yl)-N-[(1S,3R)-3-(4H-1,2,4-triazol-4-yl)cyclohexyl]benzenesulfonamide: m/z (ES) 442 (MH)$^+$; IC$_{50}$=27 nM 2Ar: 3-ethyl-3'-methoxy-N-[(1S,3R)-3-(4H-1,2,4-triazol-4-yl)cyclohexyl]biphenyl-4-sulfonamide: m/z (ES) 441 (MH)$^+$; IC$_{50}$=27 nM 2As: 3-ethyl-2'-methoxy-N-[(1S,3R)-3-(4H-1,2,4-triazol-4-yl)cyclohexyl]biphenyl-4-sulfonamide: m/z (ES) 441 (MH)$^+$; IC$_{50}$=16 nM 2At: 3-ethyl-3'-fluoro-4'-methoxy-N-[(1S,3R)-3-(4H-1,2,4-triazol-4-yl)cyclohexyl]biphenyl-4-sulfonamide: m/z (ES) 459 (MH)$^+$; IC$_{50}$=39 nM 2Au: 3-ethyl-3',5'-dimethoxy-N-[(1S,3R)-3-(4H-1,2,4-triazol-4-yl)cyclohexyl]biphenyl-4-sulfonamide: m/z (ES) 471 (MH)$^+$; IC$_{50}$=19 nM 2Av: 3-ethyl-2',4'-difluoro-N-[(1S,3R)-3-(4H-1,2,4-triazol-4-yl)cyclohexyl]biphenyl-4-sulfonamide: m/z (ES) 447 (MH)$^+$; IC$_{50}$=16 nM 2Aw: 3-ethyl-3',4'-difluoro-N-[(1S,3R)-3-(4H-1,2,4-triazol-4-yl)cyclohexyl]biphenyl-4-sulfonamide: m/z (ES) 447 (MH)$^+$; IC$_{50}$=24 nM 2Ax: 4-(1,3-benzodioxol-5-yl)-2-ethyl-N-[(1S,3R)-3-(4H-1,2,4-triazol-4-yl)cyclohexyl]benzenesulfonamide: m/z (ES) 455 (MH)$^+$; IC$_{50}$=38 nM 2Ay: 4'-(difluoromethoxy)-3-ethyl-N-[(1S,3R)-3-(4H-1,2,4-triazol-4-yl)cyclohexyl]biphenyl-4-sulfonamide: m/z (ES) 477 (MH)$^+$; IC$_{50}$=2.5 nM 2Az: 4-(3,5-dimethylisoxazol-4-yl)-2-ethyl-N-[(1S,3R)-3-(4H-1,2,4-triazol-4-yl)cyclohexyl]benzenesulfonamide: m/z (ES) 430 (MH)$^+$; IC$_{50}$=48 nM 2Aaa: 3-ethyl-N-[(1S,3R)-3-(4H-1,2,4-triazol-4-yl)cyclohexyl]2'-(trifluoromethoxy)biphenyl-4-sulfonamide: m/z (ES) 495 (MH)$^+$; IC$_{50}$=44 nM 2Aab: 3-ethyl-2'-methoxy-N-[(1S,3R)-3-(4H-1,2,4-triazol-4-yl)cyclohexyl]-6'-(trifluoromethoxy)biphenyl-4-sulfonamide: m/z (ES) 526 (MH)$^+$; IC$_{50}$=54 nM 2Aac: 3-ethyl-3'-fluoro-N-[(1S,3R)-3-(4H-1,2,4-triazol-4-yl)cyclohexyl]-4'-(trifluoromethoxy)biphenyl-4-sulfonamide: m/z (ES) 513 (MH)$^+$; IC$_{50}$=13 nM 2Aad: 3-ethyl-4'-hydroxy-N-[(1S,3R)-3-(4H-1,2,4-triazol-4-yl)cyclohexyl]biphenyl-4-sulfonamide: m/z (ES) 427 (MH)$^+$; IC$_{50}$=36 nM 2Aae: 2-ethyl-4-quinolin-8-yl-N-[(1S,3R)-3-(4H-1,2,4-triazol-4-yl)cyclohexyl]benzenesulfonamide: m/z (ES) 462 (MH)$^+$; IC$_{50}$=4.9 nM 2Aag: 2-ethyl-4-(2-hydroxypyridin-3-yl)-N-[(1S,3R)-3-(4H-1,2,4-triazol-4-yl)cyclohexyl]benzenesulfonamide: m/z (ES) 428 (MH)$^+$; IC$_{50}$=167 nM 2Aah: 3-ethyl-N-[(1S,3R)-3-(4H-1,2,4-triazol-4-yl)cyclohexyl]trifluorethoxy)biphenyl-4-sulfonamide: m/z (ES) 509 (MH)$^+$; IC$_{50}$=2.1 nM 2Aai: 2-ethyl-4-(6-isopropoxypyridin-3-yl)-N-[(1S,3R)-3-(4H-1,2,4-triazol-4-yl)cyclohexyl]benzenesulfonamide: m/z (ES) 470 (MH)$^+$; IC$_{50}$=1.8 nM 2Aaj: 3-ethyl-4'-isopropoxy-N-[(1S,3R)-3-(4H-1,2,4-triazol-4-yl)cyclohexyl]biphenyl-4-sulfonamide: m/z (ES) 469 (MH)$^+$; IC$_{50}$=0.8 nM 2Aak: 2-ethyl-N-[(1S,3R)-3-(4H-1,2,4-triazol-4-yl)cyclohexyl]-4-[6-(2,2,2-trifluoroethoxy)pyridin-3-yl]benzenesulfonamide: m/z (ES) 510 (MH)$^+$; IC$_{50}$=0.7 nM 2Aam: 2-ethyl-4-(6-fluoropyridin-3-yl)-N-[(1S,3R)-3-(4H-1,2,4-triazol-4-yl)cyclohexyl]benzenesulfonamide: m/z (ES) 430 (MH)$^+$; IC$_{50}$=81 nM 2Aan: 2-ethyl-4-(5-methoxypyridin-3-yl)-N-[(1S,3R)-3-(4H-1,2,4-triazol-4-yl)cyclohexyl]benzenesulfonamide: m/z (ES) 442 (MH)$^+$; IC$_{50}$=71 nM 2Aao: N'-[3'-ethyl-4'-({[(1S,3R)-3-(4H-1,2,4-triazol-4-yl)cyclohexyl]amino}sulfonyl)biphenyl-4-yl]acetamide: m/z (ES) 468 (MH)$^+$; IC$_{50}$=57 nM 2Aap: 3-ethyl-N-[(1S,3R)-3-(4H-1,2,4-triazol-4-yl)cyclohexyl]-4'-[2,2,2-trifluoro-1-(trifluoromethyl)ethoxy]biphenyl-4-sulfonamide: m/z (ES) 578 (MH)$^+$; IC$_{50}$=1.7 nM 2Aaq: 4-[6-(cyclobutyloxy)pyridin-3-yl]-2-ethyl-N-[(1S,3R)-3-(4H-1,2,4-triazol-4-yl)cyclohexyl]benzenesulfonamide: m/z (ES) 482 (MH)$^+$; IC$_{50}$=0.8 nM 2Aat: 4-(6-chloroimidazo[1,2-a]pyridin-8-yl)-2-ethyl-N-[(1S,3R)-3-(4H-1,2,4-triazol-4-yl)cyclohexyl]benzenesulfonamide: m/z (ES) 486 (MH)$^+$; IC$_{50}$=2.2 nM 2Aau: 2-ethyl-4-pyrazolo[1,5-a]pyrimidin-6-yl-N-[(1S,3R)-3-(4H-1,2,4-triazol-4-yl)cyclohexyl]benzenesulfonamide: m/z (ES) 453 (MH)$^+$; IC$_{50}$=244 nM 2Aav: 2-ethyl-4-pyrazolo[1,5-a]pyrimidin-5-yl-N-[(1S,3R)-3-(4H-1,2,4-triazol-4-yl)cyclohexyl]benzenesulfonamide: m/z (ES) 453 (MH)$^+$; IC$_{50}$=9.7 nM 2Aaw: 2-ethyl-4-(1,3-thiazol-2-yl)-N-[(1S,3R)-3-(4H-1,2,4-triazol-4-yl)cyclohexyl]benzenesulfonamide: m/z (ES) 418 (MH)$^+$; IC$_{50}$=45 nM 2Aax: 2-ethyl-4-(1,3-thiazol-5-yl)-N-[(1S,3R)-3-(4H-1,2,4-triazol-4-yl)cyclohexyl]benzenesulfonamide: m/z (ES) 418 (MH)$^+$; IC$_{50}$=203 nM 2Aay: 2-ethyl-4-(1,3-thiazol-4-yl)-N-[(1S,3R)-3-(4H-1,2,4-triazol-4-yl)cyclohexyl]benzenesulfonamide: m/z (ES) 418 (MH)$^+$; IC$_{50}$=69 nM 2Aaz: 2-ethyl-4-(1,2,4-thiadiazol-5-yl)-N-[(1S,3R)-3-(4H-1,2,4-triazol-4-yl)cyclohexyl]benzenesulfonamide: m/z (ES) 420 (MH)$^+$; IC$_{50}$=390 nM 2Aba: 2-ethyl-4-[5-(methoxymethyl)-1,3-thiazol-2-yl]-N-[(1S,3R)-3-(4H-1,2,4-triazol-4-yl)cyclohexyl]benzenesulfonamide: m/z (ES) 462 (MH)$^+$; IC$_{50}$=41 nM 2Abb: 4-(5-cyclopropyl-1,2,4-oxadiazol-3-yl)-2-ethyl-N-[(1S,3R)-3-(3-methyl-4H-1,2,4-triazol-4-yl)cyclohexyl]benzenesulfonamide: m/z (ES) 457 (MH)$^+$; IC$_{50}$=2.0 nM 2Abc: 2-ethyl-4-(6-isopropoxypyridin-3-yl)-N-[(1S,3R)-3-(3-methyl-4H-1,2,4-triazol-4-yl)cyclohexyl]benzenesulfonamide: m/z (ES) 484 (MH)$^+$; IC$_{50}$=0.5 nM 2Abd: 3-ethyl-N-[(1S,3R)-3-(3-methyl-4H-1,2,4-triazol-4-yl)cyclohexyl]-4'-(trifluoromethoxy)biphenyl-4-sulfonamide: m/z (ES) 509 (MH)$^+$; IC$_{50}$=2.2 nM 2Abe: 2-ethyl-N-[(1S,3R)-3-(3-methyl-4H-1,2,4-triazol-4-yl)cyclohexyl]-4-[6-(2,2,2-trifluoroethoxy)pyridin-3-yl]benzenesulfonamide: m/z (ES) 524 (MH)$^+$; IC$_{50}$=0.2 nM 2Abf: 3-ethyl-3'-fluoro-N-[(1S,3R)-3-(3-methyl-4H-1,2,4-triazol-4-yl)cyclohexyl]-4'-(trifluoromethoxy)biphenyl-4-sulfonamide: m/z (ES) 527 (MH)$^+$; IC$_{50}$=2.7 nM 2Abi: 2-ethyl-N-[(1S,3R)-3-(4H-1,2,4-triazol-4-yl)cyclohexyl]-4-(4,4,4-trifluorobutoxy)benzenesulfonamide: m/z (ES) 461 (MH)$^+$; IC$_{50}$=2.7 nM 2Abj: 2-ethyl-N-[(1S,3R)-3-(3-methyl-4H-1,2,4-triazol-4-yl)cyclohexyl]-4-(4,4,4-trifluorobutoxy)benzenesulfonamide: m/z (ES) 475 (MH)$^+$; IC$_{50}$=2.7 nM 2Abk: 2-ethyl-N-[(1S,3R)-3-(4H-1,2,4-triazol-4-yl)cyclohexyl]-4-(3,3,3-trifluoropropoxy)benzenesulfonamide: m/z (ES) 447 (MH)$^+$; IC$_{50}$=22 nM 2Abl: 3-ethyl-2'-methyl-N-[(1S,3R)-3-(3-methyl-4H-1,2,4-triazol-4-yl)cyclohexyl]-4'-(trifluoromethoxy)biphenyl-4-sulfonamide: m/z (ES) 509 (MH)$^+$; IC$_{50}$=30 nM 2Abm: 3-ethyl-N-[(1S,3R)-3-(4H-1,2,4-triazol-4-yl)cyclohexyl]-2',4'-bis(trifluoromethyl)biphenyl-4-sulfonamide: m/z (ES) 547 (MH)$^+$; IC$_{50}$=83 nM 2Abn: 3-ethyl-2'-methyl-N-[(1S,3R)-3-(4H-1,2,4-triazol-4-yl)cyclohexyl]-4'-(trifluoromethyl)biphenyl-4-sulfonamide: m/z (ES) 493 (MH)$^+$; IC$_{50}$=22 nM 2Abo: 3-ethyl-N-[(1S,3R)-3-(4H-1,2,4-triazol-4-yl)cyclohexyl]-3',5'-bis(trifluoromethyl)biphenyl-4-sulfonamide: m/z (ES) 547 (MH)$^+$; IC$_{50}$=13 nM 2Bb: 4-(5-cyclopropyl-1,2,4-oxadiazol-3-yl)-N-[(1S,3R)-3-(3-cyclopropyl-4H-1,2,4-triazol-4-yl)cyclohexyl]-2-(trifluoromethoxy)benzenesulfonamide: m/z (ES) 539 (MH)$^+$; IC$_{50}$=4.3 nM 2Bc: 4-(5-cyclobutyl-1,2,4-oxadiazol-3-yl)-N-[(1S,3R)-3-(3-cyclopropyl-4H-1,2,4-triazol-4-yl)cyclohexyl]-2-(trifluoromethoxy)benzenesulfonamide: m/z (ES) 553 (MH)$^+$; IC$_{50}$=2.5 nM 2Bd: N-[(1S,3R)-3-(3-cyclopropyl-4H-1,2,4-triazol-4-yl)cyclohexyl]-4-[5-(3,3-difluorocyclobutyl)-1,2,4-oxadiazol-3-yl]-2-(trifluoromethoxy)benzenesulfonamide: m/z (ES) 589 (MH)$^+$; IC$_{50}$=6.3 nM 2Bal: N-[(1S,3R)-3-(4H-1,2,4-triazol-4-yl)cyclohexyl]-3',4'-bis(trifluoromethoxy)biphenyl-4-sulfonamide: m/z (ES) 551 (MH)$^+$; IC$_{50}$=15 nM 2Bbd: N-[(1S,3R)-3-(3-methyl-4H-1,2,4-triazol-4-yl)cyclohexyl]-3',4'-bis(trifluoromethoxy)biphenyl-4-sulfonamide: m/z (ES) 565 (MH)$^+$; IC$_{50}$=6.2 nM 2Bbe: N-[(1S,3R)-3-(3-methyl-4H-1,2,4-triazol-4-yl)cyclohexyl]-4-[6-(2,2,2-trifluoroethoxy)pyridin-3-yl]-2-(trifluoromethoxy)benzenesulfonamide: m/z (ES) 580 (MH)$^+$; IC$_{50}$=2.0 nM 2Bbg: 4-(5-cyclobutyl-1,2,4-oxadiazol-3-yl)-N-[(1S,3R)-3-(3-methyl-4H-1,2,4-triazol-4-yl)cyclohexyl]-2-(trifluoromethoxy)benzenesulfonamide: m/z (ES) 527 (MH)$^+$; IC$_{50}$=1.5 nM 2Bbh: 4-(5-cyclopentyl-1,2,4-oxadiazol-3-yl)-N-[(1S,3R)-3-(3-methyl-4H-1,2,4-triazol-4-yl)cyclohexyl]-2-(trifluoromethoxy)benzenesulfonamide: m/z (ES) 541 (MH)$^+$; IC$_{50}$=3.8 nM 2Cy: 4-(5-cyclopropyl-1,2,4-oxadiazol-3-yl)-N-[(1R,5S)-3,3-difluoro-5-(4H-1,2,4-triazol-4-yl)cyclohexyl]-3-ethylbiphenyl-4-sulfonamide: m/z (ES) 513 (MH)$^+$; IC$_{50}$=7.3 nM 2Caf: 4'-(difluoromethoxy)-N-[(1R,5S)-3,3-difluoro-5-(4H-1,2,4-triazol-4-yl)cyclohexyl]-2-ethylbenzenesulfonamide: m/z (ES) 479 (MH)$^+$; IC$_{50}$=12 nM 2Cak: N-[(1R,5S)-3,3-difluoro-5-(4H-1,2,4-triazol-4-yl)cyclohexyl]-2-ethyl-4-[6-(2,2,2-trifluoroethoxy)pyridin-3-yl]benzenesulfonamide: m/z (ES) 546 (MH)$^+$; IC$_{50}$=3.1 nM 2Cal: N-[(1R,5S)-3,3-difluoro-5-(4H-1,2,4-triazol-4-yl)cyclohexyl]-3-ethyl-4'-(trifluoromethoxy)biphenyl-4-sulfonamide: m/z (ES) 532 (MH)$^+$; IC$_{50}$=11 nM 2Cbb: 4-(5-cyclopropyl-1,2,4-oxadiazol-3-yl)-N-[(1R,5S)-3,3-difluoro-5-(3-methyl-4H-1,2,4-triazol-4-yl)cyclohexyl]-2-ethylbenzenesulfonamide: m/z (ES) 493 (MH)$^+$; IC$_{50}$=0.8 nM 2Cbd: N-[(1R,5S)-3,3-difluoro-5-(3-methyl-4H-1,2,4-triazol-4-yl)cyclohexyl]-3-ethyl-4'-(trifluoromethoxy)biphenyl-4-sulfonamide: m/z (ES) 545 (MH)$^+$; IC$_{50}$=0.9 nM 2Cbe: N-[(1R,5S)-3,3-difluoro-5-(3-methyl-4H-1,2,4-triazol-4-yl)cyclohexyl]-2-ethyl-4-[6-(2,2,2-trifluoroethoxy)pyridin-3-yl]benzenesulfonamide: m/z (ES) 560 (MH)$^+$; IC$_{50}$=0.2 nM

TABLE 2B

| Ex. #2E | Ex. #2F | Ex. #2G | Ex. #2H | R$_1$ |
|---|---|---|---|---|
| a | a | a | a | 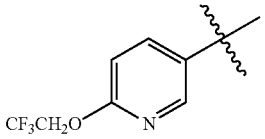 |
| b | b | b | b | 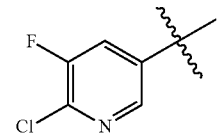 [SMILES: *c1cnc(Cl)c(F)c1] |
| c | c | c | c | 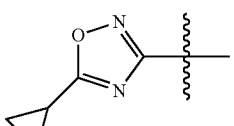 |
| d | d | d | d | 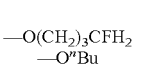 |
| e | e | e | e |  |
| f | f | f | f | 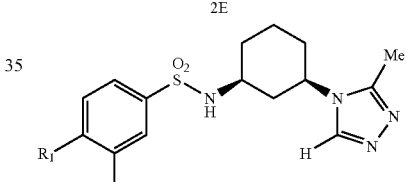 |
| g | g | g | g | 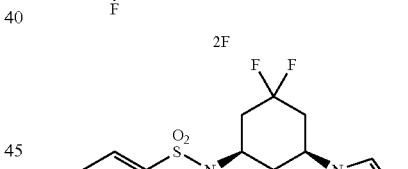 |
| h | h | h | h | 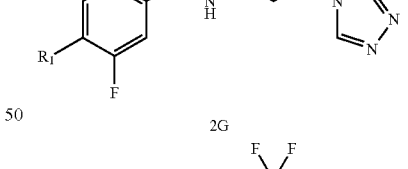 |
| i | i | i | i | —O(CH$_2$)$_3$CFH$_2$ |
| j | j | j | j | —O$^n$Bu |

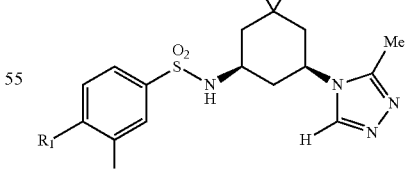

2E

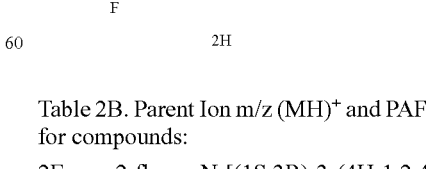

2F

2G

2H

Table 2B. Parent Ion m/z (MH)$^+$ and PAFR binding IC$_{50}$ data for compounds:

2Ea: 2-fluoro-N-[(1S,3R)-3-(4H-1,2,4-triazol-4-yl)cyclohexyl]-4'-(trifluoromethoxy)biphenyl-4-sulfonamide: m/z (ES) 485 (MH)$^+$; IC$_{50}$=5.8 nM 2Eb: 2-fluoro-N-[(1S,3R)-3-(4H-1,2,4-triazol-4-yl)cyclohexyl]-4'-(2,2,2-trifluoroethoxy)biphenyl-4-sulfonamide: m/z (ES) 499 (MH)$^+$; IC$_{50}$=0.7 nM 2Ec: 4'-(difluoromethoxy)-2-fluoro-N-[(1S,3R)-3-(4H-1,2,4-triazol-4-yl)cyclohexyl]biphenyl-4-sulfonamide: m/z (ES) 467 (MH)$^+$; IC$_{50}$=2.6 nM 2Ed: 2-fluoro-4'-isopropoxy-N-[(1S,3R)-3-(4H-1,2,4-triazol-4-yl)cyclohexyl]biphenyl-4-sulfonamide: m/z (ES) 460 (MH)$^+$; IC$_{50}$=15 nM 2Ee: 3-fluoro-4-(6-isopropoxypyridin-3-yl)-N-[(1S,3R)-3-(4H-1,2,4-triazol-4-yl)cyclohexyl]benzenesulfonamide: m/z (ES) 460 (MH)$^+$; IC$_{50}$=5.1 nM 2Ef: 3-fluoro-N-[(1S,3R)-3-(4H-1,2,4-triazol-4-yl)cyclohexyl]-4-[6-(2,2,2-trifluoroethoxy)pyridin-3-yl]benzenesulfonamide: m/z (ES) 500 (MH)$^+$; IC$_{50}$=7.0 nM 2Fa: 2-fluoro-N-[(1S,3R)-3-(3-methyl-4H-1,2,4-triazol-4-yl)cyclohexyl]-4'-(trifluoromethoxy)biphenyl-4-sulfonamide: m/z (ES) 499 (MH)$^+$; IC$_{50}$=0.2 nM 2Fb: 2-fluoro-N-[(1S,3R)-3-(3-methyl-4H-1,2,4-triazol-4-yl)cyclohexyl]-4'-(2,2,2-trifluoroethoxy)biphenyl-4-sulfonamide: m/z (ES) 513 (MH)$^+$; IC$_{50}$=0.8 nM 2Fc: 4'-(difluoromethoxy)-2-fluoro-N-[(1S,3R)-3-(3-methyl-4H-1,2,4-triazol-4-yl)cyclohexyl]biphenyl-4-sulfonamide: m/z (ES) 481 (MH)$^+$; IC$_{50}$=1.9 nM 2Fe: 3-fluoro-4-(6-isopropoxypyridin-3-yl)-N-[(1S,3R)-3-(3-methyl-4H-1,2,4-triazol-4-yl)cyclohexyl]benzenesulfonamide: m/z (ES) 474 (MH)$^+$; IC$_{50}$=3.6 nM 2Ff: 3-fluoro-N-[(1S,3R)-3-(3-methyl-4H-1,2,4-triazol-4-yl)cyclohexyl]-4-[6-(2,2,2-trifluoroethoxy)pyridin-3-yl]benzenesulfonamide: m/z (ES) 514 (MH)$^+$; IC$_{50}$=1.0 nM 2Fg: 4-(6-chloro-5-fluoropyridin-3-yl)-3-fluoro-N-[(1S,3R)-3-(3-methyl-4H-1,2,4-triazol-4-yl)cyclohexyl]benzenesulfonamide: m/z (ES) 468 (MH)$^+$; IC$_{50}$=36 nM 2Fh: 4-(5-cyclopropyl-1,2,4-oxadiazol-3-yl)-3-fluoro-N-[(1S,3R)-3-(3-methyl-4H-1,2,4-triazol-4-yl)cyclohexyl]benzenesulfonamide: m/z (ES) 447 (MH)$^+$; IC$_{50}$=9.9 nM 2Fi: 3-fluoro-4-(4-fluorobutoxy)-N-[(1S,3R)-3-(3-methyl-4H-1,2,4-triazol-4-yl)cyclohexyl]benzenesulfonamide: m/z (ES) 429 (MH)$^+$; IC$_{50}$=9.7 nM 2Fj: 4-butoxy-3-fluoro-N-[(1S,3R)-3-(3-methyl-4H-1,2,4-triazol-4-yl)cyclohexyl]benzenesulfonamide: m/z (ES) 411 (MH)$^+$; IC$_{50}$=1.9 nM 2Ga: N-[(1R,5S)-3,3-difluoro-5-(4H-1,2,4-triazol-4-yl)cyclohexyl]-2-fluoro-4'-(trifluoromethoxy)biphenyl-4-sulfonamide: m/z (ES) 521 (MH)$^+$; IC$_{50}$=10 nM 2Gd: N-[(1R,5S)-3,3-difluoro-5-(4H-1,2,4-triazol-4-yl)cyclohexyl]-2-fluoro-4'-isopropoxybiphenyl-4-sulfonamide: m/z (ES) 495 (MH)$^+$; IC$_{50}$=7.2 nM 2Gf: N-[(1R,5S)-3,3-difluoro-5-(4H-1,2,4-triazol-4-yl)cyclohexyl]-3-fluoro-4-[6-(2,2,2-trifluoroethoxy)pyridin-3-yl]benzenesulfonamide: m/z (ES) 536 (MH)$^+$; IC$_{50}$=4.4 nM 2Ha: N-[(1R,5S)-3,3-difluoro-5-(3-methyl-4H-1,2,4-triazol-4-yl)cyclohexyl]-2-fluoro-4'-(trifluoromethoxy)biphenyl-4-sulfonamide: m/z (ES) 535 (MH)$^+$; IC$_{50}$=1.4 nM 2Hf: N-[(1R,5S)-3,3-difluoro-5-(3-methyl-4H-1,2,4-triazol-4-yl)cyclohexyl]-3-fluoro-4-[6-(2,2,2-trifluoroethoxy)pyridin-3-yl]benzenesulfonamide: m/z (ES) 550 (MH)$^+$; IC$_{50}$=0.6 nM 2Hi: N-[(1R,5S)-3,3-difluoro-5-(3-methyl-4H-1,2,4-triazol-4-yl)cyclohexyl]-3-fluoro-4-(4-fluorobutoxy)benzenesulfonamide: m/z (ES) 465 (MH)$^+$; IC$_{50}$=6.8 nM 2Hj: 4-butoxy-N-[(1R,5S)-3,3-difluoro-5-(3-methyl-4H-1,2,4-triazol-4-yl)cyclohexyl]-3-fluorobenzenesulfonamide: m/z (ES) 447 (MH)$^+$; IC$_{50}$=3.6 nM

TABLE 2C

| Ex. #2I | Ex. #2J | Ex. #2K | Ex. #2L | R$^1$ | R$^2$ |
|---|---|---|---|---|---|
| a | a | a | a | H | cyclopropyl-1,2,4-oxadiazolyl |
| b | b | b | b |  | F$_3$C-1,2,4-oxadiazolyl |
| c | c | c | c |  | CH$_3$CF$_2$-1,2,4-oxadiazolyl |
| d | d | d | d |  | CH$_3$CH$_2$CF$_2$-1,2,4-oxadiazolyl |
| e | e | e | e |  | HO-cyclopropyl-1,2,4-oxadiazolyl |
| f | f | f | f |  | cyclobutyl-1,2,4-oxadiazolyl |
| g | g | g | g |  | F$_3$CO-phenyl |
| h | h | h | h |  | CF$_3$CH$_2$O-pyridyl |
| i | i | i | i |  | —O"Bu |
| j | j | j | j | F | cyclopropyl-1,2,4-oxadiazolyl |

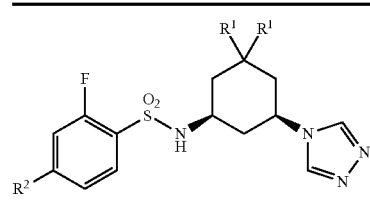

2I

TABLE 2C-continued

| Ex. #2I | Ex. #2J | Ex. #2K | Ex. #2L | R¹ | R² |
|---|---|---|---|---|---|

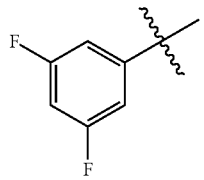 [SMILES: *c1cc(F)cc(F)c1]

Table 2C. Parent Ion m/z (MH)⁺ and PAFR binding IC₅₀ data for compounds:

2Ig: 3-fluoro-N-[(1S,3R)-3-(4H-1,2,4-triazol-4-yl)cyclohexyl]-4'-(trifluoromethoxy)biphenyl-4-sulfonamide: m/z (ES) 485 (MH)⁺; IC₅₀=16 nM 2Ih: 2-fluoro-N-[(1S,3R)-3-(4H-1,2,4-triazol-4-yl)cyclohexyl]-4-[6-(2,2,2-trifluoroethoxy)pyridin-3-yl]benzenesulfonamide: m/z (ES) 500 (MH)⁺; IC₅₀=4.0 nM 2Ja: 4-(5-cyclopropyl-1,2,4-oxadiazol-3-yl)-2-fluoro-N-[(1S,3R)-3-(3-methyl-4H-1,2,4-triazol-4-yl)cyclohexyl]benzenesulfonamide: m/z (ES) 447 (MH)⁺; IC₅₀=22 nM 2Jg: 3-fluoro-N-[(1S,3R)-3-(3-methyl-4H-1,2,4-triazol-4-yl)cyclohexyl]-4'-(trifluoromethoxy)biphenyl-4-sulfonamide: m/z (ES) 499 (MH)⁺; IC₅₀=10 nM 2Jh: 2-fluoro-N-[(1S,3R)-3-(3-methyl-4H-1,2,4-triazol-4-yl)cyclohexyl]-4-[6-(2,2,2-trifluoroethoxy)pyridin-3-yl]benzenesulfonamide: m/z (ES) 514 (MH)⁺; IC₅₀=3.4 nM 2Ji: 4-butoxy-2-fluoro-N-[(1S,3R)-3-(3-methyl-4H-1,2,4-triazol-4-yl)cyclohexyl]benzenesulfonamide: m/z (ES) 411 (MH)⁺; IC₅₀=4.0 nM 2Ka: 2-cyclopropyl-4-(5-cyclopropyl-1,2,4-oxadiazol-3-yl)-N-[(1S,3R)-3-(4H-1,2,4-triazol-4-yl)cyclohexyl]benzenesulfonamide: m/z (ES) 455 (MH)⁺; IC₅₀=2.7 nM 2Kb: 2-cyclopropyl-N-[(1S,3R)-3-(4H-1,2,4-triazol-4-yl)cyclohexyl]-4-[5-(trifluoromethyl)-1,2,4-oxadiazol-3-yl]benzenesulfonamide: m/z (ES) 483 (MH)⁺; IC₅₀=16 nM 2Kc: 2-cyclopropyl-4-[5-(1,1-difluoroethyl)-1,2,4-oxadiazol-3-yl]-N-[(1S,3R)-3-(4H-1,2,4-triazol-4-yl)cyclohexyl]benzenesulfonamide: m/z (ES) 479 (MH)⁺; IC₅₀=9.9 nM 2Kd: 2-cyclopropyl-4-[5-(1,1-difluoropropyl)-1,2,4-oxadiazol-3-yl]-N-[(1S,3R)-3-(4H-1,2,4-triazol-4-yl)cyclohexyl]benzenesulfonamide-1,1-difluoroethylene (1:1): m/z (ES) 493 (MH)⁺; IC₅₀=8.9 nM 2Ke: 2-cyclopropyl-4-[5-(1-hydroxycyclopropyl)-1,2,4-oxadiazol-3-yl]-N-[(1S,3R)-3-(4H-1,2,4-triazol-4-yl)cyclohexyl]benzenesulfonamide: m/z (ES) 471 (MH)⁺; IC₅₀=337 nM 2Kf: 4-(5-cyclobutyl-1,2,4-oxadiazol-3-yl)-2-cyclopropyl-N-[(1S,3R)-3-(4H-1,2,4-triazol-4-yl)cyclohexyl]benzenesulfonamide: m/z (ES) 469 (MH)⁺; IC₅₀=2.8 nM 2Lj: 2-cyclopropyl-4-(5-cyclopropyl-1,2,4-oxadiazol-3-yl)-N-[(1R,5S)-3,3-difluoro-5-(3-methyl-4H-1,2,4-triazol-4-yl)cyclohexyl]benzenesulfonamide: m/z (ES) 505 (MH)⁺; IC₅₀=1.3 nM

TABLE 2D

| Ex. #2M | Ex. #2N | Ex. #2O | Ex. #2P | Ex. #2Q | R |
|---|---|---|---|---|---|
| a | a | a | a | a | 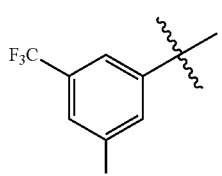 |
| b | b | b | b | b | 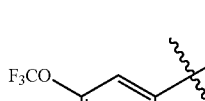 |
| c | c | c | c | c | (F₃CO-phenyl) |

TABLE 2D-continued
| Ex. #2M | Ex. #2N | Ex. #2O | Ex. #2P | Ex. #2Q | R |
|---|---|---|---|---|---|
| d | d | d | d | d | 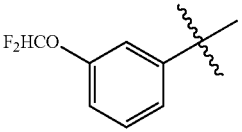 [SMILES: *c1cccc(OC(F)F)c1] |
| e | e | e | e | e | 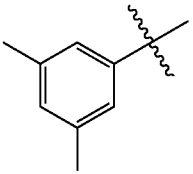 [SMILES: *c1cc(C)cc(C)c1] |
| f | f | f | f | f | 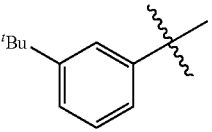 [SMILES: *c1cccc(C(C)(C)C)c1] |
| g | g | g | g | g | 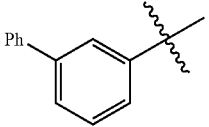 |
| h | h | h | h | h | 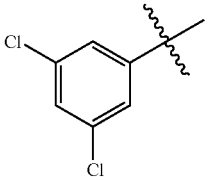 [SMILES: *c1cc(Cl)cc(Cl)c1] |
| i | i | i | i | i | 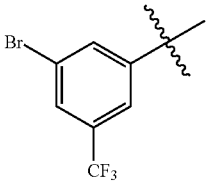 [SMILES: *c1cc(Br)cc(C(F)(F)F)c1] |
| j | j | j | j | j | 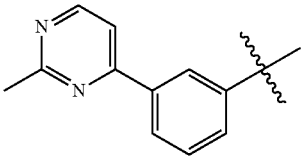 [SMILES: *c1cccc(-c2ccnc(C)n2)c1] |
| k | k | k | k | k | 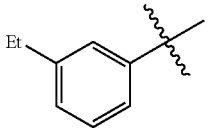 [SMILES: *c1cccc(CC)c1] |
| l | l | l | l | l | 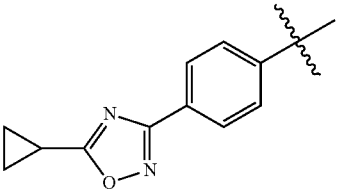 [SMILES: *c1ccc(-c2noc(C3CC3)n2)cc1] |

TABLE 2D-continued
| Ex. #2M | Ex. #2N | Ex. #2O | Ex. #2P | Ex. #2Q | R |
|---------|---------|---------|---------|---------|---|
| m | m | m | m | m | 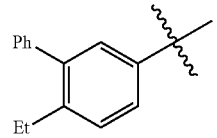 |
| n | n | n | n | n | 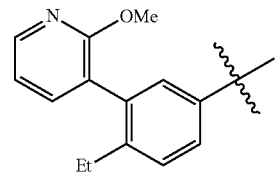 [SMILES: *c1ccc(CC)c(-c2cccnc2OC)c1] |
| o | o | o | o | o | 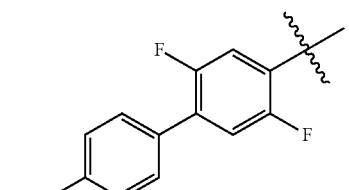 |
| p | p | p | p | p | 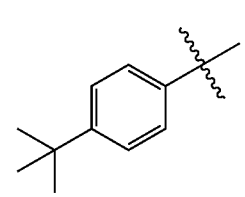 [SMILES: *c1ccc(C(C)(C)C)cc1] |
| q | q | q | q | q | 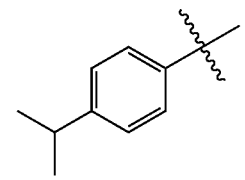 [SMILES: *c1ccc(C(C)C)cc1] |
| r | r | r | r | r | 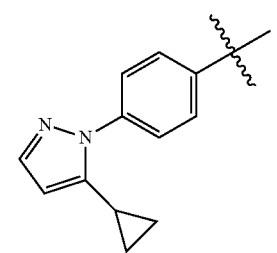 [SMILES: *c1ccc(-n2nccc2C2CC2)cc1] |
| s | s | s | s | s | 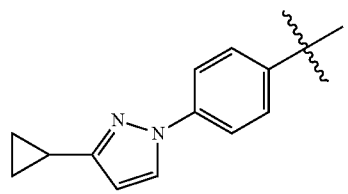 [SMILES: *c1ccc(-n2ccc(C3CC3)n2)cc1] |
| t | t | t | t | t | 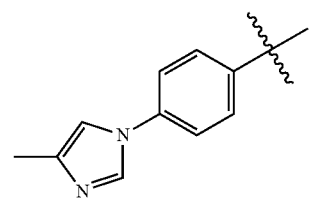 [SMILES: *c1ccc(-n2cnc(C)c2)cc1] |

TABLE 2D-continued
| Ex. #2M | Ex. #2N | Ex. #2O | Ex. #2P | Ex. #2Q | R |
|---|---|---|---|---|---|
| u | u | u | u | u | 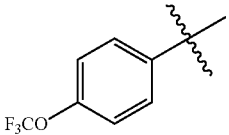 [SMILES: *c1ccc(OC(F)(F)F)cc1] |
| v | v | v | v | v | 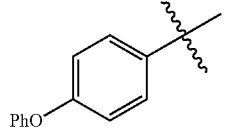 [SMILES: *c1ccc(Oc2ccccc2)cc1] |
| w | w | w | w | w | 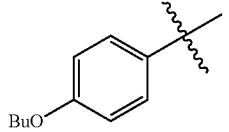 [SMILES: *c1ccc(OC(C)C)cc1] |
| x | x | x | x | x | 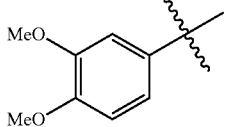 |
| y | y | y | y | y | 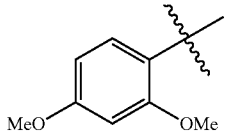 |
| z | z | z | z | z | 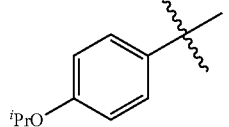 |
| aa | aa | aa | aa | aa | 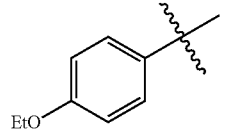 [SMILES: *c1ccc(OCC)cc1] |
| ab | ab | ab | ab | ab | 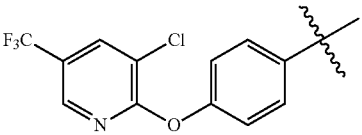 [SMILES: *c1ccc(Oc2ncc(C(F)(F)F)cc2Cl)cc1] |
| ac | ac | ac | ac | ac | 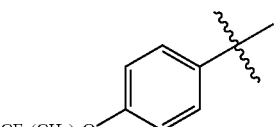 |
| ad | ad | ad | ad | ad | 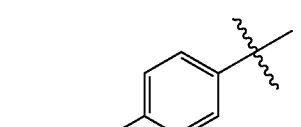 |

TABLE 2D-continued
| Ex. #2M | Ex. #2N | Ex. #2O | Ex. #2P | Ex. #2Q | R |
|---------|---------|---------|---------|---------|---|
| ae | ae | ae | ae | ae | 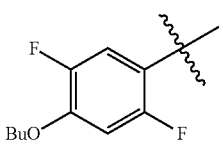 |
| af | af | af | af | af | 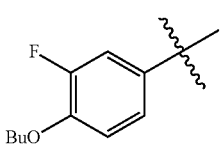 |
| ag | ag | ag | ag | ag | 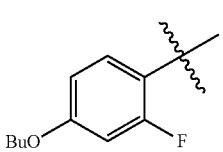 |
| ah | ah | ah | ah | ah | 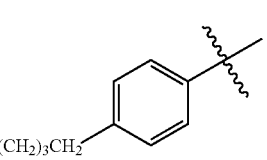 |
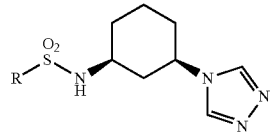
2M
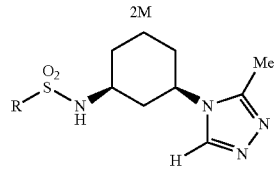
2N
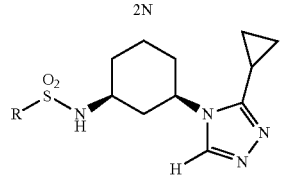
2O
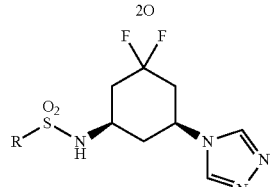
2P
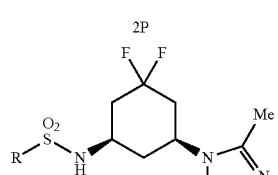
2Q Table 2D. Parent Ion m/z (MH)+ and PAM binding IC$_{50}$ data for compounds:

2Ma: 3,5-difluoro-N-[(1S,3R)-3-(4H-1,2,4-triazol-4-yl)cyclohexyl]benzenesulfonamide: m/z (ES) 343 (MH)+; IC$_{50}$=2900 nM 2 Mb: N-[(1S,3R)-3-(4H-1,2,4-triazol-4-yl)cyclohexyl]-3,5-bis(trifluoromethyl)benzenesulfonamide: m/z (ES) 443 (MH)+; IC$_{50}$=280 nM 2Mc: N-[(1S,3R)-3-(4H-1,2,4-triazol-4-yl)cyclohexyl]-3-(trifluoromethoxy)benzenesulfonamide: m/z (ES) 391 (MH)+; IC$_{50}$=410 nM 2Md: 3-(difluoromethoxy)-N-[(1S,3R)-3-(4H-1,2,4-triazol-4-yl)cyclohexyl]benzenesulfonamide: m/z (ES) 373 (MH)+; IC$_{50}$=323 nM 2Me: 3,5-dimethyl-N-[(1S,3R)-3-(4H-1,2,4-triazol-4-yl)cyclohexyl]benzenesulfonamide: m/z (ES) 335 (MH)+; IC$_{50}$=194 nM 2Mf: 3-tert-butyl-N-[(1S,3R)-3-(4H-1,2,4-triazol-4-yl)cyclohexyl]benzenesulfonamide: m/z (ES) 363 (MH)+; IC$_{50}$=157 nM 2Mg: N-[(1S,3R)-3-(4H-1,2,4-triazol-4-yl)cyclohexyl]biphenyl-3-sulfonamide: m/z (ES) 383 (MH)+; IC$_{50}$=30 nM 2 Mh: 3,5-dichloro-N-[(1S,3R)-3-(4H-1,2,4-triazol-4-yl)cyclohexyl]benzenesulfonamide: m/z (ES) 375 (MH)+; IC$_{50}$=194 nM 2Mi: 3-bromo-N-[(1S,3R)-3-(4H-1,2,4-triazol-4-yl)cyclohexyl]-5-(trifluoromethyl)benzenesulfonamide: m/z (ES) 453 (MH)+; IC$_{50}$=165 nM 2Ml: 4-(5-cyclopropyl-1,2,4-oxadiazol-3-yl)-N-[(1S,3R)-3-(4H-1,2,4-triazol-4-yl)cyclohexyl]benzenesulfonamide: m/z (ES) 415 (MH)+; IC$_{50}$=243 nM 2Mm: 6-ethyl-N-[(1S,3R)-3-(4H-1,2,4-triazol-4-yl)cyclohexyl]biphenyl-3-sulfonamide: m/z (ES) 411 (MH)+; IC$_{50}$=26 nM 2Mn: 4-ethyl-3-(2-methoxypyridin-3-yl)-N-[(1S,3R)-3-(4H-1,2,4-triazol-4-yl)cyclohexyl]benzenesulfonamide: m/z (ES) 442 (MH)+; IC$_{50}$=63 nM 2Mo: 2,5-difluoro-N-[(1S,3R)-3-(4H-1,2,4-triazol-4-yl)cyclohexyl]-4'-(trifluoromethoxy)biphenyl-4-sulfonamide: m/z (ES) 503 (MH)+; IC$_{50}$=12 nM 2Mu: N-[(1S,3R)-3-(4H-1,2,4-triazol-4-yl)cyclohexyl]-4-(trifluoromethoxy)benzenesulfonamide: m/z (ES) 391 (MH)+; IC$_{50}$=164 nM 2Mv: 4-phenoxy-N-[(1S,3R)-3-(4H-1,2,4-triazol-4-yl)cyclohexyl]benzenesulfonamide: m/z (ES) 399 (MH)+; IC$_{50}$=51 nM 2Mw: 4-butoxy-N-[(1S,3R)-3-(4H-1,2,4-triazol-4-yl)cyclohexyl]benzenesulfonamide: m/z (ES) 379 (MH)+; IC$_{50}$=8.3 nM 2Mx: 3,4-dimethoxy-N-[(1S,3R)-3-(4H-1,2,4-triazol-4-yl)cyclohexyl]benzenesulfonamide: m/z (ES) 367 (MH)+; IC$_{50}$=600 nM 2My: 2,4-dimethoxy-N-[(1S,3R)-3-(4H-1,2,4-triazol-4-yl)cyclohexyl]benzenesulfonamide: m/z (ES) 367 (MH)+; IC$_{50}$=210 nM 2Mz: 4-isopropoxy-N-[(1S,3R)-3-(4H-1,2,4-triazol-4-yl)cyclohexyl]benzenesulfonamide: IC$_{50}$=25 nM 2Maa: 4-ethoxy-N-[(1S,3R)-3-(4H-1,2,4-triazol-4-yl)cyclohexyl]benzenesulfonamide: m/z (ES) 351 (MH)+; IC$_{50}$=39 nM 2Mab: 4-{[3-chloro-5-(trifluoromethyl)pyridin-2-yl]oxy}-N-[(1S,3R)-3-(4H-1,2,4-triazol-4-yl)cyclohexyl]benzenesulfonamide: m/z (ES) 502 (MH)+; IC$_{50}$=66 nM 2Mac: N-[(1S,3R)-3-(4H-1,2,4-triazol-4-yl)cyclohexyl]-4-(4,4,4-trifluorobutoxy)benzenesulfonamide: m/z (ES) 433 (MH)+; IC$_{50}$=8.3 nM 2Mah: 4-pentyl-N-[(1S,3R)-3-(4H-1,2,4-triazol-4-yl)cyclohexyl]benzenesulfonamide: m/z (ES) 377 (MH)+; IC$_{50}$=13 nM 2Nl: 4-(5-cyclopropyl-1,2,4-oxadiazol-3-yl)-N-[(1S,3R)-3-(3-methyl-4H-1,2,4-triazol-4-yl)cyclohexyl]benzenesulfonamide: m/z (ES) 429 (MH)+; IC$_{50}$=9.6 nM 2Np: 4-tert-butyl-N-[(1S,3R)-3-(3-methyl-4H-1,2,4-triazol-4-yl)cyclohexyl]benzenesulfonamide: m/z (ES) 377 (MH)+; IC$_{50}$=51 nM 2Nq: 4-isopropyl-N-[(1S,3R)-3-(3-methyl-4H-1,2,4-triazol-4-yl)cyclohexyl]benzenesulfonamide: m/z (ES) 363 (MH)+; IC$_{50}$=28 nM 2Nr: 4-(5-cyclopropyl-1H-pyrazol-1-yl)-N-[(1S,3R)-3-(3-methyl-4H-1,2,4-triazol-4-yl)cyclohexyl]benzenesulfonamide: m/z (ES) 427 (MH)+; IC$_{50}$=56 nM 2Ns: 4-(3-cyclopropyl-1H-pyrazol-1-yl)-N-[(1S,3R)-3-(3-methyl-4H-1,2,4-triazol-4-yl)cyclohexyl]benzenesulfonamide: m/z (ES) 427 (MH)+; IC$_{50}$=30 nM 2Nt: 4-(4-methyl-1H-imidazol-1-yl)-N-[(1S,3R)-3-(3-methyl-4H-1,2,4-triazol-4-yl)cyclohexyl]benzenesulfonamide: m/z (ES) 401 (MH)+; IC$_{50}$=870 nM 2Nw: 4-butoxy-N-[(1S,3R)-3-(3-methyl-4H-1,2,4-triazol-4-yl)cyclohexyl]benzenesulfonamide: m/z (ES) 393 (MH)+; IC$_{50}$=2.8 nM 2Nac: N-[(1S,3R)-3-(3-methyl-4H-1,2,4-triazol-4-yl)cyclohexyl]-4-(4,4,4-trifluorobutoxy)benzenesulfonamide: m/z (ES) 447 (MH)+; IC$_{50}$=4.7 nM 2Nad: 4-(4-fluorobutoxy)-N-[(1S,3R)-3-(3-methyl-4H-1,2,4-triazol-4-yl)cyclohexyl]benzenesulfonamide: m/z (ES) 411 (MH)+; IC$_{50}$=11 nM 2Nae: 4-butoxy-2,5-difluoro-N-[(1S,3R)-3-(3-methyl-4H-1,2,4-triazol-4-yl)cyclohexyl]benzenesulfonamide: m/z (ES) 429 (MH)+; IC$_{50}$=5.4 nM 2Ow: 4-butoxy-N-[(1S,3R)-3-(3-cyclopropyl-4H-1,2,4-triazol-4-yl)cyclohexyl]benzenesulfonamide: m/z (ES) 419 (MH)+; IC$_{50}$=4.1 nM 2Oaf: 4-butoxy-N-[(1S,3R)-3-(3-cyclopropyl-4H-1,2,4-triazol-4-yl)cyclohexyl]-3-fluorobenzenesulfonamide: m/z (ES) 437 (MH)+; IC$_{50}$=1.7 nM 2Oag: 4-butoxy-N-[(1S,3R)-3-(3-cyclopropyl-4H-1,2,4-triazol-4-yl)cyclohexyl]-2-fluorobenzenesulfonamide: m/z (ES) 437 (MH)+; IC$_{50}$=7.2 nM 2Pk: N-[(1R,5S)-3,3-difluoro-5-(4H-1,2,4-triazol-4-yl)cyclohexyl]-3-ethylbenzenesulfonamide: m/z (ES) 371 (MH)+; IC$_{50}$=370 nM 2Ql: 4-(5-cyclopropyl-1,2,4-oxadiazol-3-yl)-N-[(1R,5S)-3,3-difluoro-5-(3-methyl-4H-1,2,4-triazol-4-yl)cyclohexyl]benzenesulfonamide: m/z (ES) 465 (MH)+; IC$_{50}$=8.2 nM 2Qw: 4-butoxy-N-[(1R,5S)-3,3-difluoro-5-(3-methyl-4H-1,2,4-triazol-4-yl)cyclohexyl]benzenesulfonamide: m/z (ES) 429 (MH)+; IC$_{50}$=4.2 nM 2Qad: N-[(1R,5S)-3,3-difluoro-5-(3-methyl-4H-1,2,4-triazol-4-yl)cyclohexyl]-4-(4-fluorobutoxy)-benzenesulfonamide: m/z (ES) 447 (MH)+; IC$_{50}$=8.8 nM

TABLE 2E

| Ex. #2R | Ex. #2S | R |
|---|---|---|
| a | a | $^c$Pr |
| b | b | $^c$Bu |
| c | c | 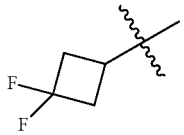 [SMILES: *C1CC(F)(F)C1] |

TABLE 2E-continued

| Ex. #2R | Ex. #2S | R |
|---|---|---|

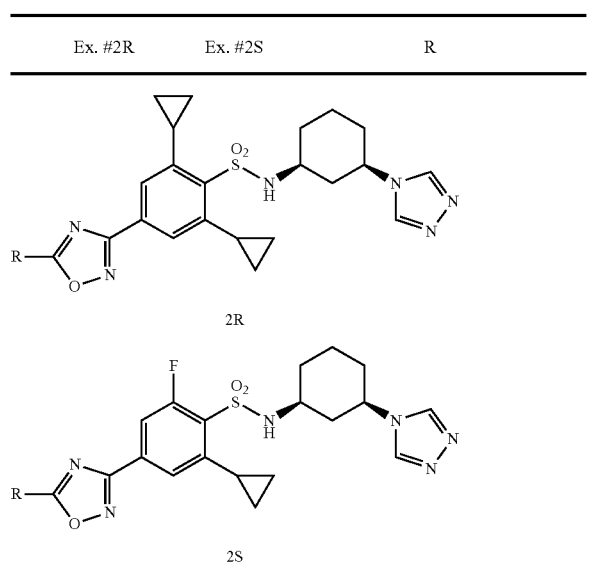

2R

2S

Table 2E. Parent Ion m/z (MH)+ and PAFR binding IC$_{50}$ data for compounds:

2Ra: 2,6-dicyclopropyl-4-(5-cyclopropyl-1,2,4-oxadiazol-3-yl)-N-[(1S,3R)-3-(4H-1,2,4-triazol-4-yl)cyclohexyl]benzenesulfonamide: m/z (ES) 495 (MH)+; IC$_{50}$=2.4 nM 2Rb: 4-(5-cyclobutyl-1,2,4-oxadiazol-3-yl)-2,6-dicyclopropyl-N-[(1S,3R)-3-(4H-1,2,4-triazol-4-yl)cyclohexyl]benzenesulfonamide: m/z (ES) 509 (MH)+; IC$_{50}$=0.1 nM 2Rc: 2,6-dicyclopropyl-4-[5-(3,3-difluorocyclobutyl)-1,2,4-oxadiazol-3-yl]-N-[(1S,3R)-3-(4H-1,2,4-triazol-4-yl)cyclohexyl]benzenesulfonamide: m/z (ES) 545 (MH)+; IC$_{50}$=2.9 nM 2Sa: 2-cyclopropyl-4-(5-cyclopropyl-1,2,4-oxadiazol-3-yl)-6-fluoro-N-[(1S,3R)-3-(4H-1,2,4-triazol-4-yl)cyclohexyl]benzenesulfonamide: m/z (ES) 473 (MH)+; IC$_{50}$=8.6 nM 2Sb: 4-(5-cyclobutyl-1,2,4-oxadiazol-3-yl)-2-cyclopropyl-6-fluoro-N-[(1S,3R)-3-(4H-1,2,4-triazol-4-yl)cyclohexyl]benzenesulfonamide: m/z (ES) 487 (MH)+; IC$_{50}$=2.6 nM

Example 3

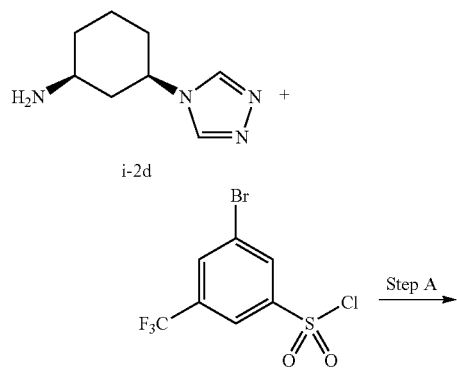

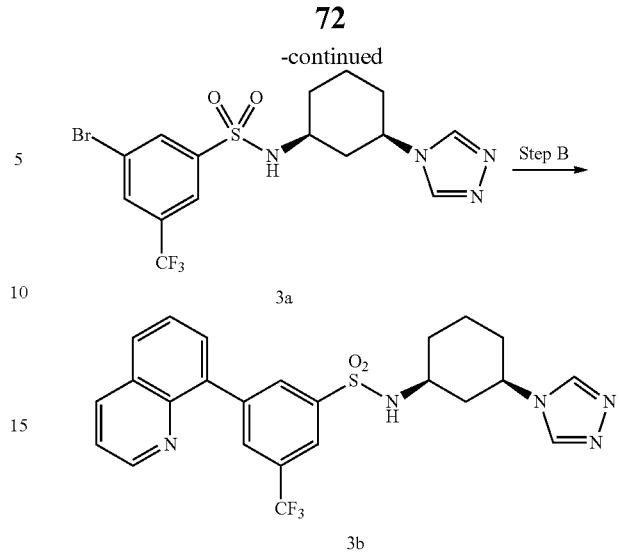

Step A: Preparation of 3-bromo-N-[(1S,3R)-3-(4H-1,2,4-triazol-4-yl)cyclohexyl]-5-(trifluoromethyl)benzenesulfonamide (3a)

Compound 3a was prepared following procedures similar to those as described in Example 1, step A, substituting 3-bromo-5-(trifluoromethyl)benzenesulfonyl chloride for i-5f. m/z (ES) 454 (MH)+. $^1$HNMR (500 MHz, CDCl$_3$) δ 8.33 (s, 2H), 8.25 (s, 1H), 8.15 (s, 1H), 7.97 (s, 1H), 4.16 (t, 1H, J=9.5 Hz), 3.43 (m, 1H), 2.43 (d, 1H, J=10.5 Hz), 2.16 (d, 1H, J=11.0 Hz), 1.96 (m, 2H), 1.81 (m, 1H), 1.62 (q, 1H, J≤12.0 Hz), 1.33-1.46 (m, 2H).

Step B: Preparation of 3-bromo-N-[(1S,3R)-3-(4H-1,2,4-triazol-4-yl)cyclohexyl]-5-(trifluoromethyl)benzenesulfonamide (3b)

A solution of [1,1'-bis(diphenylphosphino)ferrocene]dichloropalladium (81.0 mg, 0.099 mmol), 8-(4,4,5,5-tetramethyl-1,3,2-dioxaborolan-2-yl)quinoline (343 mg, 1.99 mmol), compound 3a (450 mg, 0.993 mmol) and sodium carbonate (993 μL of a 2.0 M aqueous solution) in DME (3.0 mL), water (1.0 mL) and EtOH (0.75 mL) was degassed via a stream of N$_2$ gas. The reaction vessel was sealed and heated in a microwave reactor at 120° C. for 15 min. After cooling to rt, the reaction mixture was diluted with EtOAc and stirred with activated charcoal for 10 min, then filtered. The filtrate was concentrated in vacuo, and the resulting crude residue was purified by column chromatography on silica gel (gradient elution, 0-10% MeOH/DCM as eluent) to afford the title compound 3b. m/z (ES) 502 (MH)+. $^1$HNMR (500 MHz, CD$_3$OD) δ 8.78 (s, 1H), 8.55 (s, 2H), 8.42 m, 2H), 8.21 (s, 1H), 8.18 (s, 1H), 8.06 (d, 1H, J=8.5 Hz), 7.87 (d, 1H, J=7.0 Hz), 7.87 (m, 1H), 7.74 (t, 1H, J=8.0 Hz), 4.28 (t, 1H, J=12.0 Hz), 3.90 (m, 1H), 2.32 (d, 1H, J=12.5 Hz), 2.06 (d, 1H, J=12.5 Hz), 1.92 (m, 2H), 1.61-1.73 (m, 2H), 1.44 (dq, 1H, J=3.0, 12.0 Hz), 1.31 (dq, 1H, J=4.0, 12.0 Hz). IC$_{50}$=0.9 nM

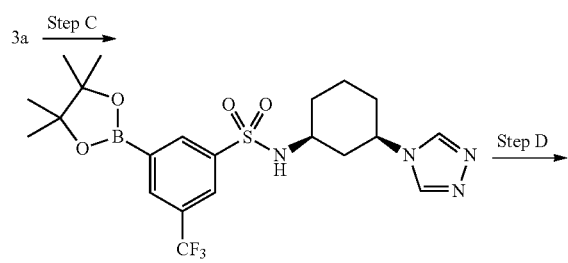

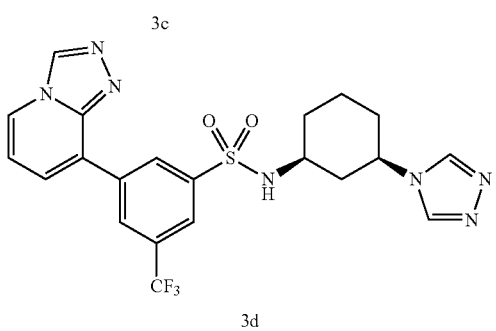

Step C: Preparation of 3-(4,4,5,5-tetramethyl-1,3,2-dioxaborolan-2-yl)-N-[(1S,3R)-3-(4H-1,2,4-triazol-4-yl)cyclohexyl]-5-(trifluoromethyl)benzenesulfonamide (3c)

Compound 3c was prepared following procedures similar to those described in Example 2, step C, substituting 3a for 2a. m/z (ES) 419 (MH-$C_6H_{12}$)$^+$.

Step D: Preparation of 3-[1,2,4]triazolo[4,3-a]pyridin-8-yl-N-[1S,3R)-3-(4H-1,2,4-triazol-4-yl)cyclohexyl]5-(trifluoromethyl)benzenesulfonamide (3d)

Compound 3d was prepared following procedures similar to those described in Example 2, step D, substituting 3c for 2c. m/z (ES) 492 (MH)$^+$. $IC_{50}$=3.1 nM.

Following procedures similar to those described above in Example 3, as well as any relevant previous scheme, the compounds in the Tables below could be prepared:

TABLE 3A

| Ex. #3A | Ex. #3B | Ex. #3C | Ex. #3D | $R^1$ | $R^2$ |
|---|---|---|---|---|---|
| a | a | a | a | Me | quinolin-8-yl |
| b | b | b | b |  | 4-F-phenyl |
| c | c | c | c | H | 4-F-phenyl |
| — | d | d | d |  | quinolin-8-yl |
| e | e | e | e |  | Ph |
| f | f | f | f |  | 6-MeO-pyridin-3-yl |
| g | g | g | g |  | 2-MeO-pyridin-3-yl |
| h | h | h | h |  | 5-cyclopropyl-1,2,4-oxadiazol-3-yl |
| i | i | i | i |  | 6-HO-pyridin-3-yl |
| j | j | j | j |  | 2-OH-pyridin-3-yl |
| k | k | k | k |  | 4-$F_3CO$-phenyl |
| l | l | l | l |  | 4-$F_3C$-phenyl |

TABLE 3A-continued
| Ex. #3A | Ex. #3B | Ex. #3C | Ex. #3D | R¹ | R² |
|---|---|---|---|---|---|
| m | m | m | m | | 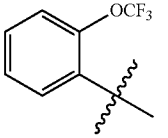 [SMILES: *c1ccccc1OC(F)(F)F] |
| n | n | n | n | | 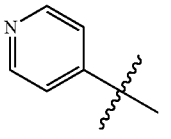 |
| o | o | o | o | | 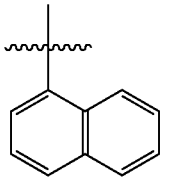 [SMILES: *c1cccc2ccccc12] |
| p | p | p | p | | 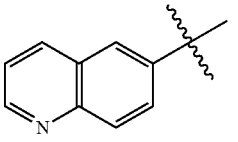 [SMILES: *c1ccc2ncccc2c1] |
| q | q | q | q | | 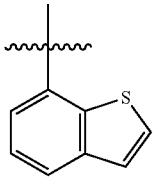 [SMILES: *c1cccc2ccsc12] |
| r | r | r | r | | 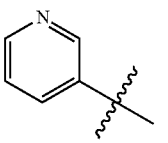 [SMILES: *c1cccnc1] |
| s | s | s | s | | 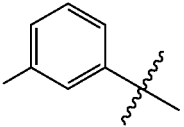 |
| t | t | t | t | | 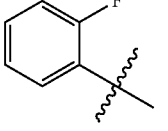 |
| u | u | u | u | | 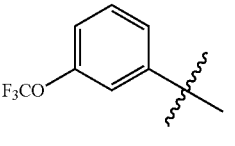 [SMILES: *c1cccc(OC(F)(F)F)c1] |
| v | v | v | v | | 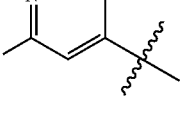 |
| w | w | w | w | | 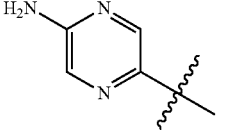 [SMILES: *c1cnc(N)cn1] |
| x | x | x | x | | 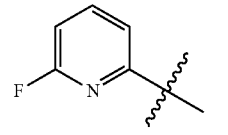 [SMILES: *c1cccc(F)n1] |
| y | y | y | y | | 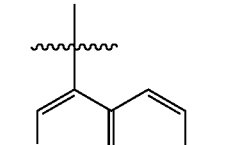 |
| z | z | z | z | | 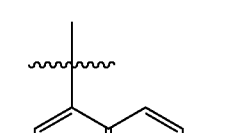 |
| aa | aa | aa | aa | | 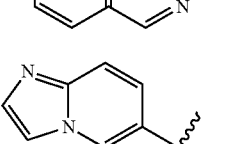 |
| ab | ab | ab | ab | | 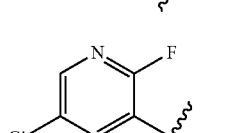 |
| ac | ac | ac | ac | | 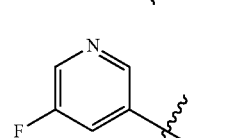 |
| ad | ad | ad | ad | | 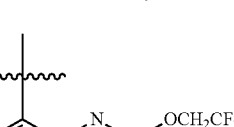 |
| ae | ae | ae | ae | | 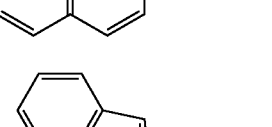 |

TABLE 3A-continued
| Ex. #3A | Ex. #3B | Ex. #3C | Ex. #3D | R¹ | R² |
|---|---|---|---|---|---|
| af | af | af | af | | 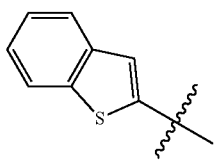 [SMILES: *c1cc2ccccc2s1] |
| ag | ag | ag | ag | | 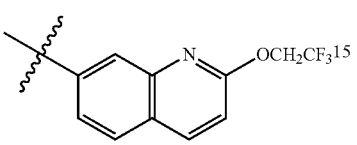 |
| ah | ah | ah | ah | | 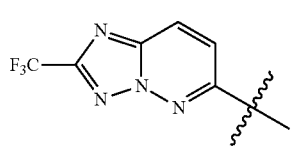 [SMILES: *c1ccc2nc(C(F)(F)F)nn2n1] |
| ai | ai | ai | ai | | 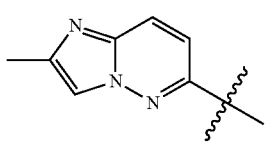 [SMILES: *c1ccc2nc(C)cn2n1] |
| aj | aj | aj | aj | | 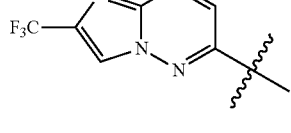 |
| ak | ak | ak | ak | | 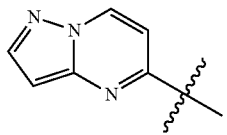 [SMILES: *c1ccn2nccc2n1] |
| al | al | al | al | | 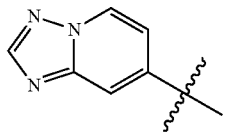 [SMILES: *c1ccn2ncnc2c1] |
| am | am | am | am | | 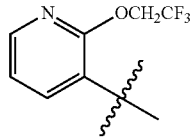 |
| an | an | an | an | | 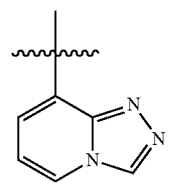 |
| ao | ao | ao | ao | | 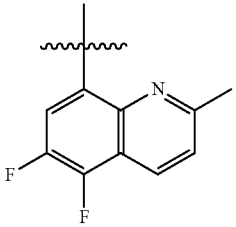 [SMILES: *c1cc(F)c(F)c2ccc(C)nc12] |
| ap | ap | ap | ap | | 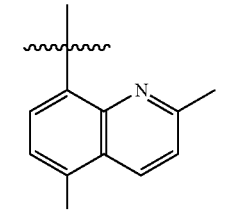 |
| aq | aq | aq | aq | | 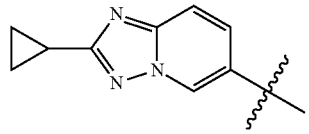 [SMILES: *c1ccc2nc(C3CC3)nn2c1] |
| ar | ar | ar | ar | | 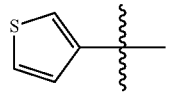 [SMILES: *c1ccsc1] |
| as | as | as | as | | 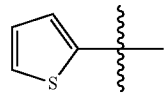 |
| at | at | at | at | | 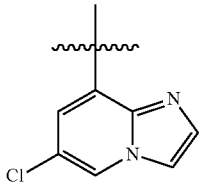 [SMILES: *c1cc(Cl)cn2ccnc12] |
| au | au | au | au | | 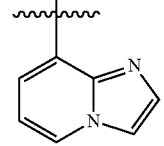 |
| av | av | av | av | | 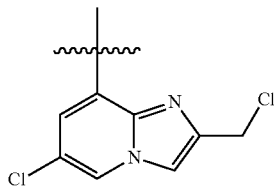 [SMILES: *c1cc(Cl)cn2cc(CCl)nc12] |

TABLE 3A-continued

| Ex. #3A | Ex. #3B | Ex. #3C | Ex. #3D | R¹ | R² |
|---|---|---|---|---|---|
| aw | aw | aw | aw | | imidazo[1,2-a]pyridine with Cl and CO₂Et substituents |
| ax | ax | ax | ax | | pyrazolo[1,5-a]pyrimidine |
| ay | ay | ay | ay | | F₃CH₂CO-pyridazine |
| az | az | az | az | | pyridazine |
| ba | ba | ba | ba | | pyridazine |

3A: structure with R², SO₂NH, cyclohexyl, triazole-R¹, CF₃

3B: structure with R², SO₂NH, cyclohexyl, triazole-R¹, Et

3C: structure with R², SO₂NH, difluorocyclohexyl, triazole-R¹, CF₃

3D: structure with R², SO₂NH, difluorocyclohexyl, triazole-R¹, Et

Table 3A. Parent Ion m/z (MH)⁺ and PAFR binding $IC_{50}$ data for compounds:

3Ca: N-[(1R,5S)-3,3-difluoro-5-(3-methyl-4H-1,2,4-triazol-4-yl)cyclohexyl]-3-quinolin-8-yl-5-(trifluoromethyl)benzenesulfonamide: m/z (ES) 552 (MH)⁺; $IC_{50}$=0.4 nM 3Da: N-[(1R,5S)-3,3-difluoro-5-(3-methyl-4H-1,2,4-triazol-4-yl)cyclohexyl]-3-ethyl-5-quinolin-8-ylbenzenesulfonamide: m/z (ES) 512 (MH)⁺; $IC_{50}$=1.8 nM 3Ab: 4'-fluoro-N-[(1S,3R)-3-(3-methyl-4H-1,2,4-triazol-4-yl)cyclohexyl]-5-(trifluoromethyl)biphenyl-3-sulfonamide: m/z (ES) 483 (MH)⁺; $IC_{50}$=4.8 nM 3Ac: 4'-fluoro-N-[(1S,3R)-3-(4H-1,2,4-triazol-4-yl)cyclohexyl]-5-(trifluoromethyl)biphenyl-3-sulfonamide: m/z (ES) 469 (MH)⁺; $IC_{50}$=6.2 nM 3 Cc: N-[(1R,5S)-3,3-difluoro-5-(4H-1,2,4-triazol-4-yl)cyclohexyl]-4)-fluoro-5-(trifluoromethyl)biphenyl-3-sulfonamide: m/z (ES) 505 (MH)⁺; $IC_{50}$=36 nM 3Bd: 3-ethyl-5-quinolin-8-yl-N-[(1S,3R)-3-(4H-1,2,4-triazol-4-yl)cyclohexyl]benzenesulfonamide: m/z (ES) 462 (MH)⁺; $IC_{50}$=0.9 nM 3Cd: N-[(1R,5S)-3,3-difluoro-5-(4H-1,2,4-triazol-4-yl)cyclohexyl]-3-quinolin-8-yl-5-(trifluoromethyl)benzenesulfonamide: m/z (ES) 538 (MH)⁺; $IC_{50}$=4.8 nM 3Ae: N-[(1S,3R)-3-(4H-1,2,4-triazol-4-yl)cyclohexyl]-5-(trifluoromethyl)biphenyl-3-sulfonamide: m/z (ES) 451 (MH)⁺; $IC_{50}$=5.9 nM 3Af: 3-(6-methoxypyridin-3-yl)-N-[(1S,3R)-3-(4H-1,2,4-triazol-4-yl)cyclohexyl]-5-(trifluoromethyl)benzenesulfonamide: m/z (ES) 482 (MH)⁺; $IC_{50}$=4.2 nM 3Ag: 3-(2-methoxypyridin-3-yl)-N-[(1S,3R)-3-(4H-1,2,4-triazol-4-yl)cyclohexyl]-5-(trifluoromethyl)benzenesulfonamide: m/z (ES) 482 (MH)⁺; $IC_{50}$=4.5 nM 3Ah: 3-(5-cyclopropyl-1,2,4-oxadiazol-3-yl)-N-[(1S,3R)-3-(4H-1,2,4-triazol-4-yl)cyclohexyl]-5-(trifluoromethyl)benzenesulfonamide: m/z (ES) 484 (MH)⁺; $IC_{50}$=7.8 nM 3Ai: 3-(6-hydroxypyridin-3-yl)-N-[(1S,3R)-3-(4H-1,2,4-triazol-4-yl)cyclohexyl]-5-(trifluoromethyl)benzenesulfonamide: m/z (ES) 468 (MH)⁺; $IC_{50}$=526 nM 3Aj: 3-(2-hydroxypyridin-3-yl)-N-[(1S,3R)-3-(4H-1,2,4-triazol-4-yl)cyclohexyl]-5-(trifluoromethyl)benzenesulfonamide: m/z (ES) 468 (MH)⁺; $IC_{50}$=12 nM 3Al: N-[(1S,3R)-3-(4H-1,2,4-triazol-4-yl)cyclohexyl]-4',5-bis(trifluoromethyl)biphenyl-3-sulfonamide: m/z (ES) 519 (MH)⁺; $IC_{50}$=8.1 nM 3Am: N-[(1S,3R)-3-(4H-1,2,4-triazol-4-yl)cyclohexyl]-2'-(trifluoromethoxy)-5-(trifluoromethyl)biphenyl-3-sulfonamide: m/z (ES) 535 (MH)⁺; $IC_{50}$=4.9 nM 3An: 3-pyridin-4-yl-N-[(1S,3R)-3-(4H-1,2,4-triazol-4-yl)cyclohexyl]-5-(trifluoromethyl)benzenesulfonamide: m/z (ES) 452 (MH)⁺; $IC_{50}$=36 nM 3Ao: 3-(1-naphthyl)-N-[(1S,3R)-3-(4H-1,2,4-triazol-4-yl)cyclohexyl]-5-(trifluoromethyl)benzenesulfonamide: m/z (ES) 501 (MH)$^+$; IC$_{50}$=15 nM 3Ap: 3-quinolin-6-yl-N-[(1S,3R)-3-(4H-1,2,4-triazol-4-yl)cyclohexyl]-5-(trifluoromethyl)benzenesulfonamide: m/z (ES) 502 (MH)$^+$; IC$_{50}$=3.3 nM 3Aq: 3-(1-benzothien-7-yl)-N-[(1S,3R)-3-(4H-1,2,4-triazol-4-yl)cyclohexyl]-5-(trifluoromethyl)benzenesulfonamide: m/z (ES) 507 (MH)$^+$; IC$_{50}$=7.0 nM 3Ar: 3-pyridin-3-yl-N-[(1S,3R)-3-(4H-1,2,4-triazol-4-yl)cyclohexyl]-5-(trifluoromethyl)benzenesulfonamide: m/z (ES) 452 (MH)$^+$; IC$_{50}$=32 nM 3As: 3'-fluoro-N-[(1S,3R)-3-(4H-1,2,4-triazol-4-yl)cyclohexyl]-5-(trifluoromethyl)biphenyl-3-sulfonamide: m/z (ES) 469 (MH)$^+$; IC$_{50}$=3.9 nM 3At: 2'-fluoro-N-[(1S,3R)-3-(4H-1,2,4-triazol-4-yl)cyclohexyl]-5-(trifluoromethyl)biphenyl-3-sulfonamide: m/z (ES) 469 (MH)$^+$; IC$_{50}$=5.4 nM 3Au: N-[(1S,3R)-3-(4H-1,2,4-triazol-4-yl)cyclohexyl]-3'-(trifluoromethoxy)-5-(trifluoromethyl)biphenyl-3-sulfonamide: m/z (ES) 535 (MH)$^+$; IC$_{50}$=2.1 nM 3Av: 3-(2-fluoropyridin-4-yl)-N-[(1S,3R)-3-(4H-1,2,4-triazol-4-yl)cyclohexyl]-5-(trifluoromethyl)benzenesulfonamide: m/z (ES) 470 (MH)$^+$; IC$_{50}$=15 nM 3Aw: 3-(5-aminopyrazin-2-yl)-N-[(1S,3R)-3-(4H-1,2,4-triazol-4-yl)cyclohexyl]-5-(trifluoromethyl)benzenesulfonamide: m/z (ES) 468 (MH)$^+$; IC$_{50}$=6.6 nM 3Ax: 3-(6-fluoropyridin-2-yl)-N-[(1S,3R)-3-(4H-1,2,4-triazol-4-yl)cyclohexyl]-5-(trifluoromethyl)benzenesulfonamide: m/z (ES) 470 (MH)$^+$; IC$_{50}$=4.6 nM 3 Ay: 3-isoquinolin-4-yl-N-[(1S,3R)-3-(4H-1,2,4-triazol-4-yl)cyclohexyl]-5-(trifluoromethyl)benzenesulfonamide: m/z (ES) 502 (MH)$^+$; IC$_{50}$=20 nM 3Az: 3-isoquinolin-5-yl-N-[(1S,3R)-3-(4H-1,2,4-triazol-4-yl)cyclohexyl]-5-(trifluoromethyl)benzenesulfonamide: m/z (ES) 502 (MH)$^+$; IC$_{50}$=10 nM 3Aaa: 3-imidazo[1,2-a]-pyridin-5-yl-N-[(1S,3R)-3-(4H-1,2,4-triazol-4-yl)cyclohexyl]-5-(trifluoromethyl)benzenesulfonamide: m/z (ES) 491 (MH)$^+$; IC$_{50}$=13 nM 3Aab: 3-(5-chloro-2-fluoropyridin-3-yl)-N-[(1S,3R)-3-(4H-1,2,4-triazol-4-yl)cyclohexyl]-5-(trifluoromethyl)benzenesulfonamide: m/z (ES) 504 (MH)$^+$; IC$_{50}$=4.0 nM 3Aac: 3-(5-fluoropyridin-3-yl)-N-[(1S,3R)-3-(4H-1,2,4-triazol-4-yl)cyclohexyl]-5-(trifluoromethyl)benzenesulfonamide: m/z (ES) 470 (MH)$^+$; IC$_{50}$=20 nM 3Aad: N-[(1S,3R)-3-(4H-1,2,4-triazol-4-yl)cyclohexyl]-3-[2-(2,2,2-trifluoroethoxy)quinolin-8-yl]-5-(trifluoromethyl)benzenesulfonamide: m/z (ES) 600 (MH)$^+$; IC$_{50}$=4.0 nM 3Aae: 3-(1-benzofuran-2-yl)-N-[(1S,3R)-3-(4H-1,2,4-triazol-4-yl)cyclohexyl]-5-(trifluoromethyl)benzenesulfonamide: m/z (ES) 491 (MH)$^+$; IC$_{50}$=1.8 nM 3Aaf: 3-(1-benzothien-2-yl)-N-[(1S,3R)-3-(4H-1,2,4-triazol-4-yl)cyclohexyl]-5-(trifluoromethyl)benzenesulfonamide: m/z (ES) 507 (MH)$^+$; IC$_{50}$=1.2 nM 3Aag: N-[(1S,3R)-3-(4H-1,2,4-triazol-4-yl)cyclohexyl]-3-[2-(2,2,2-trifluoroethoxy)quinolin-7-yl]-5-(trifluoromethyl)benzenesulfonamide: m/z (ES) 599 (MH)$^+$; IC$_{50}$=4.9 nM 3Aah: N-[(1S,3R)-3-(4H-1,2,4-triazol-4-yl)cyclohexyl]-3-(trifluoromethyl)-5-[2-(trifluoromethyl)[1,2,4]triazolo[1,5-b]pyridazin-6-yl]benzenesulfonamide: m/z (ES) 561 (MH)$^+$; IC$_{50}$=18 nM 3Aai: 3-(2-methylimidazo[1,2-b]pyridazin-6-yl)-N-[(1S,3R)-3-(4H-1,2,4-triazol-4-yl)cyclohexyl]-5-(trifluoromethyl)benzenesulfonamide: m/z (ES) 506 (MH)$^+$; IC$_{50}$=4.1 nM 3Aaj: N-[(1S,3R)-3-(4H-1,2,4-triazol-4-yl)cyclohexyl]-3-(trifluoromethyl)-5-[2-(trifluoromethyl)imidazo[1,2-b]pyridazin-6-yl]benzenesulfonamide: m/z (ES) 560 (MH)$^+$; IC$_{50}$=27 nM 3Aak: 3-pyrazolo[1,5-a]pyrimidin-5-yl-N-[(1S,3R)-3-(4H-1,2,4-triazol-4-yl)cyclohexyl]-5-(trifluoromethyl)benzenesulfonamide: m/z (ES) 492 (MH)$^+$; IC$_{50}$=3.6 nM 3Aal: 3-[1,2,4]triazolo[1,5-a]pyridin-7-yl-N-[(1S,3R)-3-(4H-1,2,4-triazol-4-yl)cyclohexyl]-5-(trifluoromethyl)benzenesulfonamide: m/z (ES) 492 (MH)$^+$; IC$_{50}$=42 nM 3Aam: N-[(1S,3R)-3-(4H-1,2,4-triazol-4-yl)cyclohexyl]-3-[2-(2,2,2-trifluoroethoxy)pyridin-3-yl]-5-(trifluoromethyl)benzenesulfonamide: m/z (ES) 550 (MH)$^+$; IC$_{50}$=3.2 nM 3Bam: 3-ethyl-N-[(1S,3R)-3-(4H-1,2,4-triazol-4-yl)cyclohexyl]-5-[2-(2,2,2-trifluoroethoxy)pyridin-3-yl]benzenesulfonamide: m/z (ES) 510 (MH)$^+$; IC$_{50}$=9.5 nM 3Aan: 3-[1,2,4]triazolo[4,3-a]pyridin-8-yl-N-[(1S,3R)-3-(4H-1,2,4-triazol-4-yl)cyclohexyl]-5-(trifluoromethyl)benzenesulfonamide: m/z (ES) 492 (MH)$^+$ 3Aap: 3-(5-fluoro-2-methylquinolin-8-yl)-N-[(1S,3R)-3-(4H-1,2,4-triazol-4-yl)cyclohexyl]-5-(trifluoromethyl)benzenesulfonamide: m/z (ES) 534 (MH)$^+$; IC$_{50}$=2.1 nM 3Aaq: 3-(2-cyclopropyl[1,2,4]triazolo[1,5-a]pyridin-6-yl)-N-[(1S,3R)-3-(4H-1,2,4-triazol-4-yl)cyclohexyl]-5-(trifluoromethyl)benzenesulfonamide: m/z (ES) 532 (MH)$^+$; IC$_{50}$=20 nM 3Aar: 3-(3-thienyl)-N-[(1S,3R)-3-(4H-1,2,4-triazol-4-yl)cyclohexyl]-5-(trifluoromethyl)benzenesulfonamide: m/z (ES) 457 (MH)$^+$; IC$_{50}$=9.2 nM 3Aas: 3-(2-thienyl)-N-[(1S,3R)-3-(4H-1,2,4-triazol-4-yl)cyclohexyl]-5-(trifluoromethyl)benzenesulfonamide: m/z (ES) 457 (MH)$^+$; IC$_{50}$=3.8 nM 3Aat: 3-(6-chloroimidazo[1,2-a]pyridin-8-yl)-N-[(1S,3R)-3-(4H-1,2,4-triazol-4-yl)cyclohexyl]-5-(trifluoromethyl)benzenesulfonamide: m/z (ES) 525 (MH)$^+$; IC$_{50}$=2.7 nM 3Aau: 3-imidazo[1,2-a]pyridin-8-yl-N-[(1S,3R)-3-(4H-1,2,4-triazol-4-yl)cyclohexyl]-5-(trifluoromethyl)benzenesulfonamide: m/z (ES) 491 (MH)$^+$; IC$_{50}$=1.4 nM 3Bau: 3-ethyl-5-imidazo[1,2-a]pyridin-8-yl-N-[(1S,3R)-3-(4H-1,2,4-triazol-4-yl)cyclohexyl]-5-(trifluoromethyl)benzenesulfonamide: m/z (ES) 451 (MH)$^+$; IC$_{50}$=0.8 nM 3Aav: 3-[6-chloro-2-(chloromethyl)imidazo[1,2-a]pyridin-8-yl]-N-[(1S,3R)-3-(4H-1,2,4-triazol-4-yl)cyclohexyl]-5-(trifluoromethyl)benzenesulfonamide: m/z (ES) 573 (MH)$^+$; IC$_{50}$=22 nM 3Bav: 3-[6-chloro-2-(chloromethyl)imidazo[1,2-a]pyridin-8-yl]-5-ethyl-N-[(1S,3R)-3-(4H-1,2,4-triazol-4-yl)cyclohexyl]benzenesulfonamide: m/z (ES) 485 (MH)$^+$; IC$_{50}$=2.6 nM 3Aaw: ethyl 6-chloro-8-[3-({[(1S,3R)-3-(4H-1,2,4-triazol-4-yl)cyclohexyl]amino}sulfonyl)-5-(trifluoromethyl)phenyl]imidazo[1,2-a]pyridine-2-carboxylate: m/z (ES) 597 (MH)$^+$; IC$_{50}$=0.5 nM 3Bax: 3-ethyl-5-pyrazolo[1,5-a]pyrimidin-6-yl-N-[(1S,3R)-3-(4H-1,2,4-triazol-4-yl)cyclohexyl]benzenesulfonamide: m/z (ES) 452 (MH)$^+$; IC$_{50}$=22 nM 3Bay: 3-ethyl-N-[(1S,3R)-3-(4H-1,2,4-triazol-4-yl)cyclohexyl]-5-[6-(2,2,2-trifluoroethoxy)pyridazin-3-yl]benzenesulfonamide: m/z (ES) 511 (MH)$^+$; IC$_{50}$=5.7 nM 3Baz: 3-ethyl-5-pyridazin-4-yl-N-[(1S,3R)-3-(4H-1,2,4-triazol-4-yl)cyclohexyl]benzenesulfonamide: m/z (ES) 414 (MH)$^+$; IC$_{50}$=208 nM 3Bba: 3-ethyl-5-pyridazin-3-yl-N-[(1S,3R)-3-(4H-1,2,4-triazol-4-yl)cyclohexyl]benzenesulfonamide: m/z (ES) 414 (MH)$^+$

TABLE 3B

| Ex. #3E | Ex. #3F | Ex. #3G | Ex. #3H | R₁ |
|---------|---------|---------|---------|-----|
| a | a | a | a | Ph |
| b | b | b | b | 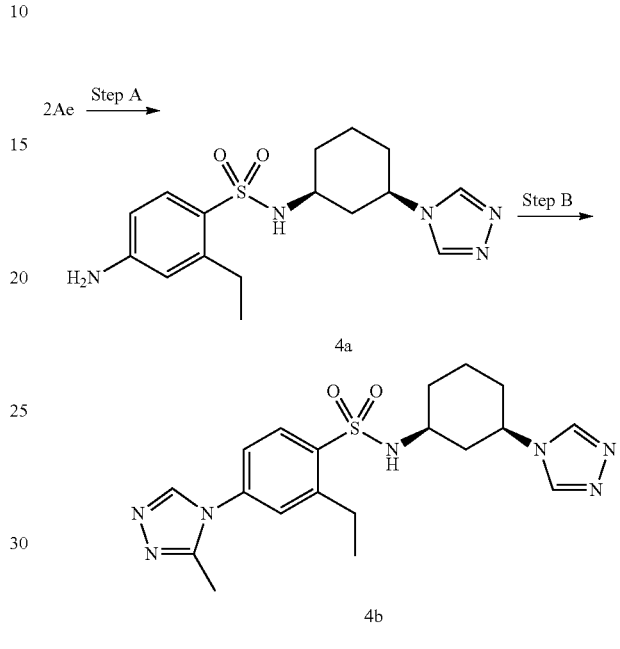 |
| c | c | c | c | |

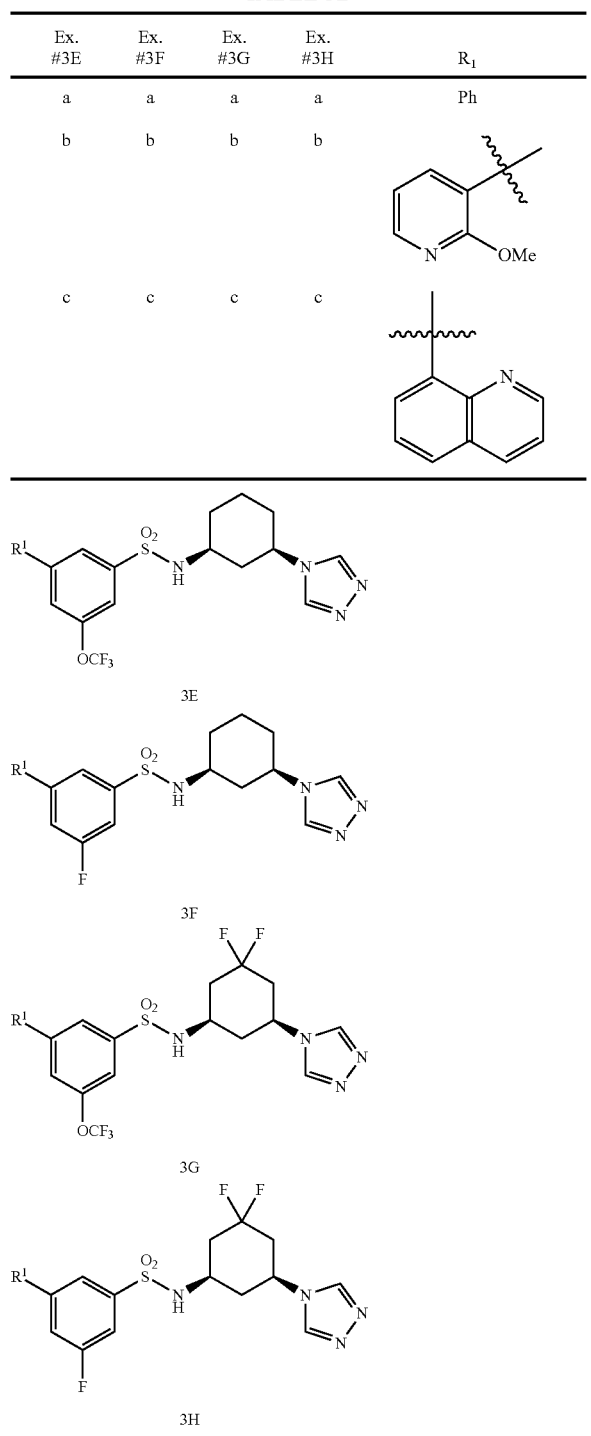

Table 313. Parent Ion m/z (MH)⁺ and PAFR binding IC₅₀ data for compounds:
3Ea: N-[(1S,3R)-3-(4H-1,2,4-triazol-4-yl)cyclohexyl]-5-(trifluoromethoxy)biphenyl-3-sulfonamide: m/z (ES) 468 (MH)⁺; IC$_{50}$=10 nM
3Eb: 3-(2-methoxypyridin-3-yl)-N-[(1S,3R)-3-(4H-1,2,4-triazol-4-yl)cyclohexyl]-5-(trifluoromethoxy)benzenesulfonamide: m/z (ES) 498 (MH)⁺; IC$_{50}$=13 nM
3Fa: 5-fluoro-N-[(1S,3R)-3-(4H-1,2,4-triazol-4-yl)cyclohexyl]biphenyl-3-sulfonamide: m/z (ES) 401 (MH)⁺; IC$_{50}$=10 nM
3Fb: 3-fluoro-5-(2-methoxypyridin-3-yl)-N-[(1S,3R)-3-(4H-1,2,4-triazol-4-yl)cyclohexyl]benzenesulfonamide: m/z (ES) 432 (MH)⁺; IC$_{50}$=9 nM
3Fc: 3-fluoro-5-quinolin-8-yl-N-[(1S,3R)-3-(4H-1,2,4-triazol-4-yl)cyclohexyl]benzenesulfonamide: m/z (ES) 452 (MH)⁺; IC$_{50}$=1 nM

Example 4

Step A: Preparation of 4-amino-2-ethyl-N-[(1S,3R)-3-(4H-1,2,4-triazol-4-yl)cyclohexyl]benzenesulfonamide (4a)

Palladium on carbon (44.0 mg, 0.413 mmol, 10% w/w on activated carbon) was added to a stirred solution of 2Ae (102 mg, 0.269 mmol) in EtOH (3.0 mL), and the resulting mixture was hydrogenated at atmospheric pressure. After the reaction was deemed to be complete, the reaction mixture was filtered through a short column of Celite®, eluting copiously with MeOH. The filtrate was concentrated in vacuo, and the resulting crude residue was purified by column chromatography on silica gel (gradient elution, 0-6% MeOH/DCM as eluent) to afford the title compound 4a. m/z (ES) 350 (MH)⁺

Step B: Preparation of 2-ethyl-4-(3-methyl-4H-1,2,4-triazol-4-yl)-N-[(1S,3R)-3-(4H-1,2,4-triazol-4-yl)cyclohexyl]benzenesulfonamide (4b)

A mixture of N-acetyl-N,N-dimethylhydrazonoformamide (35.0 mg, 0.270 mmol) and 4a (38.0 mg, 0.109 mmol) in acetic acid (500 µL) was placed in a sealed tube and heated in a microwave reactor at 150° C. for 30 min. After cooling to rt, the reaction mixture was quenched with satd. aq. NaHCO₃, neutralized with 2M HCl and extracted with EtOAc. The combined organics were concentrated in vacuo, and the crude residue was purified by column chromatography on silica gel (gradient elution, 0-16% MeOH/DCM to afford the title compound, 4b. m/z (ES) 416 (MH)⁺; IC$_{50}$=9800 nM

Example 5

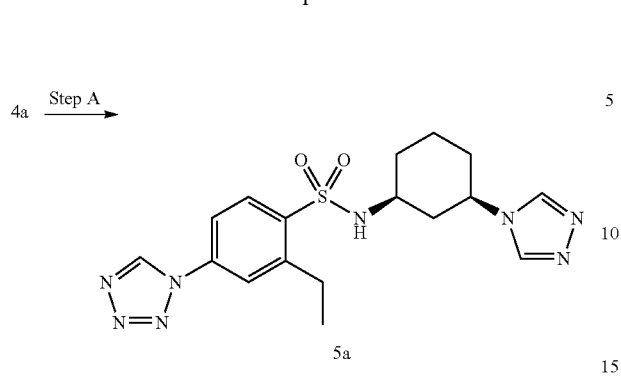

Step A: Preparation of 2-ethyl-4-(1H-tetrazol-1-yl)-N-[(1S,3R)-3-(4H-1,2,4-triazol-4-yl)cyclohexyl]benzenesulfonamide (5a)

Triethyl orthoformate (70.0 μL, 0.420 mmol) was added to a mixture of 4a (33.0 mg, 0.094 mmol) and sodium azide (20.0 mg, 0.308 mmol) in acetic acid (1.00 mL), and the resulting mixture was heated to 90° C. After 15 h, the reaction mixture was cooled to rt, quenched with satd. aq. NaHCO$_3$ and extracted with EtOAc. The combined organics were washed with brine, dried (Na$_2$SO$_4$), filtered and concentrated in vacuo. The crude residue was purified by column chromatography on silica gel (gradient elution, 0-15% MeOH/DCM as eluent) to afford the title compound, 5a. m/z (ES) 403 (MH)$^+$; IC$_{50}$=815 nM

Example 6

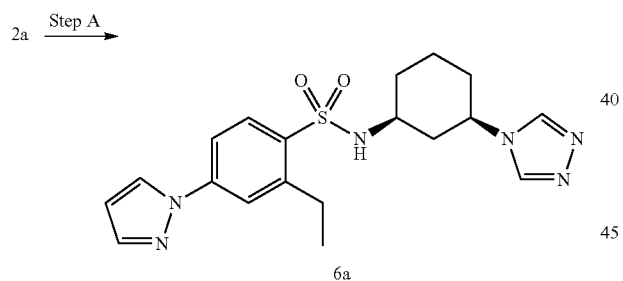

Step A: Preparation of 2-ethyl-4-(1H-pyrazol-1-yl)-N-[(1S,3R)-3-(4H-1,2,4-triazol-4-yl)cyclohexyl]benzenesulfonamide (6a)

A mixture of 2a (39.6 mg, 0.096 mmol), pyrazole (49.0 mg, 0120 mmol), copper (1) oxide (16.0 mg, 0.112 mmol), salicylaldoxime (19.0 mg, 0.139 mmol) and cesium carbonate (255 mg, 0.783 mmol) in acetonitrile (500 μL) was placed in a sealed tube and heated in a microwave reactor at 120° C. for 30 min. After cooling to room temperature, the reaction mixture was partitioned between EtOAc and brine. The layers were separated, and the aqueous layer was extracted with EtOAc. The combined organics were filtered through a short column of Celite®, eluting copiously with EtOAc, and concentrated in vacuo. The crude residue was purified by preparative thin layer chromatography on silica gel (10% MeOH/DCM as eluent) to afford the title compound, 6a. m/z (ES) 401 (MH); IC$_{50}$=68 nM

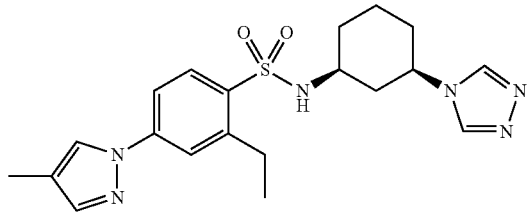

Preparation of 2-ethyl-4-(4-methyl-1H-pyrazol-1-yl)-N-[(1S,3R)-3-(4H-1,2,4-triazol-4-yl)cyclohexyl]benzenesulfonamide (6b)

Compound 6b was prepared following procedures similar to those described above, substituting 4-methylpyrazole for pyrazole. m/z (ES) 415 (MH)$^+$; IC$_{50}$=25 nM

Example 7

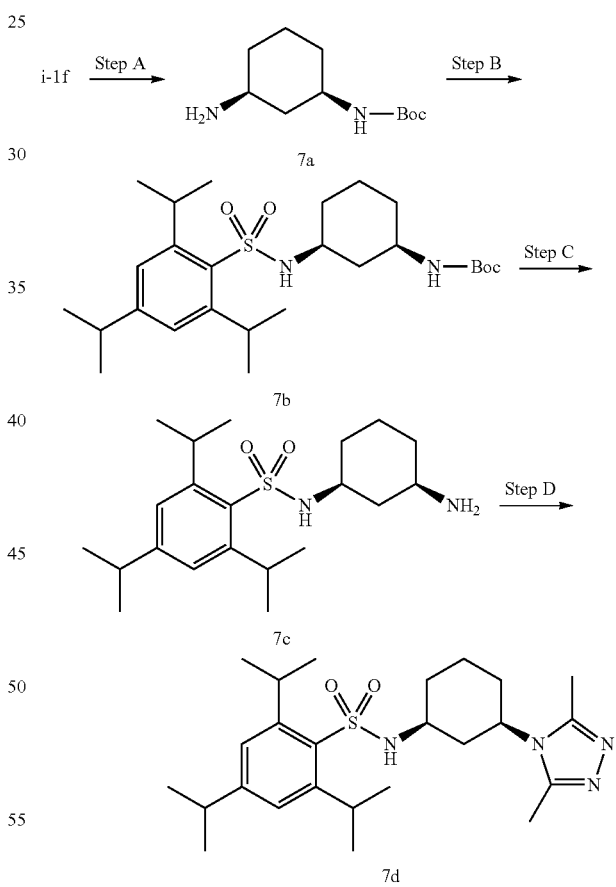

Step A: Preparation of tert-butyl[(1R,3S)-3-aminocyclohexyl]carbamate (7a)

Compound 7a was prepared following procedures similar to those described previously in Scheme i-1, step D, substituting i-1f for i-1c. m/z (ES) 215 (MH)$^+$

Step B: Preparation of tert-butyl ((1R,3S)-3-{[(2,4,6-triisopropylphenyl)sulfonyl]amino}cyclohexyl)carbamate (7b)

Compound 7b was prepared following procedures similar to those described previously in Example 1, step A, substituting 7a for i-2d and 2,4,6-triisopropylbenzenesulfonyl chloride for i-5f, respectively. m/z (ES) 503 (MH+Na)+

Step C: Preparation of N-[(1R,3S)-3-aminocyclohexyl]-2,4,6-triisopropylbenzenesulfonamide (7c)

Compound 7c was prepared following procedures similar to those described previously in Scheme i-1, step B, substituting 7b for i-1a. m/z (ES) 381 (MH)+

Step D: Preparation of N-[(1S,3R)-3-(3,5-dimethyl-4H-1,2,4-triazol-4-yl)cyclohexyl]-2,4,6-triisopropylbenzenesulfonamide (7d)

A mixture of N,N-dimethylacetamide dimethylacetal (21.0 mg, 0.158 mmol) and acetic hydrazide (10.7 mg, 0.145 mmol) in acetonitrile (2.0 mL) was heated to 50° C. for 30 min, at which point, compound 7c (50.0 mg, 0.131 mmol) was added, and the resulting mixture was heated to 100° C. overnight. After cooling to rt, the reaction mixture was partitioned between EtOAc and water. The layers were separated, and the aq. layer was extracted with EtOAc. The combined organics were washed with brine, dried ($Na_2SO_4$), filtered and concentrated in vacuo. The crude residue was purified by preparative thin layer chromatography on silica gel (10% MeOH/DCM as eluent) to afford the title compound, 7d. m/z (ES) 461 (MH)+; $IC_{50}$=9.8 nM

Example 8

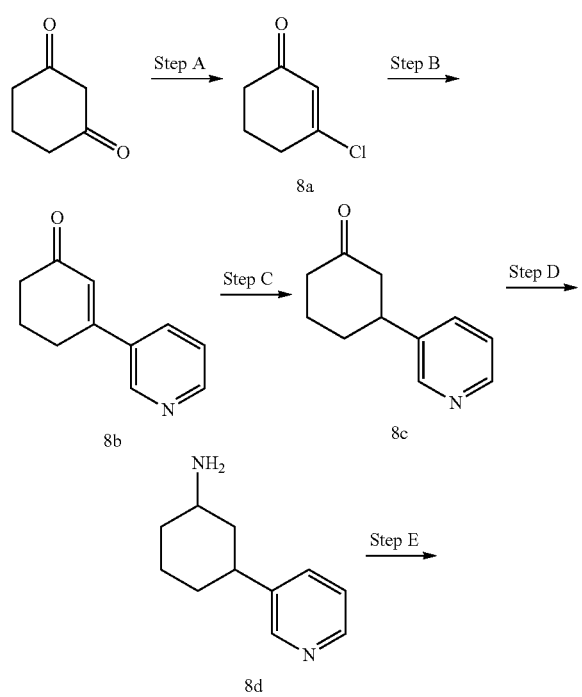

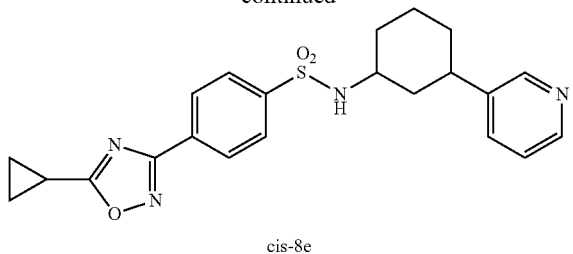

cis-8e

Step A: Preparation of 3-chlorocyclohex-2-en-1-one (8a.

Oxalyl chloride (2.77 mL, 31.6 mmol) was added to a stirred solution of 1,3-cyclohexanedione (3.73 g, 33.3 mmol) and DMF (2.58 mL, 33.3 mmol) in DCM (150 mL) at 0° C. After the reaction was deemed complete, the reaction mixture was partitioned between ether and water. The layers were separated, and the organics were dried ($MgSO_4$), filtered and concentrated in vacuo to afford the title compound, 8a, which was carried on directly to the next reaction.

Step B: Preparation of 3-pyridin-3-ylcyclohex-2-en-1-one (8b)

[1,1'-bis(diphenylphosphino)ferrocene]dichloropalladium-DCM complex (313 mg, 0.383 mmol) was added to a stirred mixture of 8a (500 mg, 3.83 mmol), pyridin-3-ylboronic acid (565 mg, 4.60 mmol) and sodium carbonate (2.87 mL of a 2M aq. solution, 5.74 mmol) in dioxane (14.0 mL) and water (2.00 mL). The resulting mixture was degassed and heated to 95° C. After 7 h, the reaction mixture was cooled to rt, diluted with EtOAc, filtered through a short column of Celite®, eluting copiously with EtOAc. The organics were washed with brine, dried (Na2SO4), filtered and concentrated in vacuo. The crude residue was purified by column chromatography on silica gel (0-90% EtOAc/hexanes as eluent) to afford the title compound, 8b. m/z (ES) 174 (MH)+

Step C: Preparation of 3-pyridin-3-ylcyclohexanone (8c)

A mixture of 8b (275 mg, 1.59 mmol) and rhodium (325 mg, 0.158 mmol, 5% wt. on activated basic alumina) in EtOH (16.0 mL) was hydrogenated at atmospheric pressure while stirring at rt. After the reaction was deemed to be complete, the reaction mixture was filtered through a short column of Celite®, eluting copiously with EtOAc, and the combined organics were concentrated in vacuo to afford the title compound, 8c. m/z (ES) 176 (MH)+

Step D: Preparation of 3-pyridin-3-ylcyclohexanamine (8d)

Hydroxylamine hydrochloride (67.7 mg, 0.975 mmol) was added to a stirred mixture of 8c (122 mg, 0.696 mmol) and potassium carbonate (96.0 mg, 0.696 mmol) in MeOH (3.00 mL) and water (600 µl). After the reaction was deemed to be complete, the reaction mixture was partially concentrated in vacuo and partitioned between EtOAc and brine. The layers were separated, and the aq. layer was extracted with EtOAc. The combined organics were dried (Na$_2$SO$_4$), filtered and concentrated in vacuo to afford a crude residue (m/z (ES) 191 (MH)$^+$), which was dissolved in THF (3.50 mL) and cooled to 0° C. Lithium aluminum hydride (106 mg, 2.78 mmol) was added in several portions, and after the reaction was deemed to be complete, 1N NaOH was added. The resulting mixture was saturated with NaCl(s) and extracted with EtOAc. The combined organics were dried (Na$_2$SO$_4$), filtered and concentrated in vacuo to afford the title compound, 8d. m/z (ES) 177 (MH)$^+$

Step E: Preparation of 4-(5-cyclopropyl-1,2,4-oxadiazol-3-yl)-N-(3-pyridin-cis-3-ylcyclohexyl)benzenesulfonamide (8e)

Compound 8e was prepared following procedures similar to those described previously in Example 1, step A, substituting 8e for i-2d. m/z (ES) 453 (MH)$^+$; IC$_{50}$=1.9 nM

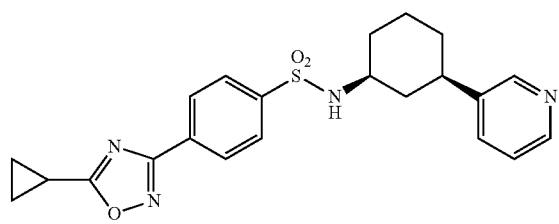

8f

Compound 8f was isolated following chiral chromatography using conditions similar to those described previously in Scheme i-1, step E. m/z (ES) 453 (MH)$^+$; IC$_{50}$=0.8 nM

Example 9

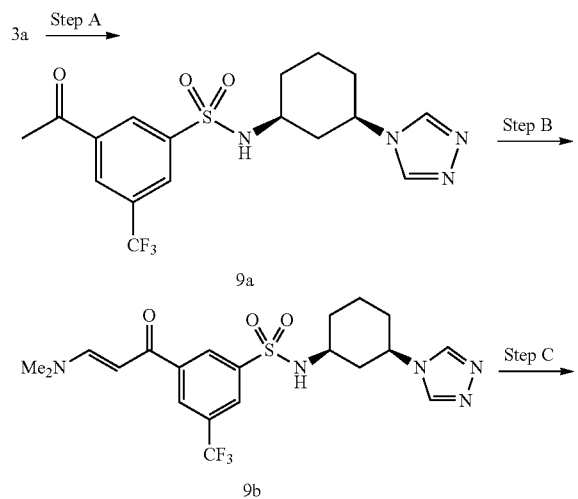

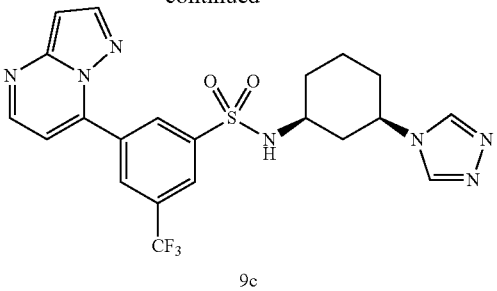

9c

Step A: Preparation of 3-acetyl-N-[(1S,3R)-3-(4H-1,2,4-triazol-4-yl)cyclohexyl]-5-(trifluoromethyl)benzenesulfonamide (9a)

Palladium acetate (9.9 mg, 0.044 mmol) was added to a stirred solution of 3a (100 mg, 0.221 mmol), n-butylvinyl ether (221 mg, 2.206 mmol) and triethylamine (92.0 μL, 0.662 mmol) in DMF (2.00 mL), and the resulting mixture was degassed and heated to 80° C. After 6 h, the reaction mixture was cooled to 0° C., 1M HCl was added, and the resulting mixture was allowed to warm to rt and stirred overnight. The reaction mixture was quenched with satd. aq. NaHCO$_3$ and extracted with EtOAc. The combined organics were dried (MgSO$_4$), filtered and concentrated in vacuo. The crude residue was purified by preparative thin layer chromatography on silica gel (10% MeOH/DCM as eluent) to afford the title compound, 9a. m/z (ES) 417 (MH)$^+$

Step B: Preparation of 3-[(2E)-3-(dimethylamino)prop-2-enoyl]-N-[(1S,3R)-3-(4H-1,2,4-triazol-4-yl)cyclohexyl]-5-(trifluoromethyl)benzenesulfonamide (9b)

N,N,-Dimethylformamide dimethyl acetal (200 μL, 1.49 mmol) was added to a stirred solution of 9a (100 mg, 0.240 mmol) in EtOH (1.50 mL). The mixture was placed in a sealed tube and heated in a microwave reactor at 100° C. for 2 h. After cooling to rt, the reaction mixture was concentrated in vacuo, and the resulting crude residue was purified by preparative thin layer chromatography on silica gel (10% MeOH/DCM as eluent) to afford the title compound, 9b. m/z (ES) 472 (MH)$^+$

Step C: Preparation of 3-pyrazolo[1,5-a]pyrimidin-7-yl-N-[(1S,3R)-3-(4H-1,2,4-triazol-4-yl)cyclohexyl]-5-(trifluoromethyl)benzenesulfonamide (9c)

A mixture of 9b (40.0 mg, 0.085 mmol) and 3-aminopyrazole (8.5 mg, 0.102 mmol) in acetic acid (1.50 mL) was placed in a sealed tube and heated in a microwave reactor at 110° C. for 20 min. After cooling to rt, the reaction mixture was concentrated in vacuo, resuspended in 10% NH$_4$OH/MeOH and reconcentrated. The crude residue was purified by preparative thin layer chromatography on silica gel (10% MeOH/DCM as eluent) to afford the title compound, 9c. m/z (ES) 492 (MH)$^+$; IC$_{50}$=5.9 nM Following procedures similar to those described above in Example 9, as well as any relevant previous scheme, the compounds in the Table below could be prepared:

Table 9. Parent Ion m/z (MH)+ and PAFR binding IC50 data for compounds:

9Aa: 3-(2-cyclopropylpyrimidin-4-yl)-N-[(1R,5S)-3,3-difluoro-5-(3-methyl-4H-1,2,4-triazol-4-yl)cyclohexyl]-5-(trifluoromethyl)benzenesulfonamide: m/z (ES) 493 (MH)+; IC$_{50}$=2.2 nM 9Ab: 3-(2-aminopyrimidin-4-yl)-N-[(1R,5S)-3,3-difluoro-5-(3-methyl-4H-1,2,4-triazol-4-yl)cyclohexyl]-5-(trifluoromethyl)benzenesulfonamide: m/z (ES) 468 (MH)+; IC$_{50}$=15 nM 9Ac: 3-[1,2,4]triazolo[1,5-a]pyrimidin-7-yl-N-[(1R,5S)-3,3-difluoro-5-(3-methyl-4H-1,2,4-triazol-4-yl)cyclohexyl]-5-(trifluoromethyl)benzenesulfonamide: m/z (ES) 493 (MH)+; IC$_{50}$=86 nM 9Ad: 3-isoxazol-5-yl-N-[(1R,5S)-3,3-difluoro-5-(3-methyl-4H-1,2,4-triazol-4-yl)cyclohexyl]-5-(trifluoromethyl)benzenesulfonamide: m/z (ES) 443 (MH)+; IC$_{50}$=34 nM 9Ae: 3-(1H)-pyrazol-5-yl)-N-[(1R,5S)-3,3-difluoro-5-(3-methyl-4H-1,2,4-triazol-4-yl)cyclohexyl]-5-(trifluoromethyl)benzenesulfonamide: m/z (ES) 441 (MH)+; IC$_{50}$=18 nM 9Af: 3-(2-cyclopropylpyrazolo[1,5-a]pyrimidin-7-yl)-N-[(1R,5S)-3,3-difluoro-5-(3-methyl-4H-1,2,4-triazol-4-yl)cyclohexyl]-5-(trifluoromethyl)benzenesulfonamide: m/z (ES) 532 (MH)+; IC$_{50}$=5.1 nM

The invention claimed is:

1. A compound of formula I or a pharmaceutically acceptable salt thereof:

wherein
- $R_1$, and $R_2$ are each independently selected from the group consisting of H, halogen, small alkyl, small alkoxy, small cycloalkyl, small haloalkyl, small haloalkoxy, or —$OC_1$-$C_4$alkyl, optionally substituted with fluoro;
- $R_3$ is selected from the group consisting of substituted or unsubstituted mono- or polycyclic aryl or heteroaryl, H, halogen, amide, $OCF_3$, small alkyl, small cycloalkyl, or small alkoxy;
- $R_4$ and $R_5$ are H, OH, or F, with the proviso that when $R_4$ is OH, then $R_5$ is H; and
- $R^A$ is selected from the group consisting of 3-pyridyl;

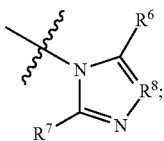

wherein $R^6$ and $R^7$ are each independently selected from the group consisting of H, small alkyl, cycloalkyl, hydroxymethyl, and carboxymethyl and $R^8$ is independently selected from N or CH;

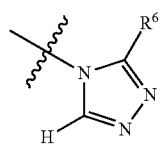

wherein $R_6$ is H or small alkyl; and

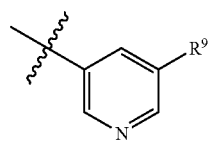

wherein $R_9$ is H, F, small alkyl, OH or $NH_2$.

2. The compound of claim 1 of structural Formula II, or a pharmaceutically acceptable salt thereof:

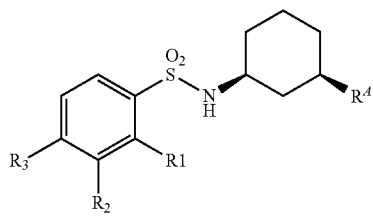

wherein
- $R_1$ is H, F, small alkyl, small cycloalkyl, small alkoxy, or $OCF_3$;
- $R_2$ is H, F, small alkyl or small alkoxy; and
- $R_3$ is substituted or unsubstituted 5 or 6-membered heteroaryl or 9- or 10-membered heteroaryl, H, halo, amide, $OCF_3$, or small alkoxy.

3. The compound of claim 1 of structural Formula III or a pharmaceutically acceptable salt thereof:

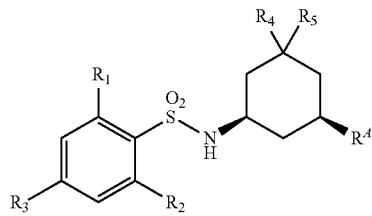

wherein
- $R_1$ is H, F, small alkyl, small cycloalkyl, small alkoxy, small haloalkyl, or $OCF_3$;
- $R_2$ is H, small alkyl, small alkoxy;
- $R_3$ is small alkyl, small alkoxy, or substituted or unsubstituted 5 or 6 membered aryl or heteroaryl; and
- $R_4$ and $R_5$ are H, OH, or F, with the proviso that when $R_4$ is OH, then $R_5$ is H.

4. The compound of claim 1 of structural Formula IV or a pharmaceutically acceptable salt thereof:

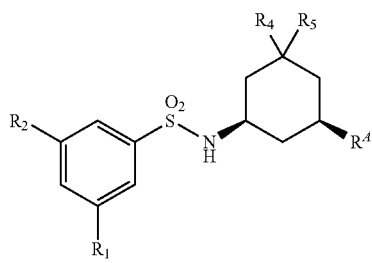

wherein
- $R_1$ is small alkyl, halo, small haloalkyl, small alkoxy or small haloalkoxy;
- $R_2$ is halogen, small alkoxy, or $OCF_3$;
- $R_4$ and $R_5$ are H, OH, or F, with the proviso that when $R_4$ is OH, then $R_5$ is H; and
- $R_3$ is substituted or unsubstituted mono- or polycyclic aryl or heteroaryl, H, halogen, amide, $OCF_3$, small alkyl, small cycloalkyl, or small alkoxy.

5. The compound of claim 1 of structural Formula V or a pharmaceutically acceptable salt thereof:

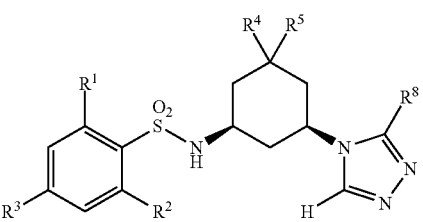

wherein
- $R_1$, $R_2$ and $R_3$ are small alkyl, or small cycloalkyl;
- $R_4$ and $R_5$ are H, OH, or F, with the proviso that when $R_4$ is OH, then $R_5$ is H; and
- $R_6$ is small alkyl or small cycloalkyl.

6. The compound of claim I selected from the group consisting of:
- 4-(5-cyclopropyl-1,2,4-oxadiazol-3-yl)-2-ethyl-N-[(1S,3R)-3-(4H-1,2,4-triazol-4-yl)cyclohexyl]benzenesulfonamide;

4-bromo-2-ethyl-N-[(1S,3R)-3-(4H-1,2,4-triazol-4-yl)cyclohexyl]benzenesulfonamide;
3-ethyl-N-[(1S,3R)-3-(4H-1,2,4-triazol-4-yl)cyclohexyl]-4'-(trifluoromethoxy)biphenyl 4-sulfonamide;
2-ethyl-4-imidazo[1,2-a]pyridin-8-yl-N-[(1S,3R)-3-(4H-1,2,4-triazol-4-yl)cyclohexyl]benzenesulfonamide;
4-(5-cyclopropyl-1,2,4-oxadiazol-3-yl)-2-ethyl-N-{(1S,3R)-3-[3-(trifluoromethyl)-4H-1,2,4-triazol-4-yl]cyclohexyl}benzenesulfonamide;
4-(5-cyclopropyl-1,2,4-oxadiazol-3-yl)-2-ethyl-N-[(1S,3R)-3-(3-cyclopropyl-4H-1,2,4-triazol-4-yl)cyclohexyl]benzenesulfonamide;
2-ethyl-N-[(1S,3R)-3-(4H-1,2,4-triazol-4-yl)cyclohexyl]biphenyl-4-sulfonamide;
2-ethyl-4-(6-methoxypyridin-3-yl)-N-[(1S,3R)-3-(4H-1,2,4-triazol-4-yl)cyclohexyl]benzenesulfonamide;
4-(6-cyanopyridin-3-yl)-2-ethyl-N-[(1S,3R)-3-(4H-1,2,4-triazol-4-yl)cyclohexyl]benzenesulfonamide;
2-ethyl-4-(6-methylpyridin-3-yl)-N-[(1S,3R)-3-(4H-1,2,4-triazol-4-yl)cyclohexyl]benzenesulfonamide;
4-(2-aminopyrimidin-5-yl)-2-ethyl-N-[(1S,3R)-3-(4H-1,2,4-triazol-4-yl)cyclohexyl]benzenesulfonamide;
2-ethyl-4-pyridin-4-yl-N-[(1S,3R)-3-(4H-1,2,4-triazol-4-yl)cyclohexyl]benzenesulfonamide;
3-ethyl-2'-fluoro-N-[(1S,3R)-3-(4H-1,2,4-triazol-4-yl)cyclohexyl]benzenesulfonamide;
3-ethyl-3'-fluoro-N-[(1S,3R)-3-(4H-1,2,4-triazol-4-yl)cyclohexyl]benzenesulfonamide;
3-ethyl-4'-fluoro-N-[(1S,3R)-3-(4H-1,2,4-triazol-4-yl)cyclohexyl]benzenesulfonamide;
2-ethyl-4-pyridin-3-yl-N-[(1S,3R)-3-(4H-1,2,4-triazol-4-yl)cyclohexyl]benzenesulfonamide;
3-ethyl-4'-methoxy-N-[(1S,3R)-3-(4H-1,2,4-triazol-4-yl)cyclohexyl]biphenyl-4-sulfonamide;
2-ethyl-4-(2-methoxypyridin-3-yl)-N-[(1S,3R)-3-(4H-1,2,4-triazol-4-yl)cyclohexyl]benzenesulfonamide;
3-ethyl-3'-methoxy-N-[(1S,3R)-3-(4H-1,2,4-triazol-4-yl)cyclohexyl]biphenyl-4-sulfonamide;
3-ethyl-2'-methoxy-N-[(1S,3R)-3-(4H-1,2,4-triazol-4-yl)cyclohexyl]biphenyl-4-sulfonamide;
3-ethyl-3'-fluoro-4'-methoxy-N-[(1S,3R)-3-(4H-1,2,4-triazol-4-yl)cyclohexyl]biphenyl-4-sulfonamide;
3-ethyl-3',5'-dimethoxy-N-[(1S,3R)-3-(4H-1,2,4-triazol-4-yl)cyclohexyl]biphenyl-4-sulfonamide;
3-ethyl-2',4'-difluoro-N-[(1S,3R)-3-(4H-1,2,4-triazol-4-yl)cyclohexyl]biphenyl-4-sulfonamide;
3-ethyl-3',4'-difluoro-N-[(1S,3R)-3-(4H-1,2,4-triazol-4-yl)cyclohexyl]biphenyl-4-sulfonamide;
4-(1,3-benzodioxol-5-yl)-2-ethyl-N-[(1S,3R)-3-(4H-1,2,4-triazol-4-yl)cyclohexyl]benzenesulfonamide;
4'-(difluoromethoxy)-3-ethyl-N-[(1S,3R)-3-(4H-1,2,4-triazol-4-yl)cyclohexyl]biphenyl-4-sulfonamide;
4-(3,5-dimethylisoxazol-4-yl)-2-ethyl-N-[(1S,3R)-3-(4H-1,2,4-triazol-4-yl)cyclohexyl]benzenesulfonamide;
3-ethyl-N-[(1S,3R)-3-(4H-1,2,4-triazol-4-yl)cyclohexyl]2'-(trifluoromethoxy)biphenyl-4-sulfonamide;
3-ethyl-2'-methoxy-N-[(1S,3R)-3-(4H-1,2,4-triazol-4-yl)cyclohexyl]-6'-(trifluoromethoxy)biphenyl-4-sulfonamide;
3-ethyl-3'-fluoro-N-[(1S,3R)-3-(4H-1,2,4-triazol-4-yl)cyclohexyl]-4'-(trifluoromethoxy)biphenyl-4-sulfonamide;
3-ethyl-4'-hydroxy-N-[(1S,3R)-3-(4H-1,2,4-triazol-4-yl)cyclohexyl]biphenyl-4-sulfonamide;
2-ethyl-4-quinolin-8-yl-N-[(1S,3R)-3-(4H-1,2,4-triazol-4-yl)cyclohexyl]benzenesulfonamide;
2-ethyl-4-(2-hydroxypyridin-3-yl)-N-[(1S,3R)-3-(4H-1,2,4-triazol-4-yl)cyclohexyl]benzenesulfonamide;
3-ethyl-N-[(1S,3R)-3-(4H-1,2,4-triazol-4-yl)cyclohexyl]-4'-(2,2,2-trifluorethoxy)biphenyl-4-sulfonamide;
2-ethyl-4-(6-isopropoxypyridin-3-yl)-N-[(1S,3R)-3-(4H-1,2,4-triazol-4-yl)cyclohexyl]benzenesulfonamide;
3-ethyl-4'-isopropoxy-N-[(1S,3R)-3-(4H-1,2,4-triazol-4-yl)cyclohexyl]biphenyl-4-sulfonamide;
2-ethyl-N-[(1S,3R)-3-(4H-1,2,4-triazol-4-yl)cyclohexyl]-4-[6-(2,2,2-trifluoroethoxy)pyridin-3-yl]benzenesulfonamide;
2-ethyl-4-(6-fluoropyridin-3-yl)-N-[(1S,3R)-3-(4H-1,2,4-triazol-4-yl)cyclohexyl]benzenesulfonamide;
2-ethyl-4-(5-methoxypyridin-3-yl)-N-[(1S,3R)-3-(4H-1,2,4-triazol-4-yl)cyclohexyl]benzenesulfonamide;
N'-[3'-ethyl-4'-({[(1S,3R)-3-(4H-1,2,4-triazol-4-yl)cyclohexyl]amino}sulfonyl)biphenyl-4-yl]acetamide;
3-ethyl-N-[(1S,3R)-3-(4H-1,2,4-triazol-4-yl)cyclohexyl]-4'-[2,2,2-trifluoro-1-(trifluoromethyl)ethoxy]biphenyl-4-sulfonamide;
4-[6-(cyclobutyloxy)pyridin-3-yl]-2-ethyl-N-[(1S,3R)-3-(4H-1,2,4-triazol-4-yl)cyclohexyl]benzenesulfonamide;
4-(6-chloroimidazo[1,2-a]pyridin-8-yl)-2-ethyl-N-[(1S,3R)-3-(4H-1,2,4-triazol-4-yl)cyclohexyl]benzenesulfonamide;
2-ethyl-4-pyrazolo[1,5-a]pyrimidin-6-yl-N-[(1S,3R)-3-(4H-1,2,4-triazol-4-yl)cyclohexyl]benzenesulfonamide;
2-ethyl-4-pyrazolo[1,5-a]pyrimidin-5-yl-N-[(1S,3R)-3-(4H-1,2,4-triazol-4-yl)cyclohexyl]benzenesulfonamide;
2-ethyl-4-(1,3-thiazol-2-yl)-N-[(1S,3R)-3-(4H-1,2,4-triazol-4-yl)cyclohexyl]benzenesulfonamide;
2-ethyl-4-(1,3-thiazol-5-yl)-N-[(1S,3R)-3-(4H-1,2,4-triazol-4-yl)cyclohexyl]benzenesulfonamide;
2-ethyl-4-(1,3-thiazol-4-yl)-N-[(1S,3R)-3-(4H-1,2,4-triazol-4-yl)cyclohexyl]benzenesulfonamide;
2-ethyl-4-(1,2,4-thiadiazol-5-yl)-N-[(1S,3R)-3-(4H-1,2,4-triazol-4-yl)cyclohexyl]benzenesulfonamide;
2-ethyl-4-[5-(methoxymethyl)-1,3-thiazol-2-yl]-N-[(1S,3R)-3-(4H-1,2,4-triazol-4-yl)cyclohexyl]benzenesulfonamide;
4-(5-cyclopropyl-1,2,4-oxadiazol-3-yl)-2-ethyl-N-[(1S,3R)-3-(3-methyl-4H-1,2,4-triazol-4-yl)cyclohexyl]benzenesulfonamide;
2-ethyl-4-(6-isopropoxypyridin-3-yl)-N-[(1S,3R)-3-(3-methyl-4H-1,2,4-triazol-4-yl)cyclohexyl]benzenesulfonamide;
3-ethyl-N-[(1S,3R)-3-(3-methyl-4H-1,2,4-triazol-4-yl)cyclohexyl]-4'-(trifluoromethoxy)biphenyl-4-sulfonamide;
2-ethyl-N-[(1S,3R)-3-(3-methyl-4H-1,2,4-triazol-4-yl)cyclohexyl]-4-[6-(2,2,2-trifluoroethoxyl)pyridin-3-yl]benzenesulfonamide;
3-ethyl-3'-fluoro-N-[(1S,3R)-3-(3-methyl-4H-1,2,4-triazol-4-yl)cyclohexyl]-4'-(trifluoromethoxy)biphenyl-4-sulfonamide;
2-ethyl-N-[(1S,3R)-3-(4H-1,2,4-triazol-4-yl)cyclohexyl]-4-(4,4,4-trifluorobutoxyl)benzenesulfonamide;
2-ethyl-N-[(1S,3R)-3-(3-methyl-4H-1,2,4-triazol-4-yl)cyclohexyl]-4-(4,4,4-trifluorobutoxyl)benzenesulfonamide;
2-ethyl-N-[(1S,3R)-3-(4H-1,2,4-triazol-4-yl)cyclohexyl]-4-(3,3,3-trifluoropropoxyl)benzenesulfonamide;

3-ethyl-T-methyl-N-[(1S,3R)-3-(4H-1,2,4-triazol-4-yl)cyclohexyl]-4'-(trifluoromethoxy)biphenyl-4-sulfonamide;

3-ethyl-N-[(1S,3R)-3-(4H-1,2,4-triazol-4-yl)cyclohexyl]-2',4'-bis(trifluoromethyl)biphenyl-4-sulfonamide;

3-ethyl-T-methyl-N-[(1S,3R)-3-(4H-1,2,4-triazol-4-yl)cyclohexyl]-4'-(trifluoromethyl)biphenyl-4-sulfonamide;

3-ethyl-N-[(1S,3R)-3-(4H-1,2,4-triazol-4-yl)cyclohexyl]-3',5'-bis(trifluoromethyl)biphenyl-4-sulfonamide;

4-(5-cyclopropyl-1,2,4-oxadiazol-3-yl)-N-[(1S,3R)-3-(3-cyclopropyl-4H-1,2,4-triazol-4-yl)cyclohexyl]-2-(trifluromethoxy)benzenesulfonamide;

4-(5-cyclobutyl-1,2,4-oxadiazol-3-yl)-N-[(1S,3R)-3-(3-cyclopropyl-4H-1,2,4-triazol-4-yl)cyclohexyl]-2-(trifluromethoxy)benzenesulfonamide;

N-[(1S,3R)-3-(3-cyclopropyl-4H-1,2,4-triazol-4-yl)cyclohexyl]-4-[5-(3,3-difluorocyclobutyl)-1,2,4-oxadiazol-3-yl]-2-(trifluoromethoxy)benzenesulfonamide;

N-[(1S,3R)-3-(4H-1,2,4-triazol-4-yl)cyclohexyl]-3,4'-bis(trifluoromethoxy)biphenyl-4-sulfonamide;

N-[(1S,3R)-3-(3-methyl-4H-1,2,4-triazol-4-yl)cyclohexyl]-3,4'-bis(trifluoromethoxy)biphenyl-4-sulfonamide;

N-[(1S,3R)-3-(3-methyl-4H-1,2,4-triazol-4-yl)cyclohexyl]-4-[6-(2,2,2-trifluoroethoxyl)pyridin-3-yl]-2-(trifluoromethoxy)benzenesulfonamide;

4-(5-cyclobutyl-1,2,4-oxadiazol-3-yl)-N-[(1S,3R)-3-(3-methyl-4H-1,2,4-triazol-4-yl)cyclohexyl]-2-(trifluoromethoxy)benzenesulfonamide;

4-(5-cyclopentyl-1,2,4-oxadiazol-3-yl)-N-[(1S,3R)-3-(3-methyl-4H-1,2,4-triazol-4-yl)cyclohexyl]-2-(trifluoromethoxy)benzenesulfonamide;

4-(5-cyclopropyl-1,2,4-oxadiazol-3-yl)-N-[(1R,5S)-3,3-difluoro-5-(4H-1,2,4-triazol-4-yl)cyclohexyl]-3-ethylbiphenyl-4-sulfonamide;

4'-(difluoromethoxy)-N-[(1R,5S)-3,3-difluoro-5-(4H-1,2,4-triazol-4-yl)cyclohexyl]-2-ethylbenzenesulfonamide;

N-[(1R,5S)-3,3-difluoro-5-(4H-1,2,4-triazol-4-yl)cyclohexyl]-2-ethyl-4-[6-(2,2,2-trifluoroethoxyl)pyridin-3-yl]benzenesulfonamide;

N-[(1R,5S)-3,3-difluoro-5-(4H-1,2,4-triazol-4-yl)cyclohexyl]-3-ethyl-4'-(trifluoromethoxy)biphenyl-4-sulfonamide;

4-(5-cyclopropyl-1,2,4-oxadiazol-3-yl)-N-[(1R,5S)-3,3-difluoro-5-(3-methyl-4H-1,2,4-triazol-4-yl)cyclohexyl]-2-ethylbenzenesulfonamide;

N-[(1R,5S)-3,3-difluoro-5-(3-methyl-4H-1,2,4-triazol-4-yl)cyclohexyl]-3-ethyl-4'-(trifluoromethoxy)biphenyl-4-sulfonamide;

N-[(1R,5S)-3,3-difluoro-5-(3-methyl-4H-1,2,4-triazol-4-yl)cyclohexyl]-2-ethyl-4-[6-(2,2,2-trifluoroethoxyl)pyridin-3-yl]benzenesulfonamide;

2-fluoro-N-[(1S,3R)-3-(4H-1,2,4-triazol-4-yl)cyclohexyl]-4'-(trifluoromethoxy)biphenyl-4-sulfonamide;

2-fluoro-N-[(1S,3R)-3-(4H-1,2,4-triazol-4-yl)cyclohexyl]-4'-(2,2,2-trifluoroethoxyl)biphenyl-4-sulfonamide;

4'-(difluoromethoxy)-2-fluoro-N-[(1S,3R)-3-(4H-1,2,4-triazol-4-yl)cyclohexyl]biphenyl-4-sulfonamide;

2-fluoro-4'-isopropoxy-N-[(1S,3R)-3-(4H-1,2,4-triazol-4-yl)cyclohexyl]biphenyl-4-sulfonamide;

3-fluoro-4-(6-isopropoxypyridin-3-yl)-N-[(1S,3R)-3-(4H-1,2,4-triazol-4-yl)cyclohexyl]benzenesulfonamide;

3-fluoro-N-[(1S,3R)-3-(4H-1,2,4-triazol-4-yl)cyclohexyl]-4-[6-(2,2,2-trifluoroethoxyl)pyridin-3-yl]benzenesulfonamide;

2-fluoro-N-[(1S,3R)-3-(3-methyl-4H-1,2,4-triazol-4-yl)cyclohexyl]-4'-(trifluoromethoxy)biphenyl-4-sulfonamide;

2-fluoro-N-[(1S,3R)-3-(3-methyl-4H-1,2,4-triazol-4-yl)cyclohexyl]-4'-(2,2,2-trifluoroethoxyl)biphenyl-4-sulfonamide;

4'-(difluoromethoxy)-2-fluoro-N-[(1S,3R)-3-(3-methyl-4H-1,2,4-triazol-4-yl)cyclohexyl]biphenyl-4-sulfonamide;

3-fluoro-4-(6-isopropoxypyridin-3-yl)-N-[(1S,3R)-3-(3-methyl-4H-1,2,4-triazol-4-yl)cyclohexyl]benzenesulfonamide;

3-fluoro-N-[(1S,3R)-3-(3-methyl-4H-1,2,4-triazol-4-yl)cyclohexyl]-4-[6-(2,2,2-trifluoroethoxyl)pyridin-3-yl]benzenesulfonamide;

4-(6-chloro-5-fluoropyridin-3-yl)-3-fluoro-N-[(1S,3R)-3-(3-methyl-4H-1,2,4-triazol-4-yl)cyclohexyl]benzenesulfonamide;

4-(5-cyclopropyl-1,2,4-oxadiazol-3-yl)-3-fluoro-N-[(1S,3R)-3-(3-methyl-4H-1,2,4-triazol-4-yl)cyclohexyl]benzenesulfonamide;

3-fluoro-4-(4-fluorobutoxy)-N-[(1S,3R)-3-(3-methyl-4H-1,2,4-triazol-4-yl)cyclohexyl]benzenesulfonamide 4-butoxy-3-fluoro-N-[(1S,3R)-3-(3-methyl-4H-1,2,4-triazol-4-yl)cyclohexyl]benzenesulfonamide;

N-[(1R,5S)-3,3-difluoro-5-(4H-1,2,4-triazol-4-yl)cyclohexyl]-2-fluoro-4'-(trifluoromethoxy)biphenyl-4-sulfonamide;

N-[(1R,5S)-3,3-difluoro-5-(4H-1,2,4-triazol-4-yl)cyclohexyl]-2-fluoro-4'-isopropoxybiphenyl-4-sulfonamide;

N-[(1R,5S)-3,3-difluoro-5-(4H-1,2,4-triazol-4-yl)cyclohexyl]-3-fluoro-4-[6-(2,2,2-trifluoroethoxyl)pyridin-3-yl]benzenesulfonamide;

N-[(1R,5S)-3,3-difluoro-5-(3-methyl-4H-1,2,4-triazol-4-yl)cyclohexyl]-2-fluoro-4'-(trifluoromethoxy)biphenyl-4-sulfonamide;

N-[(1R,5S)-3,3-difluoro-5-(3-methyl-4H-1,2,4-triazol-4-yl)cyclohexyl]-3-fluoro-4-[6-(2,2,2-trifluoroethoxyl)pyridin-3-yl]benzenesulfonamide;

N-[(1R,5S)-3,3-difluoro-5-(3-methyl-4H-1,2,4-triazol-4-yl)cyclohexyl]-3-fluoro-4-(4-fluorobutoxyl)benzenesulfonamide;

4-butoxy-N-[(1R,5S)-3,3-difluoro-5-(3-methyl-4H-1,2,4-triazol-4-yl)cyclohexyl]-3-fluorobenzenesulfonamide;

3-fluoro-N-[(1S,3R)-3-(4H-1,2,4-triazol-4-yl)cyclohexyl]-4'-(trifluoromethoxy)biphenyl-4-sulfonamide;

2-fluoro-N-[(1S,3R)-3-(4H-1,2,4-triazol-4-yl)cyclohexyl]-4-[6-(2,2,2-trifluoroethoxyl)pyridin-3-yl]benzenesulfonamide;

4-(5-cyclopropyl-1,2,4-oxadiazol-3-yl)-2-fluoro-N-[(1S,3R)-3-(3-methyl-4H-1,2,4-triazol-4-yl)cyclohexyl]benzenesulfonamide;

3-fluoro-N-[(1S,3R)-3-(3-methyl-4H-1,2,4-triazol-4-yl)cyclohexyl]-4'-(trifluoromethoxy)biphenyl-4-sulfonamide;

2-fluoro-N-[(1S,3R)-3-(3-methyl-4H-1,2,4-triazol-4-yl)cyclohexyl]-4-[6-(2,2,2-trifluoroethoxyl)pyridin-3-yl]benzenesulfonamide;

4-butoxy-2-fluoro-N-[(1S,3R)-3-(3-methyl-4H-1,2,4-triazol-4-yl)cyclohexyl]benzenesulfonamide;

2-cyclopropyl-4-(5-cyclopropyl-1,2,4-oxadiazol-3-yl)-N-[(1S,3R)-3-(4H-1,2,4-triazol-4-yl)cyclohexyl]benzenesulfonamide;

2-cyclopropyl-N-[(1S,3R)-3-(4H-1,2,4-triazol-4-yl)cyclohexyl]-4-[5-(trifluoromethyl)-1,2,4-oxadiazol-3-yl]benzenesulfonamide;
2-cyclopropyl-4-[5-(1,1-difluoroethyl)-1,2,4-oxadiazol-3-yl]-N-[(1S,3R)-3-(4H-1,2,4-triazol-4-yl)cyclohexyl]benzenesulfonamide;
2-cyclopropyl-4-[5-(1,1-difluoropropyl)-1,2,4-oxadiazol-3-yl]-N-[(1S,3R)-3-(4H-1,2,4-triazol-4-yl)cyclohexyl]benzenesulfonamide-1,1-difluoroethylene;
2-cyclopropyl-4-[5-(1-hydroxycyclopropyl)-1,2,4-oxadiazol-3-yl]-N-[(1S,3R)-3-(4H-1,2,4-triazol-4-yl)cyclohexyl]benzenesulfonamide;
4-(5-cyclobutyl-1,2,4-oxadiazol-3-yl)-2-cyclopropyl-N-[(1S,3R)-3-(4H-1,2,4-triazol-4-yl)cyclohexyl]benzenesulfonamide;
2-cyclopropyl-4-(5-cyclopropyl-1,2,4-oxadiazol-3-yl)-N-[(1R,5S)-3,3-difluoro-5-(3-methyl-4H-1,2,4-triazol-4-yl)cyclohexyl]benzenesulfonamide;
3,5-difluoro-N-[(1S,3R)-3-(4H-1,2,4-triazol-4-yl)cyclohexyl]benzenesulfonamide;
N-[(1S,3R)-3-(4H-1,2,4-triazol-4-yl)cyclohexyl]-3,5-bis(trifluoromethyl)benzenesulfonamide;
N-[(1S,3R)-3-(4H-1,2,4-triazol-4-yl)cyclohexyl]-3 (trifluoromethoxy)benzenesulfonamide;
3-(difluoromethoxy)-N-[(1S,3R)-3-(4H-1,2,4-triazol-4-yl)cyclohexyl]benzenesulfonamide;
3,5-dimethyl-N-[(1S,3R)-3-(4H-1,2,4-triazol-4-yl)cyclohexyl]benzenesulfonamide;
3-tert-butyl-N-[(1S,3R)-3-(4H-1,2,4-triazol-4-yl)cyclohexyl]benzenesulfonamide;
N-[(1S,3R)-3-(4H-1,2,4-triazol-4-yl)cyclohexyl]biphenyl-3-sulfonamide;
3,5-dichloro-N-[(1S,3R)-3-(4H-1,2,4-triazol-4-yl)cyclohexyl]benzenesulfonamide;
3-bromo-N-[(1S,3R)-3-(4H-1,2,4-triazol-4-yl)cyclohexyl]-5-(trifluoromethyl)benzenesulfonamide;
4-(5-cyclopropyl-1,2,4-oxadiazol-3-yl)-N-[(1S,3R)-3-(4H-1,2,4-triazol-4-yl)cyclohexyl]benzenesulfonamide;
6-ethyl-N-[(1S,3R)-3-(4H-1,2,4-triazol-4-yl)cyclohexyl]biphenyl-3-sulfonamide;
4-ethyl-3-(2-methoxypyridin-3-yl)-N-[(1S,3R)-3-(4H-1,2,4-triazol-4-yl)cyclohexyl]benzenesulfonamide;
2,5-difluoro-N-[(1S,3R)-3-(4H-1,2,4-triazol-4-yl)cyclohexyl]-4'-(trifluoromethoxy)biphenyl-4-sulfonamide;
N-[(1S,3R)-3-(4H-1,2,4-triazol-4-yl)cyclohexyl]-4-(trifluoromethoxy)benzenesulfonamide;
4-phenoxy-N-[(1S,3R)-3-(4H-1,2,4-triazol-4-yl)cyclohexyl]benzenesulfonamide;
4-butoxy-N-[(1S,3R)-3-(4H-1,2,4-triazol-4-yl)cyclohexyl]benzenesulfonamide;
3,4-dimethoxy-N-[(1S,3R)-3-(4H-1,2,4-triazol-4-yl)cyclohexyl]benzenesulfonamide;
2,4-dimethoxy-N-[(1S,3R)-3-(4H-1,2,4-triazol-4-yl)cyclohexyl]benzenesulfonamide;
4-isopropoxy-N-[(1S,3R)-3-(4H-1,2,4-triazol-4-yl)cyclohexyl]benzenesulfonamide;
4-ethoxy-N-[(1S,3R)-3-(4H-1,2,4-triazol-4-yl)cyclohexyl]benzenesulfonamide;
4-{[3-chloro-5-(trifluoromethyl)pyridin-2-yl]oxy}-N-[(1S,3R)-3-(4H-1,2,4-triazol-4-yl)cyclohexyl]benzenesulfonamide;
N-[(1S,3R)-3-(4H-1,2,4-triazol-4-yl)cyclohexyl]-4-(4,4,4-trifluorobutoxyl)benzenesulfonamide;
4-pentyl-N-[(1S,3R)-3-(4H-1,2,4-triazol-4-yl)cyclohexyl]benzenesulfonamide;
4-(5-cyclopropyl-1,2,4-oxadiazol-3-yl)-N-[(1S,3R)-3-(3-methyl-4H-1,2,4-triazol-4-yl)cyclohexyl]benzenesulfonamide;
4-tert-butyl-N-[(1S,3R)-3-(3-methyl-4H-1,2,4-triazol-4-yl)cyclohexyl]benzenesulfonamide;
4-isopropyl-N-[(1S,3R)-3-(3-methyl-4H-1,2,4-triazol-4-yl)cyclohexyl]benzenesulfonamide;
4-(5-cyclopropyl-1H-pyrazol-1-yl)-N-[(1S,3R)-3-(3-methyl-4H-1,2,4-triazol-4-yl)cyclohexyl]benzenesulfonamide;
4-(3-cyclopropyl-1H-pyrazol-1-yl)-N-[(1S,3R)-3-(3-methyl-4H-1,2,4-triazol-4-yl)cyclohexyl]benzenesulfonamide;
4-(4-methyl-1H-imidazol-1-yl)-N-[(1S,3R)-3-(3-methyl-4H-1,2,4-triazol-4-yl)cyclohexyl]benzenesulfonamide;
4-butoxy-N-[(1S,3R)-3-(3-methyl-4H-1,2,4-triazol-4-yl)cyclohexyl]benzenesulfonamide;
N-[(1S,3R)-3-(3-methyl-4H-1,2,4-triazol-4-yl)cyclohexyl]-4-(4,4,4-trifluorobutoxyl)benzenesulfonamide;
4-(4-fluorobutoxy)-N-[(1S,3R)-3-(3-methyl-4H-1,2,4-triazol-4-yl)cyclohexyl]benzenesulfonamide;
4-butoxy-2,5-difluoro-N-[(1S,3R)-3-(3-methyl-4H-1,2,4-triazol-4-yl)cyclohexyl]benzenesulfonamide;
4-butoxy-N-[(1S,3R)-3-(3-cyclopropyl-4H-1,2,4-triazol-4-yl)cyclohexyl]benzenesulfonamide;
4-butoxy-N-[(1S,3R)-3-(3-cyclopropyl-4H-1,2,4-triazol-4-yl)cyclohexyl]-3-fluorobenzenesulfonamide;
4-butoxy-N-[(1S,3R)-3-(3-cyclopropyl-4H-1,2,4-triazol-4-yl)cyclohexyl]-2-fluorobenzenesulfonamide;
N-[(1R,5S)-3,3-difluoro-5-(4H-1,2,4-triazol-4-yl)cyclohexyl]-3-ethylbenzenesulfonamide;
4-(5-cyclopropyl-1,2,4-oxadiazol-3-yl)-N-[(1R,5S)-3,3-difluoro-5-(3-methyl-4H-1,2,4-triazol-4-yl)cyclohexyl]benzenesulfonamide;
4-butoxy-N-[(1R,5S)-3,3-difluoro-5-(3-methyl-4H-1,2,4-triazol-4-yl)cyclohexyl]benzenesulfonamide;
N-[(1R,5S)-3,3-difluoro-5-(3-methyl-4H-1,2,4-triazol-4-yl)cyclohexyl]-4-(4-fluorobutoxy)-benzenesulfonamide;
2,6-dicyclopropyl-4-(5-cyclopropyl-1,2,4-oxadiazol-3-yl)-N-[(1S,3R)-3-(4H-1,2,4-triazol-4-yl)cyclohexyl]benzenesulfonamide;
4-(5-cyclobutyl-1,2,4-oxadiazol-3-yl)-2,6-dicyclopropyl-N-[(1S,3R)-3-(4H-1,2,4-triazol-4-yl)cyclohexyl]benzenesulfonamide;
2,6-dicyclopropyl-4-[5-(3,3-difluorocyclobutyl)-1,2,4-oxadiazol-3-yl]-N-[(1S,3R)-3-(4H-1,2,4-triazol-4-yl)cyclohexyl]benzenesulfonamide;
2-cyclopropyl-4-(5-cyclopropyl-1,2,4-oxadiazol-3-yl)-6-fluoro-N-[(1S,3R)-3-(4H-1,2,4-triazol-4-yl)cyclohexyl]benzenesulfonamide;
4-(5-cyclobutyl-1,2,4-oxadiazol-3-yl)-2-cyclopropyl-6-fluoro-N-[(1S,3R)-3-(4H-1,2,4-triazol-4-yl)cyclohexyl]benzenesulfonamide;
3-bromo-N-[(1S,3R)-3-(4H-1,2,4-triazol-4-yl)cyclohexyl]-5-(trifluoromethyl)benzenesulfonamide;
3-(4,4,5,5-tetramethyl-1,3,2-dioxaborolan-2-yl)-N-[(1S,3R)-3-(4H-1,2,4-triazol-4-yl)cyclohexyl]-5-(trifluoromethyl)benzenesulfonamide;
3-[1,2,4]triazolo[4,3-a]pyridin-8-yl-N-[(1S,3R)-3-(4H-1,2,4-triazol-4-yl)cyclohexyl]5-(trifluoromethyl)benzenesulfonamide;
N-[(1R,5S)-3,3-difluoro-5-(3-methyl-4H-1,2,4-triazol-4-yl)cyclohexyl]-3-quinolin-8-yl-5-(trifluoromethyl)benzenesulfonamide;

N-[(1R,5S)-3,3-difluoro-5-(3-methyl-4H-1,2,4-triazol-4-yl)cyclohexyl]-3-ethyl-5-quinolin-8-ylbenzenesulfonamide;

4'-fluoro-N-[(1S,3R)-3-(3-methyl-4H-1,2,4-triazol-4-yl)cyclohexyl]-5-(trifluoromethyl)biphenyl-3-sulfonamide;

4'-fluoro-N-[(1S,3R)-3-(4H-1,2,4-triazol-4-yl)cyclohexyl]-5-(trifluoromethyl)biphenyl-3-sulfonamide;

N-[(1R,5S)-3,3-difluoro-5-(4H-1,2,4-triazol-4-yl)cyclohexyl]-4'-fluoro-5-(trifluoromethyl)biphenyl-3-sulfonamide;

3-ethyl-5-quinolin-8-yl-N-[(1S,3R)-3-(4H-1,2,4-triazol-4-yl)cyclohexyl]benzenesulfonamide;

N-[(1R,5S)-3,3-difluoro-5-(4H-1,2,4-triazol-4-yl)cyclohexyl]-3-quinolin-8-yl-5-(trifluoromethyl)benzenesulfonamide;

N-[(1S,3R)-3-(4H-1,2,4-triazol-4-yl)cyclohexyl]-5-(trifluoromethyl)biphenyl-3-sulfonamide;

3-(6-methoxypyridin-3-yl)-N-[(1S,3R)-3-(4H-1,2,4-triazol-4-yl)cyclohexyl]-5-(trifluoromethyl)benzenesulfonamide;

3-(2-methoxypyridin-3-yl)-N-[(1S,3R)-3-(4H-1,2,4-triazol-4-yl)cyclohexyl]-5-(trifluoromethyl)benzenesulfonamide;

3-(5-cyclopropyl-1,2,4-oxadiazol-3-yl)-N-[(1S,3R)-3-(4H-1,2,4-triazol-4-yl)cyclohexyl]-5-(trifluoromethyl)benzenesulfonamide;

3-(6-hydroxypyridin-3-yl)-N-[(1S,3R)-3-(4H-1,2,4-triazol-4-yl)cyclohexyl]-5-(trifluoromethyl)benzenesulfonamide;

3-(2-hydroxypyridin-3-yl)-N-[(1S,3R)-3-(4H-1,2,4-triazol-4-yl)cyclohexyl]-5-(trifluoromethyl)benzenesulfonamide;

N-[(1S,3R)-3-(4H-1,2,4-triazol-4-yl)cyclohexyl]-4',5-bis(trifluoromethyl)biphenyl-3-sulfonamide N-[(1S,3R)-3-(4H-1,2,4-triazol-4-yl)cyclohexyl]-2'-(trifluoromethoxy)-5-(trifluoromethyl)biphenyl-3-sulfonamide 3-pyridin-4-yl-N-[(1S,3R)-3-(4H-1,2,4-triazol-4-yl)cyclohexyl]-5-(trifluoromethyl)benzenesulfonamide;

3-(1-naphthyl)-N-[(1S,3R)-3-(4H-1,2,4-triazol-4-yl)cyclohexyl]-5-(trifluoromethyl)benzenesulfonamide;

3-quinolin-6-yl-N-[(1S,3R)-3-(4H-1,2,4-triazol-4-yl)cyclohexyl]-5-(trifluoromethyl)benzenesulfonamide;

3-(1-benzothien-7-yl)-N-[(1S,3R)-3-(4H-1,2,4-triazol-4-yl)cyclohexyl]-5-(trifluoromethyl)benzenesulfonamide;

3-pyridin-3-yl-N-[(1S,3R)-3-(4H-1,2,4-triazol-4-yl)cyclohexyl]-5-(trifluoromethyl)benzenesulfonamide;

3'-fluoro-N-[(1S,3R)-3-(4H-1,2,4-triazol-4-yl)cyclohexyl]-5-(trifluoromethyl)biphenyl-3-sulfonamide;

2'-fluoro-N-[(1S,3R)-3-(4H-1,2,4-triazol-4-yl)cyclohexyl]-5-(trifluoromethyl)biphenyl-3-sulfonamide;

N-[(1S,3R)-3-(4H-1,2,4-triazol-4-yl)cyclohexyl]-3'-(trifluoromethoxy)-5-(trifluoromethyl)biphenyl-3-sulfonamide;

3-(2-fluoropyridin-4-yl)-N-[(1S,3R)-3-(4H-1,2,4-triazol-4-yl)cyclohexyl]-5-(trifluoromethyl)benzenesulfonamide;

3-(5-aminopyrazin-2-yl)-N-[(1S,3R)-3-(4H-1,2,4-triazol-4-yl)cyclohexyl]-5-(trifluoromethyl)benzenesulfonamide;

3-(6-fluoropyridin-2-yl)-N-[(1S,3R)-3-(4H-1,2,4-triazol-4-yl)cyclohexyl]-5-(trifluoromethyl)benzenesulfonamide;

3-isoquinolin-4-yl-N-[(1S,3R)-3-(4H-1,2,4-triazol-4-yl)cyclohexyl]-5-(trifluoromethyl)benzenesulfonamide;

3-isoquinolin-5-yl-N-[(1S,3R)-3-(4H-1,2,4-triazol-4-yl)cyclohexyl]-5-(trifluoromethyl)benzenesulfonamide;

3-imidazo[1,2-a]pyridin-5-yl-N-[(1S,3R)-3-(4H-1,2,4-triazol-4-yl)cyclohexyl]-5-(trifluoromethyl)benzenesulfonamide;

3-(5-chloro-2-fluoropyridin-3-yl)-N-[(1S,3R)-3-(4H-1,2,4-triazol-4-yl)cyclohexyl]-5-(trifluoromethyl)benzenesulfonamide;

3-(5-fluoropyridin-3-yl)-N-[(1S,3R)-3-(4H-1,2,4-triazol-4-yl)cyclohexyl]-5-(trifluoromethyl)benzenesulfonamide;

N-[(1S,3R)-3-(4H-1,2,4-triazol-4-yl)cyclohexyl]-3-[2-(2,2,2-trifluoroethoxy)quinolin-8-yl]-5-(trifluoromethyl)benzenesulfonamide;

3-(1-benzofuran-2-yl)-N-[(1S,3R)-3-(4H-1,2,4-triazol-4-yl)cyclohexyl]-5-(trifluoromethyl)benzenesulfonamide;

3-(1-benzothien-2-yl)-N-[(1S,3R)-3-(4H-1,2,4-triazol-4-yl)cyclohexyl]-5-(trifluoromethyl)benzenesulfonamide;

N-[(1S,3R)-3-(4H-1,2,4-triazol-4-yl)cyclohexyl]-3-[2-(2,2,2-trifluoroethoxy)quinolin-7-yl]-5-(trifluoromethyl)benzenesulfonamide;

N-[(1S,3R)-3-(4H-1,2,4-triazol-4-yl)cyclohexyl]-3-(trifluoromethyl)-5-[2-(trifluoromethyl)[1,2,4]triazolo[1,5-b]pyridazin-6-yl]benzenesulfonamide;

3-(2-methylimidazo[1,2-b]pyridazin-6-yl)-N-[(1S,3R)-3-(4H-1,2,4-triazol-4-yl)cyclohexyl]-5-(trifluoromethyl)benzenesulfonamide;

N-[(1S,3R)-3-(4H-1,2,4-triazol-4-yl)cyclohexyl]-3-(trifluoromethyl)-5-[2-(trifluoromethyl)imidazo[1,2-b]pyridazin-6-yl]benzenesulfonamide;

3-pyrazolo[1,5-a]pyrimidin-5-yl-N-[(1S,3R)-3-(4H-1,2,4-triazol-4-yl)cyclohexyl]-5-(trifluoromethyl)benzenesulfonamide;

3-[1,2,4]triazolo[1,5-a]pyridin-7-yl-N-[(1S,3R)-3-(4H-1,2,4-triazol-4-yl)cyclohexyl]-5-(trifluoromethyl)benzenesulfonamide;

N-[(1S,3R)-3-(4H-1,2,4-triazol-4-yl)cyclohexyl]-3-[2-(2,2,2-trifluoroethoxy)pyridin-3-yl]-5-(trifluoromethyl)benzenesulfonamide;

3-ethyl-N-[(1S,3R)-3-(4H-1,2,4-triazol-4-yl)cyclohexyl]-5-[2-(2,2,2-trifluoroethoxy)pyridin-3-yl]benzenesulfonamide: m/z (ES) 510 (MH)+; IC$_{50}$=9.5 nM 3-[1,2,4]triazolo[4,3-a]pyridin-8-yl-N-[(1S,3R)-3-(4H-1,2,4-triazol-4-yl)cyclohexyl]-5-(trifluoromethyl)benzenesulfonamide;

3-(5-fluoro-2-methylquinolin-8-yl)-N-[(1S,3R)-3-(4H-1,2,4-triazol-4-yl)cyclohexyl]-5-(trifluoromethyl)benzenesulfonamide;

3-(2-cyclopropyl[1,2,4]triazolo[1,5-a]pyridin-6-yl)-N-[(1S,3R)-3-(4H-1,2,4-triazol-4-yl)cyclohexyl]-5-(trifluoromethyl)benzenesulfonamide;

3-(3-thienyl)-N-[(1S,3R)-3-(4H-1,2,4-triazol-4-yl)cyclohexyl]-5-(trifluoromethyl)benzenesulfonamide;

3-(2-thienyl)-N-[(1S,3R)-3-(4H-1,2,4-triazol-4-yl)cyclohexyl]-5-(trifluoromethyl)benzenesulfonamide;

3-(6-chloroimidazo[1,2-a]pyridin-8-yl)-N-[(1S,3R)-3-(4H-1,2,4-triazol-4-yl)cyclohexyl]-5-(trifluoromethyl)benzenesulfonamide;

3-imidazo[1,2-a]pyridin-8-yl-N-[(1S,3R)-3-(4H-1,2,4-triazol-4-yl)cyclohexyl]-5-(trifluoromethyl)benzenesulfonamide;

3-ethyl-5-imidazo[1,2-a]pyridin-8-yl-N-[(1S,3R)-3-(4H-1,2,4-triazol-4-yl)cyclohexyl]benzenesulfonamide;

3-[6-chloro-2-(chloromethyl)imidazo[1,2-a]pyridin-8-yl]-N-[(1S,3R)-3-(4H-1,2,4-triazol-4-yl)cyclohexyl]-5-(trifluoromethyl)benzenesulfonamide;

3-[6-chloro-2-(chloromethyl)imidazo[1,2-a]pyridin-8-yl]-5-ethyl-N-[(1S,3R)-3-(4H-1,2,4-triazol-4-yl)cyclohexyl]benzenesulfonamide;

ethyl 6-chloro-8-[3-({[(1S,3R)-3-(4H-1,2,4-triazol-4-yl)cyclohexyl]amino}sulfonyl)-5-(trifluoromethyl)phenyl]imidazo[1,2-a]pyridine-2-carboxylate;

3-ethyl-5-pyrazolo[1,5-a]pyrimidin-6-yl-N-[(1S,3R)-3-(4H-1,2,4-triazol-4-yl)cyclohexyl]benzenesulfonamide;

3-ethyl-N-[(1S,3R)-3-(4H-1,2,4-triazol-4-yl)cyclohexyl]-5-[6-(2,2,2-trifluoroethoxy)pyridazin-3-yl]benzenesulfonamide;

3-ethyl-5-pyridazin-4-yl-N-[(1S,3R)-3-(4H-1,2,4-triazol-4-yl)cyclohexyl]benzenesulfonamide;

3-ethyl-5-pyridazin-3-yl-N-[(1S,3R)-3-(4H-1,2,4-triazol-4-yl)cyclohexyl]benzenesulfonamide;

N-[(1S,3R)-3-(4H-1,2,4-triazol-4-yl)cyclohexyl]-5-(trifluoromethoxy)biphenyl-3-sulfonamide;

3-(2-methoxypyridin-3-yl)-N-[(1S,3R)-3-(4H-1,2,4-triazol-4-yl)cyclohexyl]-5-(trifluoromethoxy)benzenesulfonamide;

5-fluoro-N-[(1S,3R)-3-(4H-1,2,4-triazol-4-yl)cyclohexyl]biphenyl-3-sulfonamide;

3-fluoro-5-(2-methoxypyridin-3-yl)-N-[(1S,3R)-3-(4H-1,2,4-triazol-4-yl)cyclohexyl]benzenesulfonamide;

3-fluoro-5-quinolin-8-yl-N-[(1S,3R)-3-(4H-1,2,4-triazol-4-yl)cyclohexyl]benzenesulfonamide;

4-amino-2-ethyl-N-[(1S,3R)-3-(4H-1,2,4-triazol-4-yl)cyclohexyl]benzenesulfonamide;

2-ethyl-4-(3-methyl-4H-1,2,4-triazol-4-yl)-N-[(1S,3R)-3-(4H-1,2,4-triazol-4-yl)cyclohexyl]benzenesulfonamide;

2-ethyl-4-(1H-tetrazol-1-yl)-N-[(1S,3R)-3-(4H-1,2,4-triazol-4-yl)cyclohexyl]benzenesulfonamide;

2-ethyl-4-(1H-pyrazol-1-yl)-N-[(1S,3R)-3-(4H-1,2,4-triazol-4-yl)cyclohexyl]benzenesulfonamide;

2-ethyl-4-(4-methyl-1H-pyrazol-1-yl)-N-[(1S,3R)-3-(4H-1,2,4-triazol-4-yl)cyclohexyl]benzenesulfonamide;

N-[(1S,3R)-3-(3,5-dimethyl-4H-1,2,4-triazol-4-yl)cyclohexyl]-2,4,6-triisopropylbenzenesulfonamide;

4-(5-cyclopropyl-1,2,4-oxadiazol-3-yl)-N-(3-pyridin-cis-3-ylcyclohexyl)benzenesulfonamide;

3-pyrazolo[1,5-a]pyrimidin-7-yl-N-[(1S,3R)-3-(4H-1,2,4-triazol-4-yl)cyclohexyl]-5-(trifluoromethyl)benzenesulfonamide;

3-(2-cyclopropylpyrimidin-4-yl)-N-[(1R,5S)-3,3-difluoro-5-(3-methyl-4H-1,2,4-triazol-4-yl)cyclohexyl]-5-(trifluoromethyl)benzenesulfonamide;

3-(2-aminopyrimidin-4-yl)-N-[(1R,5S)-3,3-difluoro-5-(3-methyl-4H-1,2,4-triazol-4-yl)cyclohexyl]-5-(trifluoromethyl)benzenesulfonamide;

3-[1,2,4]triazolo[1,5-a]pyrimidin-7-yl-N-[(1R,5S)-3,3-difluoro-5-(3-methyl-4H-1,2,4-triazol-4-yl)cyclohexyl]-5-(trifluoromethyl)benzenesulfonamide;

3-isoxazol-5-yl-N-[(1R,5S)-3,3-difluoro-5-(3-methyl-4H-1,2,4-triazol-4-yl)cyclohexyl]-5-(trifluoromethyl)benzenesulfonamide;

3-(1H)-pyrazol-5-yl)-N-[(1R,5S)-3,3-difluoro-5-(3-methyl-4H-1,2,4-triazol-4-yl)cyclohexyl]-5-(trifluoromethyl)benzenesulfonamide; and 3-(2-cyclopropylpyrazolo[1,5-a]pyrimidin-7-yl)-N-[(1R,5S)-3,3-difluoro-5-(3-methyl-4H-1,2,4-triazol-4-yl)cyclohexyl]-5-(trifluoromethyl)benzenesulfonamide, or a pharmaceutically acceptable salt thereof.

7. A method for treating a disease selected from the group consisting of atherosclerosis; inflammatory pain; nociceptive pain; anaphylaxis; rheumatoid arthritis; acute inflammation; asthma; endotoxic shock; ischemia; gastrointestinal ulceration; transplanted organ rejection; reperfusion injury; inflammatory bowel diseases; edema; rhinitis; thrombosis; bronchitis; urticaria; psoriasis; retinal and corneal diseases; chemically induced liver cirrhosis; ovimplantation in pregnancy; and acute respiratory distress syndrome comprising administering a therapeutically effective amount of a compound of claim 1, or a pharmaceutically acceptable salt thereof, to a patient in need thereof.

8. A pharmaceutical composition comprising the compound of claim 1, or a pharmaceutically acceptable salt thereof, and a pharmaceutically acceptable carrier.

9. The compound which is 2-ethyl-4-(4,4,5,5-tetramethyl-1,3,2-dioxaborolan-2-yl)-N-[(1S,3R)-3-(4H-1,2,4-triazol-4-yl)cyclohexyl]benzenesulfonamide or 2-ethyl-4-nitro-N-[(1S,3R)-3-(4H-1,2,4-triazol-4-yl)cyclohexyl]benzenesulfonamide, or a pharmaceutically acceptable salt thereof.

\* \* \* \* \*